United States Patent [19]

Armstrong

[11] 3,998,714
[45] Dec. 21, 1976

[54] SYSTEM FOR POLLUTION SUPPRESSION
[75] Inventor: Edward T. Armstrong, Butler, N.J.
[73] Assignee: TII Corporation, Lindenhurst, N.Y.
[22] Filed: Dec. 9, 1974
[21] Appl. No.: 531,095

Related U.S. Application Data

[63] Continuation-in-part of Ser. No. 355,738, April 30, 1973, Pat. No. 3,853,764, which is a continuation-in-part of Ser. No. 100,333, Dec. 21, 1970, Pat. No. 3,730,881, which is a continuation-in-part of Ser. No. 813,382, Feb. 28, 1969, Pat. No. 3,549,528, which is a continuation-in-part of Ser. No. 362,118, April 23, 1964, abandoned.

[52] U.S. Cl. .............................. 210/62; 210/632; 210/64
[51] Int. Cl.$^2$ .............................. C02B 3/08
[58] Field of Search .................. 210/50, 49, 62–64, 210/53

[56] References Cited

UNITED STATES PATENTS

| | | | |
|---|---|---|---|
| 1,094,731 | 4/1914 | Linden | 210/50 |
| 1,658,974 | 2/1928 | De Laporte et al. | 210/50 |
| 2,988,221 | 6/1961 | Culp | 210/62 X |
| 3,139,402 | 6/1964 | Armbrust | 210/50 |
| 3,401,115 | 9/1968 | Meyer et al. | 210/62 X |
| 3,422,010 | 1/1969 | Case | 210/50 |
| 3,733,266 | 5/1973 | Bishop et al. | 210/62 X |
| 3,804,755 | 4/1974 | Cervantes | 210/50 |

OTHER PUBLICATIONS

Sewerage and Sewage Treatment, 8th Edition, Babbitt and Baumann, 1958, Wiley.

Primary Examiner—Charles N. Hart
Assistant Examiner—Robert H. Spitzer
Attorney, Agent, or Firm—Oldham & Oldham Co.

[57] ABSTRACT

The present invention relates to a two stage oxidative system for the disinfection of material which may contain nitrogen commonly in the form of ammonia or ammonium as in the treatment of waste or sewage plant effluent by adding a primary oxidizing agent to the effluent to disinfect as well as to lower the pH of the effluent and by adding a secondary oxidizing agent to produce a synergistic disinfection system in which the distribution of ammonium and ammonia is shifted to nearly all ammonium. A desirable pH level is 7 or less with desirable primary oxidizing agents including aluminum chloride or ferric chloride with desirable secondary oxidizing agents including chlorine, chlorine dioxide, ozone as in oxygen or air, or sodium hypochlorite. The invention further relates to an activated sludge aeration system in which desirably there are no stagnant areas and maximum diffusion is achieved, efficiently.

The invention further relates to a continuous treatment of a fluid by chemical reaction with a treating fluid as in an in-line reactor.

The invention also relates to the efficient production of ozone by varying the oxygen feed rate, voltage, current or frequency or the ozone in oxygen concentration.

The invention also relates to the enrichment of oxygen by adding air to a high-pressure holding tank containing a liquid in which oxygen is soluble, bleeding off nitrogen-rich gas and desorbing gas from the liquid at a lower pressure.

9 Claims, 41 Drawing Figures

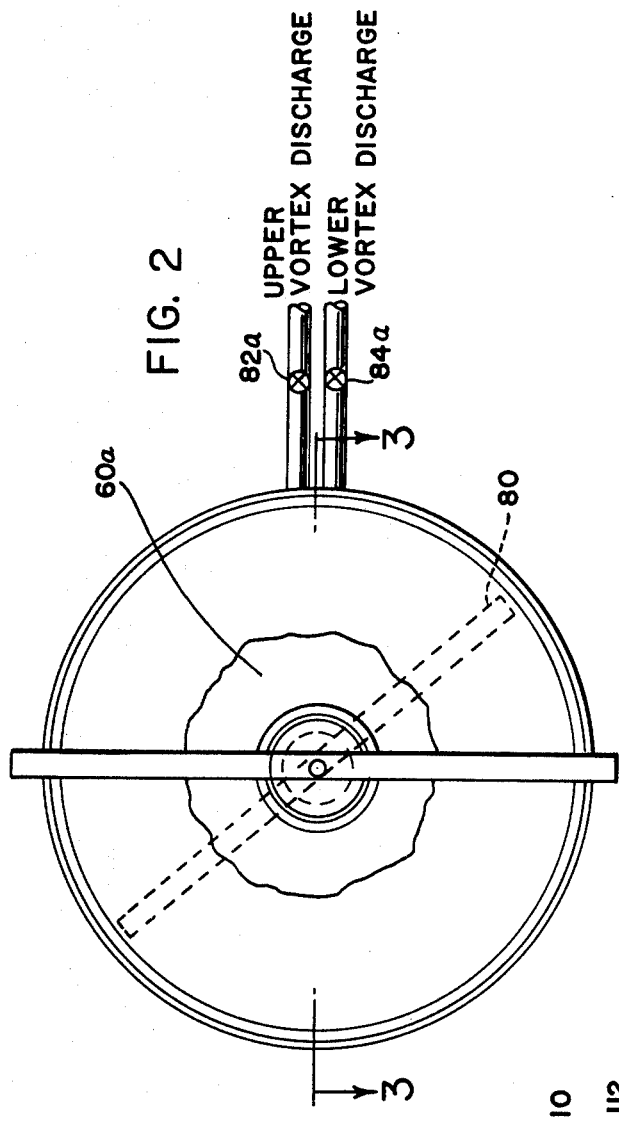
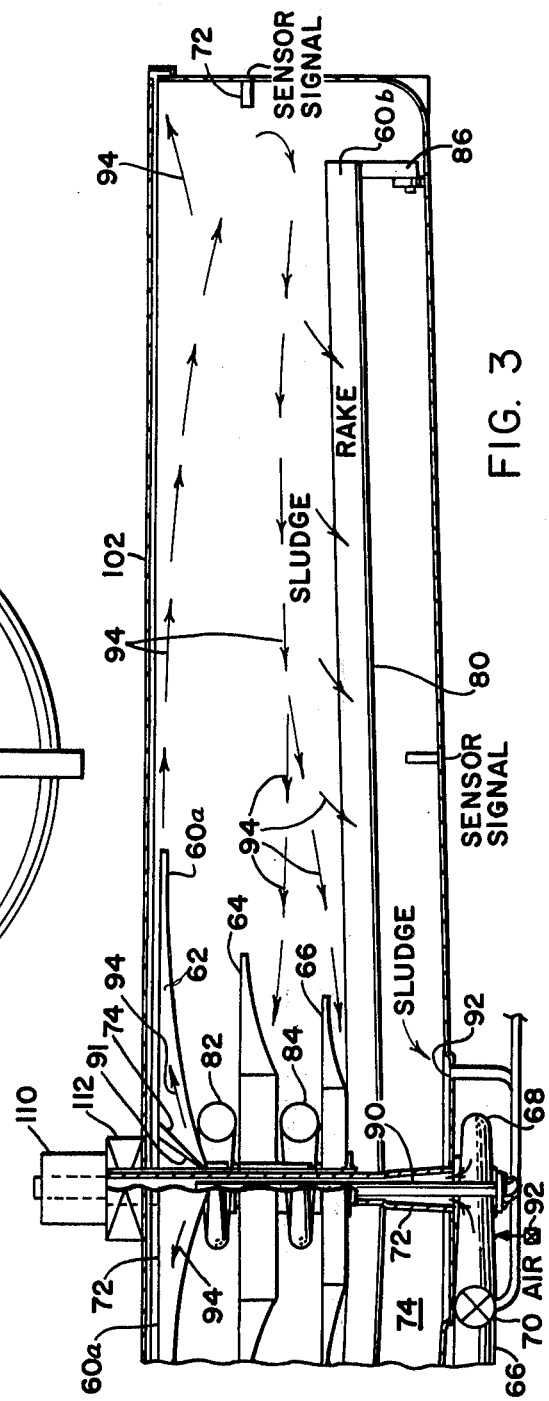

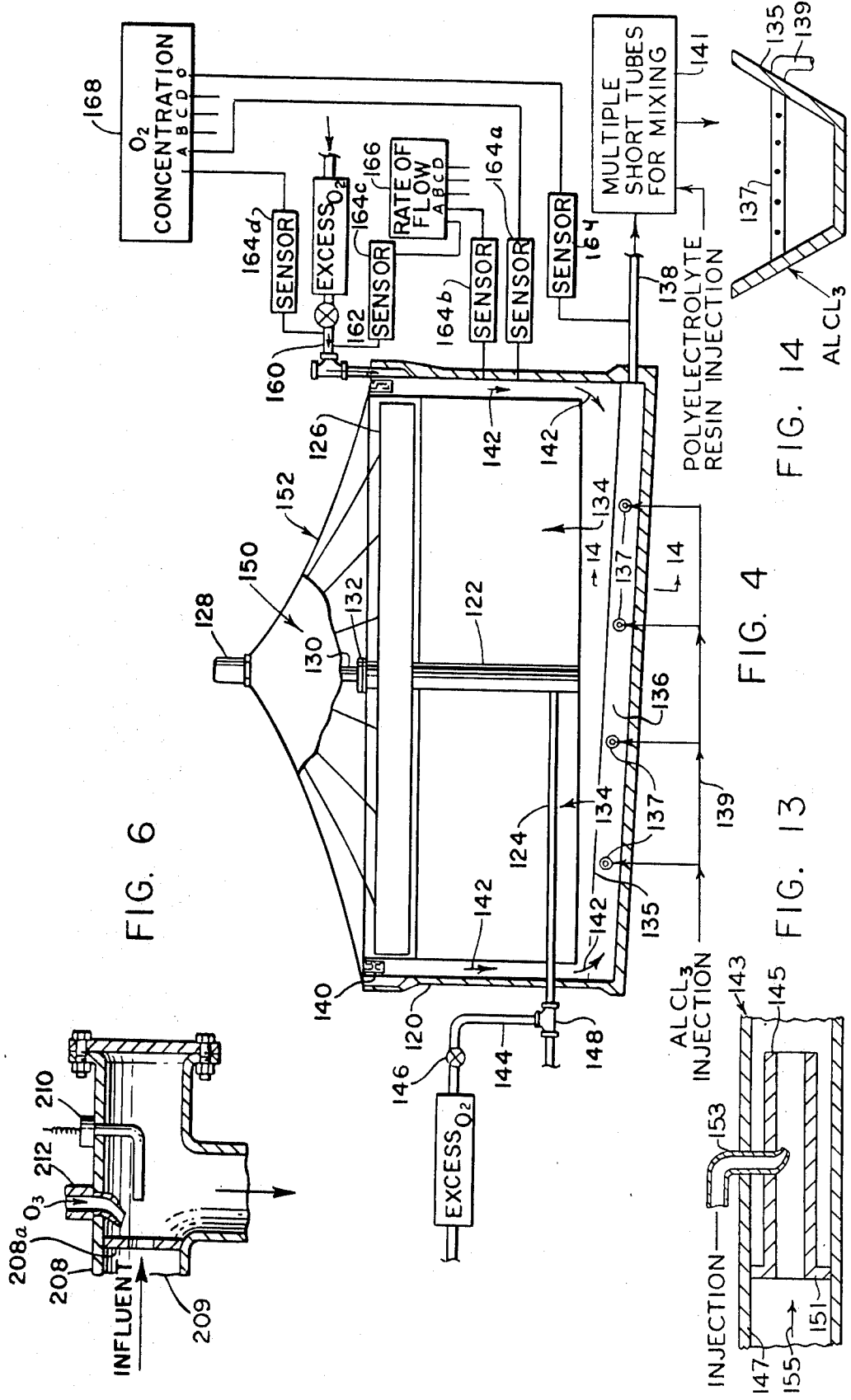

RELATION AMONG pH, TEMPERATURE AND THE EQUILIBRIUM
BETWEEN AMMONIUM AND AMMONIA.

SYSTEM FOR POLLUTION SUPPRESSION

CROSS REFERENCE

This application is a continuation-in-part of my copending U.S. Pat. application bearing Ser. No. 355,738, System for Pollution Suppression, filed Apr. 30, 1973, now in U.S. Pat. No. 3,853,764 which in turn is a continuation-in-part of my earlier application Ser. No. 100,333, filed Dec. 21, 1970, now Pat. No. 3,730,881, which in turn is a continuation-in-part of application Ser. No. 813,382, filed Feb. 28, 1969, now Pat. No. 3,549,528, issued Dec. 22, 1970, which in turn is a continuation-in-part of application Ser. No. 362,118, filed Apr. 23, 1964, and now abandoned.

BACKGROUND OF THE INVENTION

The present invention relates to a surge suppression system for preventing surge pressures or pipe hammer in liquid systems. More specifically, the present invention relates to the suppression of surge pressures or pipe hammer in liquid pumping processes.

Heretofore, various techniques have been utilized to reduce surge pressures or pipe hammer in liquid systems where commonly a pump is employed. However, most of these techniques tend to be sophisticated, uneconomical, or impractical and furthermore do not greatly reduce the surge pressure in the system. One technique utilized a fly wheel to increase the inertia of the pump motor. Another technique was based upon the use of a stand pipe which may be either of a standard or the differential type. The latter type is more common as a means for protecting against under pressures which occur incident to flow regulation in penstocks of hydraulic turbines. Another technique requires the provision of a storage tank or air vessel. A variation of this technique is a so-called one way storage tank, that is a storage tank equipped with a check valve which only permits flow during line under pressure or the like. A further variation of the storage tank technique is the utilization of a very large storage tank which may be a reservoir of water open to the earth's atmosphere.

The present invention also relates to the use of a scrubber for the general purification of a gas compound wherein the hydraulic radius of cylindrical media contained in the scrubber may be equal to the hydraulic radius of the external flow channel. More specifically, the present invention relates to a scrubber or washer wherein one or two stages may be utilized to thoroughly purify a gaseous compound through the use of high solubility fluids, oxidizing agents, or reducing agents.

Heretofore, scrubbers containing packed beds and the like have been utilized to effect fluid phase absorption. Although the removal of an undesirable compound is effected, generally the efficiency of the process is degraded by restrictions on hydraulic loading, compromises between gas and liquid flow or excessive gas-phase system pressure drop. With respect to purification, fluids have been utilized which are not highly soluble. Moreover, solids such as activated carbon have been used and these require periodical replenishment.

The present invention relates to the treatment or purification of a first fluid with a second fluid possibly a gas, with the first fluid under turbulent flow conditions in a flow conduit. More specifically, the present invention relates to the purification of a first fluid by a fluid (gas) in a flow conduit wherein turbulent flow exists to achieve thorough mixing or momentum transfer.

Heretofore, fluid phase treatment systems have been utilized in purifying fluids such as liquid or gases. In the purification of a gas by other gases, purification has largely been confined to contact chambers packed beds and the like. In such systems the treated fluid circulates through the chambers. The treating fluid achieves contact with the treated fluid in the packed bed. Where the active agent for treatment is a gas, it may be dissolved in the treating liquid. Contact is achieved as before. However, direct contact is possible between a treating gas and a treated fluid. Although some purification is obtained, the amount is less than desirable.

The present invention relates to a synergistic two stage oxidative system for disinfection of materials. More specifically, it relates to a synergistic two stage disinfection system utilizing a primary oxidizing agent in one stage and a secondary oxidizing agent in a second stage for the treatment of waste or sewage effluent.

Heretofore, in the field of disinfection, and primarily with respect to the treatment of waste or sewage effluent, oxidizing agents have been used to disinfect the effluent. However, use of the various oxidizing agents even in combination mainly gave a reduction in bacteria proportional to the amount used or to the amount of multiple compounds utilized. Moreover, the treated effluent was usually very high in ammonia which itself exerted a high demand for secondary oxidizing agent or which required extensive further treatment to remove it from the system and prevent it from being discharged into streams or waterways where it possessed a highly toxic effect upon fish and marine life. Additionally, large scale removal of the ammonia by venting to the earth's atmosphere was often undesirable due to odors and pollution problems.

The invention relates to a system for the production of effluent from a waste treatment process containing low ammonia. More particularly, the invention relates to a system, as above, wherein the secondary treatment effluent is admitted to a nitrification tower through a special distributor, aerated according to a special process, filtered through media having a special hydraulic parameters and wherein the nitrification tower is insulated.

Heretofore, various methods and procedures have been utilized to convert ammonia to ammonium nitrate in waste or sewage treatment plants. Although some of the various procedures have produced effluents with low ammonia, the processes are generally complex and costly, and do not operate consistently year-round.

Heretofore, activated sludge aeration systems have been inefficient due to poor mixing and radial concentration gradients. Moreover, flow throughout the system has generally been uneven resulting in poor treatment.

The present invention relates to continuous treatment of a fluid by a chemical reaction. Heretofore, fluids were often treated in a batch system or in other apparatus wherein inefficient mixing or contact occurred.

The present invention relates to the self-enrichment of oxygen. Heretofore, oxygen was enriched by utilizing conventional techniques such as nitrogen absorption which generally was expensive and time-consuming.

SUMMARY OF THE INVENTION

It is therefore, an object of the present invention to provide a surge suppression system wherein a gas is injected into a liquid at some point along a liquid flow system in an amount in excess of the gas saturation level of the liquid.

It is a further object of the present invention to provide a surge suppression system, as above, wherein the injection of the gas is at a high turbulence portion of flow of the liquid flow system.

It is a further object of the present invention to provide a surge suppression system, as above, wherein high turbulence causing devices are located within the liquid flow system coincident with the gas injecting points.

It is an additional object of the present invention to provide a surge suppression system, as above, wherein additional turbulence causing devices are located downstream from the gas injection-turbulence causing devices.

It is still another object of the present invention to provide a surge suppression system, as above, which is particularly suitable for utilization in liquid transmission systems.

According to the present invention, a surge suppression system for dampening surge pressures comprises a force main or transmission line carrying a liquid, injection means for introducing a gas into said main or line, and the amount of said introduced gas being in excess of that required to saturate said liquid so as to dampen surge pressures.

It is therefore, an object of the present invention to provide a scrubber for the purification of a gas through the use of fluids having preferential and high solubility, possibly causing decomposition or containing catalysts, to promote decompostion, or being heated to cause decomposition oxidizing agents or reducing agents.

It is another object of the present invention to provide a scrubber for the purification of a gas wherein the scrubber contains conventional or specialized packing media, and where hydraulic radius of the external flow channel may be equal to the hydraulic radius of the internal flow channel.

It is a further object of the invention to provide a scrubber for purifying a gas wherein the scrubber has one or two stages.

It is an additional object of the present invention to provide a scrubber for the purification of a gas, as above, wherein the particular gas is ozone in an oxygen-containing gas.

Generally, the present invention relates to a process for the purification of a gas, comprising, adding the gas to an injecting-mixing-contacting region, a scrubber containing a packed bed, adding a fluid to the scrubber selected from the class consisting of solubility agents, oxidizing agents or reducing agents, conveying said gas through said packed bed and exhausting said treated gas.

It is therefore an object of the present invention to provide a fluid phase treatment system having a turbulence causing device to maximize contact.

It is a further object of the present invention to provide a fluid phase treatment system, as above, having a downstream turbulence causing device.

It is a basic objective of the present invention to provide a fluid treatment system with a treating gas-phase fluid wherein injection-mixing and contact operations are operated under precisely controlled conditions of flow to maximize contact opportunity and to minimize the necessary concentration of treating fluid (gas) required. The key to achieving these conditions is seen to be: to inject and mix so as to suppress the concentration gradients in the axial and in the angular directions at a point where intense radial mixing is induced by a turbulence-causing device and with a high concentration gradient in the radial direction owing to the coaxial injection of treating fluid (gas) into the treated fluid (liquid or gas) recognizing that this radial concentration gradient will be attenuated downstream of the injection point within a transition length, the distance required to establish a stable velocity profile in turbulent flow, 25 to 50 diameters, and preferably at least 50 diameters, then to ensure suppression of any residual radial concentration gradient at the end of the transition length, a second turbulence causing device is introduced. This induces intense radial mixing, so suppressing any remaining radial concentration gradient. Where said second turbulence-causing device is a flat plate orifice, a further feature comes into play. That is, the flat plate orifice is one of few, if not the only turbulence-causing devices which completely removes the laminar and turbulent boundary layer from the conduit wall mixing it into the main stream of treated fluid flow. From this device, contact at maximum probability of contact between treating fluid and treated fluid may continue for a period dictated by reaction rates. Owing to suppression of concentration gradients and to the intense mixing, the reaction rate will be maximized minimizing the contact time and the concentration required for the treating fluid (gas).

Generally, the invention relates to a process for the treatment of a fluid by a treating fluid comprising, adding the fluid to a flow conduit in which the Reynolds number is at least 3,000, said flow conduit having a turbulence-causing device, adding a treating fluid to said fluid channel and exhausting a treated fluid.

It is therefore, an object of the present invention to provide a two stage oxidative system for the disinfection of material containing a distribution of ammonia and ammonium wherein a primary and a secondary oxidizing agent are utilized.

It is another object of the present invention to provide a two stage oxidative system for disinfection, as above, wherein the pH level of the material is lowered.

It is a further object of the present invention to provide a two stage oxidative system for disinfection, as above, wherein synergistic disinfection results are obtained.

It is an additional object of the present invention to provide a two stage oxidative system for disinfection, as above, for the treatment of potable or process water, waste or treated effluent.

It is still another object of the present invention to provide a two stage oxidative system for disinfection, as above, wherein the primary oxidizing agent is utilized in the first stage and the secondary oxidizing agent is utilized in the second stage.

It is a still further object of the present invention to provide a two stage oxidative system for disinfection, as above, in which the distribution of compounds of ammonia and ammonium is shifted to substantially ammonium.

The invention relates to a two stage oxidative process for disinfection of material containing a distribution of ammonia-ammonium compounds, comprising, adding a primary oxidizing agent to the material to disinfect and to reduce the pH level of the material and adding a secondary oxidizing agent to obtain low suspended solids where the ammonia-ammonium distribution is shifted toward ammonium.

It is therefore yet another object of the invention to provide a system wherein ammonia in the secondary treatment effluent of a waste treatment plant is readily oxidized to stable nitrates.

It is yet another object of this invention to produce an effluent in a waste treatment plant having low ammonia content through the utilization of a distributor, an aeration apparatus and packed bed having specific hydraulic parameters.

In general, the present invention pertains to a waste treatment system for producing a low ammonia effluent comprising a nitrification tower, said nitrification tower containing a packed bed, feeding secondary treatment effluent to said nitrification tower, said secondary treatment effluent aerated to contain dissolved oxygen, said oxygen added to said effluent through a small tube at a turbulence causing device.

The invention relates to an activated sludge aeration system in which maximum diffusion within the effluent occurs and all concentration gradients are suppressed.

In general, the present invention pertains to sludge aeration, comprising discharging air into a substantially central portion of a tank or conduit.

It is an object of the present invention to treat a fluid by chemical reaction with a treating fluid in a continuous system.

It is another object of the present invention to utilize specific chemical compounds to remove undesirable impurities from a waste treatment system.

Generally, the invention relates to a continuous process for the treatment of a fluid by a treating fluid containing chemically reactive compounds which react at specific temperatures and pressures.

It is another object of the present invention to produce ozone in a maximum concentration is ozonated gas.

It is another object of the present invention to produce ozone in a very efficient manner.

In general, the present invention pertains to the production of ozone by reducing the feed rate of oxygen, and increasing the amount of energy or power.

It is another object of the present invention to enrich oxygen in air, by compressing air in an oxygen-soluble liquid at high pressure followed by low-pressure desorption.

It is a further object of the present invention to enrich oxygen through a process wherein oxygen is more soluble in a liquid than nitrogen.

In general, the present invention pertains to the self-enrichment of oxygen by pressurizing air, feeding the air to a tank containing a liquid having a higher solubility for oxygen, and bleeding the undissolved gas off, then reducing the pressure and desorbing oxygen-enriched air.

For a better understanding of the invention reference should be had to the accompanying drawings wherein:

FIG. 2 is a plan view of an improved settling tank comprising one of the stages in the system;

FIG. 3 is a cross-sectional view of the settling tank of FIG. 2 taken on line 3—3 thereof;

FIG. 4 is a cross-sectional, schematic view of an improved trickling filter comprising a stage of the system of the invention;

FIG. 6 is an enlarged cross-sectional view of one of the flat plate orifices associated with the disinfection unit of FIG. 5 indicating the gas input and sting relationship to the orifice to obtain maximum efficiency in the introduction of the disinfecting gas and the elimination of concentration gradients;

FIG. 13 is an enlarged cross-sectional illustration of a short tube with injector to achieve good liquid, liquid, or gas-liquid mixing characteristics; and FIG. 14 is a cross-sectional illustration of the trough which traverses the floor of the trickling filter showing how a suitable sedimentation agent may be inserted into the fluid flowing therein:

Figure 1:
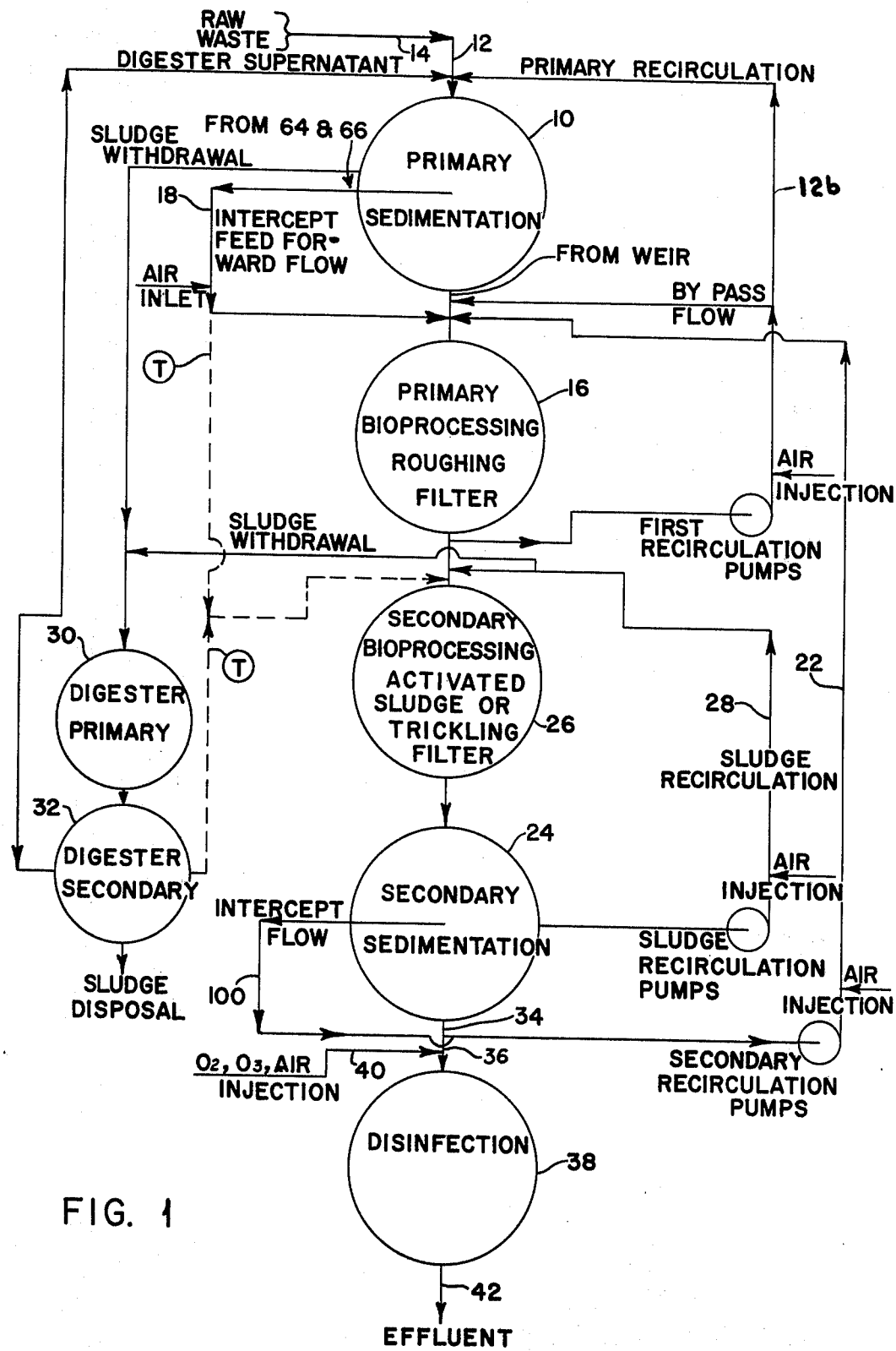
FIG. 1 is a block diagram, schematic illustration of the newly proposed system in total showing flow arrangements and the stages involved.

DEFINITION OF TERMS PSEUDOMONAS, ALCALIGENES, FLAVOBACTERIUM, MICROCOCCUS AND ENTEROBACTERIACEAE

ACTIVATED SLUDGE

All types of bacteria make up activated sludge, however, in usual operation obligate anaerobes will attenuate in number in response to the presence of air. A proteinaceous waste will favor alcaligenes, flavo bacterium and bacillus. A carbohydrate waste will proliferate pseudomonas as well.

ANAEROBIC DIGESTERS

The anaerobic digester bacteria include facultative and obligate anaerobes in active metabolism. Dormant aerobic forms may be present, such as spores of fungi. Acid formers are predominantly facultative forms although a few obligate anaerobes have metabolic end products which are acid.

Methane formers are obligate anaerobes, methanobacterium, methanosareina and methanococcus. In the metabolic pathway to subsequent end products where methane is a precursor, the pathway can be intersected owing to the implied vulnerability of methane formers to oxygen, oxygen-ozone or air. Thus, selective disinfection provides a means to inhibit methane formation or to deny a metabolic pathway to succeeding end products where methane is the necessary precursor. With denial of a pathway, an alternative pathway may be stimulated by changing environmental conditions such as by initiating aerobic activity. In this way methane would not be formed. The source material, carbon dioxide would not be reduced. This is an unnecessary step in waste treatment, since carbon dioxide is a stable end product of aerobic treatment. The hydrogen involved would not be acted upon. It is probably a constituent of formic or acetic acid. Thus, the alternative metabolic pathway opened is that for aerobic microbiological decomposition of acetic acid. Instead of the anaerobic sequence of acetic acid; acetoacetic acid to acetic acid, isopropanol to butyric acid or butanol, and unstable end products of high oxidative chemical, this invention develops the aerobic sequence. It is: acetic acid, possible pyruvic acid, oxalacetate, citrate and the citric acid (Krebs) cycle to terminal oxidation.

In a similar way, the anaerobic reduction of sulfates by the obligate anaerobe, desulfovibrio can be inhibited. Shifting to an aerobic environment denies a pathway to hydrogen sulfide. It has been found that this is readily achieved practically by aeration. Consequences include a marked reduction in objectionable odor and long persistence of aerobic action. The latter case is demonstrable by unexpectedly deferred methylene blue stability tests indicating a delayed shift to products of anaerobic metabolism.

MICROORGANISMS IN WASTE TREATMENT

Trickling Filter

Filter microorganisms reflect the facultative nature of the filter. Predominant are bacteria; aerobic, facultative and anaerobic. Obligate aerobic spore formers, bacillus are easily found in the upper, aerobic plaques. The obligate anaerobe, desulfovibrio can be found in lower levels at the plaque-stone interface where, in usual practice, DO is zero. The majority of bacteria are facultative, living aerobically until DO zeros, then anaerobically.

With reference to the drawings, FIG. 1 illustrates the waste treatment equipment, process and overall system of unit operations in which the invention operates. A primary sedimentation tank is indicated by numeral 10. The tank 10 receives comminuted raw waste including settleable solids from a line 12 issuing from a main line 14. A multiplicity of such lines 12 and subsequent operations may exist.

Two other flows are introduced from the operations which follow, constituting feedback of digester supernatant line 12a and of primary recirculation line 12b. The supernatant fraction is waste having high organic loading, relatively low flow rates, and it is resistant to aerobic processing for two reasons. First, it presents a biotal population adapted to anaerobic digestion and second, its organic composition includes the products of anaerobic metabolism.

The second fraction of flow is the primary recirculation usually occurring at rates in the range of one half to three times the raw waste rate. This recirculation flow is characterized by low organic loading and a high degree of treatability in an aerobic process. It exerts dilution effects on the raw waste which are not only marked, but which may be used in conjunction with secondary recirculation to great advantage in smoothing hydraulic and organic loading, as discussed later.

These three flows are impressed upon primary sedimentation. Regulatory authorities often stipulate hydraulic design criteria for sedimentation equipment in terms of the tank overflow rate which prevails for the composite flow. Such overflow rates may be affected by the technique illustrated in FIG. 1 of intercepting a portion of flow to be fed forward to bioprocessing indicated by numeral 16. As discussed later, in settling, using feed forward techniques, additional benefits accrue for example in organic load smoothing.

The basic flow from primary sedimentation 10 proceeds to a primary stage of bioprocessing 16. A roughing trickling filter is illustrative. There, to the sedimented basic flow, three component flows may be added. One 18 is the feed forward intercept flow noted previously. The second 20 is the bypassing fraction of primary recirculation. The third 22 is the secondary recirculation shown in FIG. 1. The existence of the feedback flows, the feedforward flow and the basic influent flow prior to bioprocessing is important. This combination provides sufficient degrees of freedom to enable independent regulation in this and succeeding operations of hydraulic and organic loading with some flexibility and without overloading primary sedimentation hydraulically. From the bioprocessing operation 16, such as the roughing filter shown, in most cases, existing plant flow proceeds to secondary sedimentation 24. In some instances, a second stage of bioprocessing 26 may be present. Usually this would be a finishing trickling filter. Rarely, but preferably, it would be an activated sludge stage of bioprocessing.

In this instance, as shown in FIG. 1, from the first stage of bioprocessing 16, the flow is split, with primary recirculation over line 12b withdrawing a fraction for feedback to an earlier stage of processing 10. The remaining fraction proceeds to the second stage of bioprocessing 26. Before introduction to bioprocessing 26, such as to the activated sludge operation, it may be mixed with recirculating activated sludge from line 28.

A remaining portion of the recirculating activated sludge is discharged for digestion with the primary sedimentation tank sludge in a primary digester 30 and secondary digester 32.

From the activated sludge operation 26, the flow proceeds to secondary sedimentation 24. The regulatory authorities stipulation on overflow rate again prevails; however, the permissible overflow rate for secondaries 24 may differ for those from primaries and may further depend upon the type of bioprocessing operation involved. The activated sludge operation is characterized by highrates of recirculation over line 22 of sedimented sludge as suggested in FIG. 1.

From the secondary sedimentation operation 24, flow may be intercepted for feedback recirculation over line 22 after partial sedimentation. A second fraction of fully sedimented flow may be returned in the basic secondary recirculation by line 34. The remaining fully sedimented flow proceeds to disinfection over line 36. In the disinfection unit 38 operation, in-line gas-liquid disinfection over line 40 by injection may precede the conventional contact chamber disinfection. The technique of gas injection is more fully defined hereinafter. The same, or complementary disinfectants may be used. For example, in-line ozonation might be followed by contact chamber chlorination in unit 38. Alternatively, chlorination may occur in both stages or only in the contact chamber with no in-line disinfection. Disinfection yields the final effluent over line 42.

It has been shown in FIG. 1 that sludge is removed from waste at successive stages of waste treatment. The sludge is stabilized, usually in two-stage anaerobic digesters 30 and 32. From the digester 32, stabilized sludge may be discharged to drying on beds, in a kiln, fluidized bed reactor may be dewatered, or on a vacuum dewatering drum. Ultimate disposition of solid products may be land fill or incineration. Disposition of digester supernatant over line 12a has been noted previously. It is this overall framework of unit operations with which the concepts proposed by the invention must be implemented. Discussion will now proceed in terms of each of the unit operations described. A later section will deal with optimum systems integration.

It should be noted however that aeration or other injections may take place at a considerable number of other points into the effluent in the system of FIG. 1. Specifically air may be injected into the digester supernatant recirculation, the raw waste input, the effluent from disinfection tank 38 and to the effluent from the secondary bioprocessing tank 26. In some instances it is desirable to inject a chlorine water solution into the effluent before disinfection to obtain break point chlorination. It should further be understood, of course, that chlorination may be used in the disinfection tank 38.

SETTLING

Settling or sedimentation is a standard unit operation in waste treatment. The effectiveness of this operation is essential because of the high concentration and broad size range of the particles present in sewage. The concentration of these particles falls in a size classification from a diameter of 0.000001 to 5.0 millimeters. This is an important characteristic, since it affects the settling velocities upon which sedimentation or clarification depend. The significant velocities range upwards from a lower limit of $10^{-9}$ millimeters per second. These velocities are achieved in clarification or settling in sewage treatment and are of primary interest owing to their broad range and extremely low magnitude.

The importance of this from a practical standpoint is in the degree of momentum exchange, vorticity, or of turbulence which will degrade settling or clarification processes. Obviously, it is any level of velocity which approaches the settling velocities described. The significant implication of this, of course, is in the fact that the kinetic energy which is present at the influent to the sedimentation chamber should be reduced to the lowest possible practical level. Anything which tends to increase the kinetic energy of the influent jet will degrade the performance of the clarification or sedimentation process. Recirculation has such effects, however, it has offsetting compensatory advantages in diluting the organic load to be handled. In contrast, high velocity, or excessive momentum exchange impose a penalty without an offsetting advantage.

For an understanding of the basic construction of the settling tanks 10 and 24, reference should be had to FIGS. 2 and 3 of the drawings. The specific effects of the modifications of the settling chamber are as follows:

a. To control the fluid path prior to free settling.

b. To reduce the velocity and turbulence level at the influent to the region of free settling.

c. To increase the settling flow path length and the time available for settling.

d. To increase the functional effectiveness of settling.

e. To reduce, by forward-feed techniques, the hydraulic load on the settling tank and particularly to reduce its overflow rate.

f. To introduce a further degree of freedom in hydraulic and organic load existing in present feedback recirculation.

The apparatus making up the improved settling tank of the invention may be fitted in a conventional circular settling tank. Its distinguishing element is a rotationally-transformed radial or hyperboloidal-envelope diffuser. The diffuser may incorporate spiral vanes indicated generally by numeral 60a. The rotational transformation is through 7° or less to ensure minimum probability of flow separation at the channel boundary.

This is a critical factor in the three-dimensional diffuser design owing to the flow deceleration which is induced.

Smaller, but similar, three-dimensional spiral-shaped collectors 62 and 64 may be used at one or more centrally located annular collection points to provide upper effluent collection and/or intermediate effluent collection, respectively. There, flow is accelerating and boundary layer separation is much less significant.

In a conventional sedimentation tank, influent and effluent flow may be distinguished. Previously and in existing art, these have not been considered in terms of optimum overall circulation. The case is illustrated by the conventional circular plan view sedimentation tank. In it, flow is usually upward in a central influent well. At the upper limit of this central well, flow is predominantly radially outward with both relatively high turbulence and velocity.

In such a tank, the predominantly radially directed surface jet induces a circulation in the central region. In consequence, a sustained toroidal vortex circulation develops there. This means that the intended settling flow is perturbed. It is degraded functionally by rotational mixing usually imposed mechanically and gravitationally by earth rotation. The result is settling circulation.

Concurrently, the outflow is predominantly a peripheral, radial flow. It induces a similar toroidal vortex at the overflow weir. This toroid exhibits comparably lower velocities, lower turbulence and a much larger diameter. This circulation is of lower energy level corresponding to the reduced overflow velocity. The direction, or sense of rotation, in the second toroidal vortex is the same as in the influent circulation. This means that at an intermediate radial position in the tank, the two toroidal vortices interact with opposing local vertical components of flow. This interaction manifests itself by momentum exchange which degrades settling.

To attempt sedimentation under imposed conditions antagonistic to the functional objective seems ill advised. A desirable situation is to recognize that an overall circulation must be considered and that the direct and induced flow described must be complementary to the necessary circulation. This is the general objective of the settling tank of the invention.

This is possible under the case for circular plan view sedimentation if a single toroidal vortex may be induced under controlled conditions of overall circulation. Preferably, this should be done in such a way as to enhance the primary sedimentation flow and, if necessary, to yield a secondary effluent having predictable sedimentation.

This may be accomplished by insertion and use of the central collector 62 described, positioned beneath the central influent jet 82. Its flow is radially inward below the influent jet boundary surface. Owing to the presence of an hyperboloidal diffuser surface or vane 60a, the central effluent can operate with minimum degradation of the influent jet. Moreover, it operates upon a well-sedimented, low turbulence fraction of sedimentation tank contents. These conditions lend themselves to the production of a consistent, predictable fraction of partially sedimented flow which reduces the tank overflow rate.

On the inlet to the intermediate level collector in the sedimentation tanks it may have the hyperboloidal profile of the upper diffuser vane 60a since it is less critical in that flow is accelerating. On the system optimization, more fully explained hereinafter, it appears that it is essential to control the process, operated manually or automatically to accomplish the desired flows stated above. Representative means 70 for manual or automatic regulation are provided. Implementation of sensors 72 for flow are an obvious requirement. One way to determine organic load is to measure it by lab techniques on typical days. The average hourly results could be charted. Control of means 70 could be based on the expectation that this would occur. It is also possible to use inferential measurements of load, such as those based on light transmission or spectral absorption in narrow bands of wave length. Probably rapid, intense oxidation could be accelerated sufficiently to give real time data on BOD.

Then, system control for manual or for automatic conditions may be based on an expected program (historical findings) modified by real time measurements of the actual hydraulic and organic loading conditions with sensors 72, for example. This is a standard control technique in any servo system. The essential feature is to program, establish errors, impose an error correction and instrument the result to make sure the error was corrected. If not, a secondary correction may be introduced.

FLOTATION SEPARATION

This concept may be introduced with a secondary functional effect of the central influent well 90. The affect is applicable where flotation, particularly for oil and grease separation is of concern. These conditions occur in primary sedimentation. To accomplish this result, presaturation of the influent with air as through injector 92 at pressure levels exceeding that at discharge is desirable. Outgassing of the excess air as the system is depressurized enables enhanced flotation in the influent well 90 of the primary sedimentation tank. This integrates equipment and methods of sedimentation improvement with those of gas-liquid mixing, both as set forth in the present invention.

The collectors 62 and 64 remove two cuts of flow from the settling tank and from the sedimentation effluent discharges from the overflow weir central collectors. The upper cut is taken from 6 inches to 30 inches below the liquid line which normally runs closely adjacent the top edge of the tank. The lower cut is taken from 36 to 48 inches below such liquid line. The major portion of intercepted flow amounting to approximately 2/3 the total is taken from the upper effluent collector 62. The lower collector 64 removes the remaining flow except for sludge and its entrained liquid. Normally, it will be necessary for the effluent picked up by collector 64 to pass to another processing operation for further treatment. From the sedimentation operation, the basic flow sheet leads to bioprocessing. The effluent flow in the sedimentation tank is indicated by the arrows 94. The effluent enters line 66 through valve 70, up the influent well 90, driven by pump 68, and discharged from the top 91 of well 90, through screen 74 and into a spiral discharge by vanes 60a adjacent the top surface of the effluent level. The diffuser vanes 60a are driven in a slow rotary motion by motor 110 which is supported on a bridge truss 112 which extends over the top of the tank. The motor 110 is of variable speed and appropriately driven for the correct latitude of the tank since the vortex rotational speed for the effluent actually depends on latitude.

Flow is controlled by valves 82a and 84a, as best seen in FIG. 2 of the drawings, and at the inlet by valve 70. The effect of the valves in inducing turbulence at the diffuser effluent is suppressed by means of the hole size in the screens 73 and 74. It should be understood, however, that similar operations occur at greatly reduced velocities in tank 24 which might cause the elimination of an upper effluent collector 64.

At the end of the vanes of diffuser 60a, the effluent is directed in close to a tangential direction in the horizontal plane. The vertical component of velocity is extremely low owing to deceleration in the diffuser. In view of the low velocity, it is clear that sedimentation will occur in the diffuser. Provision is made for continuous sludge removal. This is done by operating the diffuser at close to zero buoyancy, a mechanical technique readily within the skill of one knowledgeable in the art.

The diffuser vane 60a is rotated at very slow speed, perhaps one revolution per hour. These serve as collectors of finely classified material. The sludge is removed through pipe 93 in the central section and out through the tank bottom, as well as through a sludge trough 95 and sludge conduit (not shown) 94.

It has been anticipated that the extreme care taken in settling tank design may be upset by two factors. One is wind induced surface cooling and superimposed horizontal flow. The second is the density anomaly in water which occurs at 4° C. The latter factor may have severe consequences in terms of vertical circulation. In addition, there is the usual effect of temperature variation on the density of water. For these reasons, the invention may use an air enclosure over the tank, as indicated by cover 102. This cover 102 mitigates the effects of wind and temperature.

At least one of the central effluent volutes 82 or 84 will be vertically adjustable, and probably both, so as to ensure positioning thereof in accordance with the flow demands through the tank to achieve optimum performance.

To ensure light gravitational loading, the rotating diffuser 80 will be supported peripherally at each sector by wheel 80b running at fixed load on the bottom. The wheel load control may be set with a suitable type of spring loaded washers.

The secondary settling tank 26 receives effluent from the lower cut of the first tank 10. Its primary sedimentation in its diffuser will pass particulates of 200 mesh or finer into the tank proper. The described cut for particulates greater in size than those passing a 200 mesh screen will be deposited and removed from the sedimentation which occurs in the diffuser 80 beneath the false bottom, as in the flow path 78. Non-filterable and colloidal particles are unaffected.

In regard to flow, in the secondary settling tank 26, the hydraulic effluent is one-third the plant effluent. The tank proper is intended to separate, in two cuts, the coarsest effluent particles to those of less than 200 mesh. The upper cut of sedimented flow, two-thirds the effluent is removed. The lower cut of flow removes one-third the tank effluent, or about one-ninth of the initially impressed hydraulic load on the plant. Only this fraction of flow proceeds to the trickling filter or other BOD reduction process.

ROUGHING TRICKLING FILTER

The following discussion will involve the operation of the first bioprocessing stage, a roughing filter 36 commonly known as a trickling filter. No discussion will be given to the aeration stage 34 impressed upon the influent, as this is covered in my copending applications. Bioprocessing operations are responsible for the principal reduction in BOD. The elementary theory of a trickling filter is that an extended surface media is provided usually using rock fill, about 6 feet deep, on which a microbial plaque develops under pulsed film flow of waste liquor containing some dissolved oxygen, DO. The plaque is comprised of a media surface-contacting an anaerobic substrate immediately adjacent to which anaerobic and facultative microbiological forms predominate. Above this layer, aerobic forms may be present. This implies a source of oxygen. Ostensibly this is provided by an induced, vertical, natural-convective air circulation occurring parallel or countercurrent to the pulsed liquid flow.

A fundamental limitation of conventional trickling filtration is the indifferent oxygenation occurring therein. In consequence, aerobic processes essential to bioprocessing are inhibited. Diminished capacity in organic load reduction results. A further limitation aggravates this problem. It arises since, to allow some air circulation, hydraulic loading is restricted. This reduces the capacity of the filter and concurrently the effectiveness of waste treatment. This is so because the hydraulic compromise restricts recirculation flow to the filter, a prime factor in giving significant BOD reduction.

To indicate the deficiencies of free convective air flow in trickling filters, it is of interest to refer to operating conditions inducing such flow. A basic equation for air velocity as taken from "Water & Waste Water Engineering," Fair, et al, John Wiley & Sons, Vol 2, pp. 35–13, is:

$$V a. = 0.135 \Delta T - 0.46.$$

where
 V a is the air velocity in feet per minute and,
 $\Delta T$ is the temperature difference between the air and the waste water, °F.

The waste water-air temperature difference seldom exceeds 25° F. For temperature differences of 10°, 3.4°, and −3.3° F, for example, V a is respectively +1.0, 0 and −1.0 fpm. The positive sign denotes downward flow. Recognizing the usual filter is a stone-packed bed about six feet deep, in no case is a realistic air velocity indicated. Forced air circulation has been examined with little promise. Packed bed resistance to air flow can be high, especially with superimposed hydraulic flows.

The limitations of aeration and compromises in hydraulic loading are unnecessary. The ideal remedy is use of an effective air-liquid mixing system in the trickling filter influent line. This will provide DO in the range of 7 to 8 ppm, all year round and at any hydraulic loading. The particularly undesirable restriction of recirculation may be relaxed. This simple remedy will enable hydraulic loading in the range from 1,000 to 3,000 or more gallons per square foot per day. Typical current practice is at about one-fifth to the lower range of these levels. The hydraulic flows are restricted to these levels to defer blocking of air flow which has been necessary to provide for aeration. Having eliminated compromises dictacted by inadequacies of aeration in conventional art a simple change enables full exploitation of the revised trickling filter process. This change is one of media, from a size range of coarse rock to a reduced size range of smaller media. The change in media is primarily responsive to considerations of hydrodynamic flow. This is so because compromises relating to air flow are unnecessary. Inasmuch as the change is in hydrodynamic characteristics, it is conventional to describe the desired media properties in terms of hydrodynamic parameters.

The parameters of interest are the friction factor, the Reynolds number and the roughness coefficient. The media size factor applies as an equivalent diameter. The characteristic length of flow path is the bed depth, which is conventional. The relation among these factors is of the form:

$$f = \frac{a}{N_R} + b$$

where
 $f$ is the friction factor
 $a$ is a constant
 $N_R$ is the Reynolds number and
 $b$ is the bed media roughness factor. The defining equations of interest are:

$$f = \frac{2g \, De \, \Delta \, \rho}{\rho \, V^2}, \text{ and}$$

$$N_R = \frac{De \, V \, \rho}{\mu}$$

It suffices to define the media in terms of its equivalent diameter and roughness factor. Flow conditions are stipulated by the functional relationship between friction factor, Reynolds number and bed depth.

The typical parameters for the new media are in the range tabulated next for a hydrodynamic element. This arises in relation to an influent waste with high DO and with no aeration required in the filter proper.

I have calculated parameters for a substitute plastic media, for example PVC. The media is extruded tubing. It is assembled in an equilateral triangular grid to maximize the surface installed per unit volume.

The tubes are spaced to ensure balanced flow inside the vertically positioned tubes and outside the tubes. This requires that the hydraulic radius for the internal and external passage be equal.

Figure 12:
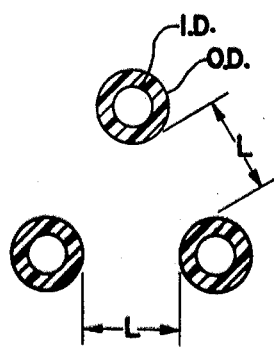
FIG. 12 is a cross-sectional end illustration of the tubular media which can be used in the trickling filter.

A typical result appears as follows as is illustrated in FIG. 12.
 OD = 0.84 inch
 ID = 0.74 inch
 L = Grid spacing 1.16 inch
 The hydraulic radius of a channel is:
 Area of section/perimeter
 The section described above exhibits an area for biological plaques of about 40 ft²/ft³. Conventional rock has less than 40% of this specific surface.

The lengths may be full depth in a continuous section, from 6 feet to 30 feet; however, shorter lengths stacked to the total depth have advantages. The basic advantage is that the laminar boundary layer of liquid on the plaque starts at zero thickness and builds up. A length which is short compared to the length required to fully develop a stable laminar boundary layer keeps the dissolved oxygen supply to the plaque readily available. The diffusion gradient is increased in two ways. First the concentration is sustained at high levels, second the boundary layer thickness is decreased.

The length for a fully developed boundary layer in laminar flow is as great as twenty feet for water flowing in tubes of about ¾ inch diameter in the limiting transitional range of Reynolds number, about 3,000. Expressing distance in terms of diameter, the transition length is about 1/10 to 1/20 the Reynolds number.

The flow in the spaced tubular media at the limiting laminar Reynolds number may be estimated. It is 22 million gallons/day per 1000 square feet of media surface. Hydraulic loading rates are conventionally less than 1 million gallons/day per 1000 square feet. Thus, planned high hydraulic loading is feasible with this media.

Moreover, the uncompromised rates enable much high organic loading. Instead of present upper limits of less than 70 pounds of BOD per day on each thousand cubic feet of media, three to four times this load appears feasible. The high organic or nitrogenous loading only becomes practicable with preaeration which permits much higher hydraulic loading. All three variables, DO, hydraulic loading and organic loading, interact. Because of this, only a mutually compatible solution is feasible. In this instance the equipment and method involved bring into action the integrated benefit of efficient gas-liquid exchange and bioprocessing operations.

The structural details of the improved trickling filter utilizing a media 134 described hereinbefore are illustrated in FIG. 4 of the drawings which shows that a circularly-shaped housing 120 centrally mounts a carrying post 122 which receives the liquid effluent through pipe 124 carrying the aerated effluent discharge from the settling tanks. The post 122 rotatably carries a distributor arm 126 which is rotatably driven hydraulically by reaction or by a motor 128 connected thereto through shaft 130 and double flanged coupling 132. The liquid influent through pipe 124 passes up through center post 122 and actually distributes in a sprinkled relationship out the distributor arm as it is rotated by motor 128, all in substantially the conventional manner heretofore utilized in trickling filters.

In the particular construction utilized, some type of wire mesh reinforced concrete wall or the like to form a large circular bed indicated generally by numeral 134 is filled with loosely packed stones or the specialized materials defined above that offer promise of providing greater surface areas per unit volume. As long as the problems of constrained liquid flow and undue gas-phase flow restrictions are considered, extended surface packing can be used effectively in this configuration. In any event, the liquid sent out by distributor arm 126 drips down through the packed beds 134 into the open base.

In addition, the invention may contemplate utilizing a plurality of forced air blowers, each indicated generally by numeral 140 positioned around the periphery of the tank 120 and adapted to drive air in the direction indicated by the arrows 142. Since one of the purposes of such a trickling filter to reduce BOD is to ensure more oxygen is present to cause oxidation of the liquid effluent, such forced air which must necessarily pass up through the bed in a reverse flow to the liquid flow therethrough, forced circulation can supply oxygen to sustain aerobic metabolism. Further, in order to provide the increased oxygen recovered may be atmosphere, excess oxygen actually injected through air injecting-mixing element for fluid-fluid as described herein into the effluent through pipe 144 into some type of turbulent mixing chamber 148, as appropriately controlled valve 146. Also, in order to make the filter operate on nearly 100% humidity in the atmosphere, some type of roof covering indicated generally by numeral 150 may be provided that is supported by a catenary cable arrangement 152. Hence, the trickling filter may utilize 100% relative humidity, forced air circulation, and an oxygen-enriched atmosphere because of the oxygen injection into the effluent. The increase in plant capacity and reduction in BOD is readily measurable with this setup.

In this aerobic process it is also apparent that the design features described for improved sedimentation means may enchance the waste treatment system overall. In other words, oxygen injection into the sludge recirculation unit 22 is contemplated so as to greatly enhance the operating capabilities of that unit to produce treatable safe sludge concentrations.

The invention might also incorporate the addition of excess oxygen directly into the humidified atmosphere through a pipe 160 as controlled by valve 162. The control of the amount of oxygen entering might appropriately be provided by a suitable sensor 164 associated with the effluent output pipe 138 and operating in conjunction with a rate of flow instrument indicated by block 166, and an oxygen concentration unit indicated by block 168. Appropriate sensors 164a–d are associated with the rate of flow instrument 166 and oxygen concentration unit 168 to complete this setup, so as to control the actual amount of oxygen flow through pipe 160 for the most economical operation of the system.

BIOPROCESSING SECOND STAGE ACTIVATED SLUDGE

An activated sludge operation may be the sole bioprocessing unit or a secondary element in a two-stage bioprocessing operation. It is unlikely to find activated sludge as the initial element of a two-stage bioprocessing operation. This is in recognition of the sensitivity of activated sludge operations to fluctuating influent hydraulic or organic loads. Although not present typical practice, activated sludge operations may be adapted to handle fluctuating hydraulic and organic plant influent loads. This may be done by providing sufficient flexibility in circulation to accommodate independent balancing of hydraulic and organic load incident upon the activated sludge operation. This has been referred to before and will be discussed under system integration.

Regardless of the mode of application of the activated sludge operation, a predictable requirement exists for aeration. Observed aeration corresponds to from 500 to 700 cubic feet of air per pound of BOD removed. The implied oxygen requirement is from 7.5 to 10.5 pounds of oxygen per pound of BOD removed. An equivalent quantity may be derived from surface aeration. Thus, the overall conventional requirement for oxygen is from 15 to 21 pounds of oxygen per pound of BOD removed. Recalling that BOD equates one to one with oxygen demand by definition, the implication is that oxygenation by aeration using conventional techniques is not remarkable for efficiency. This inference remains valid even allowing for available internal sources of oxygen as from the biological reduction of nitrates. This finding is to be expected since aeration efficiencies are often quoted in the range of 2 to 10%. It should be understood that the quoted values pertain to aeration of liquid having an initial DO of zero. This yields the highest possible efficiency. A more realistic efficiency is that for a DO in the range of 2 ppm.

The practical solution to the aeration question in activated sludge operations is set forth in my copending application identified above and hereinafter. The technique and equipment derives oxygen mixing efficiencies considerably in excess of 50%. Use of such aeration means in the present activated sludge operation is visualized. This will reduce air compressor capacity required by as much as an order of magnitude and will cut drive power requirements to less than ½ usual values. The treatment method may be any of the seven basic methods utilized in activated sludge operations. What is important is the integration of efficient gas-liquid mixing techniques with this stage of bioprocessing.

From the activated sludge operation, treated waste discharges to secondary sedimentation. Where the activated sludge operation is not preceded by sedimentation, the following sedimentation operation might properly be termed final sedimentation,

SECONDARY SEDIMENTATION

In the case illustrated in FIG. 1, the processed waste from the activated sludge operation is discharged in a central influent well, as for primary sedimentation. Here, however, excess aeration to achieve degassing and enhanced flotation of grease and/or sludge is unnecessary. With this exception, the equipment and process operation may be as described for primary sedimentation previously. As might be expected, exceptions occur in the preferred disposition of effluent from secondary sedimentation.

For example, sedimented secondary sludge is removed conventionally and returned to the influent of the activated sludge operation or to the plant head box. Some of this flow may be diverted so that excess sludge is fed to the primary digester. Clarified effluent is discharged to disinfection with diversion of necessary quantities to secondary recirculation. To achieve desired balance between the hydraulic and organic loading imposed by secondary recirculation, intercepted partially sedimented flow may be incorporated in the secondary recirculation. This is shown in FIG. 1.

In the effluent from secondary sedimentation destined for disinfection, disinfection is initiated at the line exiting the secondaries. This technique exploits highly efficient gas-liquid mixing techniques described in the above-identified copending application. This disinfectant proposed is ozone-oxygen enriched air for several reasons. First, this disinfectant is effective with the organic loads present in brief contact times. Second, this disinfectant is potentiated, i.e., it acts synergistically in the presence of a secondary oxidizing system. The secondary oxidizing system may be ferric chloride added in the secondary sedimentation to promote clarification, or it may be the standard chlorination additions. In either case, ozone-oxygen enriched air reduces the ultimate chlorine demand and ensures an effluent exhibiting relatively lower chlorine residuals with high dissolved oxygen. This disinfection characteristics of ozone-oxygen and potentiating effects of aluminum chloride or of ferric chloride are noted. The standard technique adds ferric chloride or aluminum chloride to secondary sedimentation system so it cooperates synergistically with ozone added in disinfection.

DISINFECTION TREATMENT

According to the concepts of the present invention, a highly effective system for disinfection is provided using to a two stage oxidative system on material usually containing a distribution of compounds of ammonia and ammonium and is particularly suitable for the treatment of waste or sewage effluent. A primary oxidizing agent is utilized to chemically oxidize and clarify the material as well as preferably to lower the pH level and a second oxidizing agent is utilized to disinfect. Although the oxidizing agents may be any conventional compounds which are conventional disinfectants, preferred compounds for the treatment of waste or sewage effluent comprise aluminum chloride, or ferric chloride as the primary oxidizing agent and chlorine, chlorine dioxide, ozone either preferably in oxygen air or oxygen enriched or air, or sodium hypochlorite as the secondary oxidizing agents. It has been found that synergistic results of oxidative disinfection are achieved by the two stage treating system of the present invention wherein the primary disinfecting agent is utilized in the first stage and the secondary oxidizing agent is utilized in the second stage. Preferably, a fair amount of oxidizing agent is added to the first stage and a small amount of secondary oxidizing agent need be added to produce an extremely low bacteria count.

Preferably, the two-stage oxidative disinfection system is suitable for the treatment of water, waste or sewage treatment plant effluent. The primary oxidizing agent may be added to the final clarifier influent or effluent and the secondary oxidizing agent may be added to the disinfecting contact tank influent of a conventional waste treatment facility or to the waste treatment facility as set forth hereinabove. In the treatment of waste and sewage effluent, a fecal coliform bacteria count of less than 10 per 100 milliliters of treated effluent may be readily and easily obtained.

Figure 18:
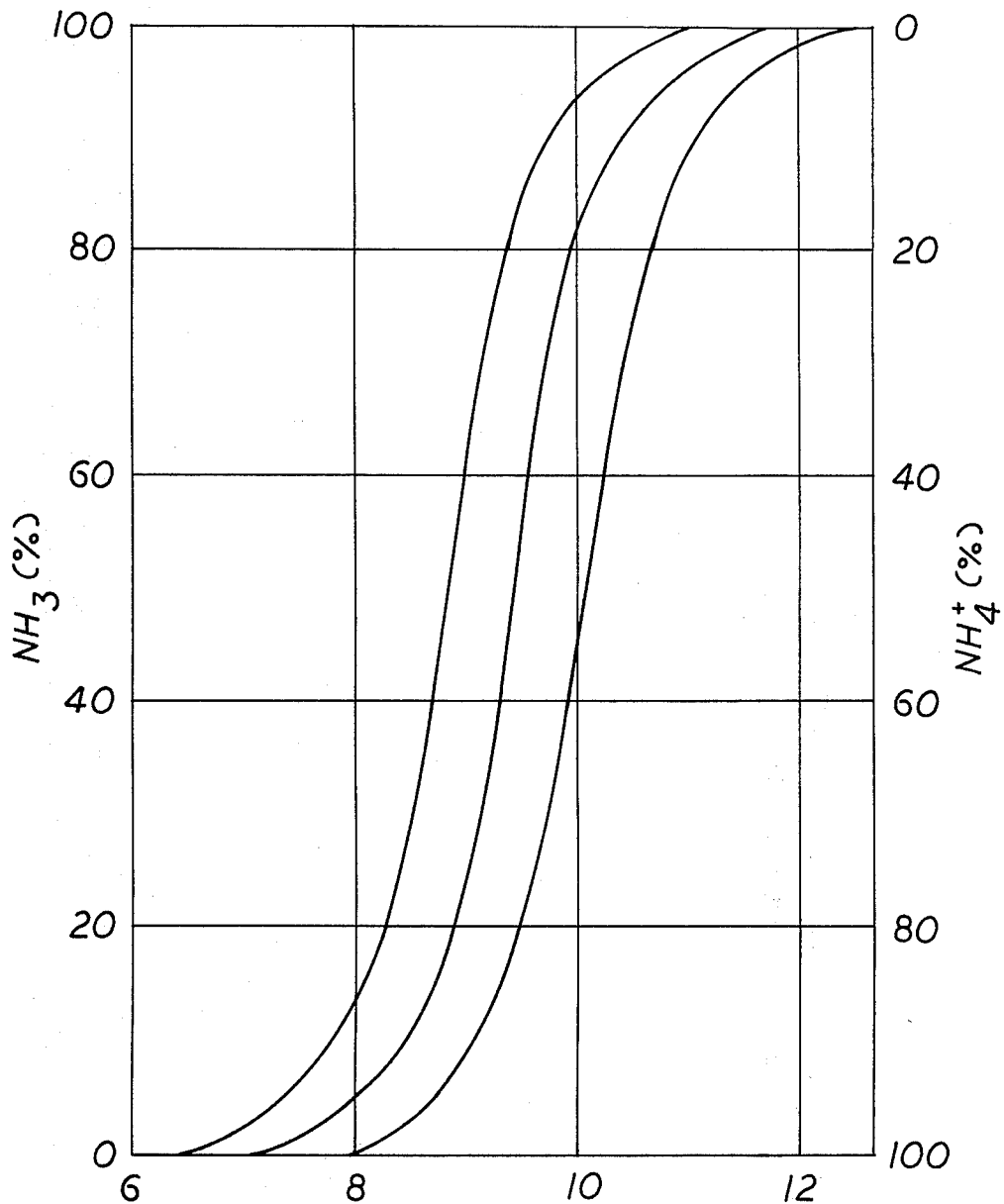
FIG. 18 is a graph setting forth the relationship between temperatures, pH and the equilibrium between ammonium and ammonia.

The use of a preferred primary oxidizing agent as set forth above has been found to reduce the pH level. Preferably, an amount of primary oxidizing agent is utilized so that the pH of the effluent coming from the final clarifier is at a level of 7 or less with approximately 6.7 to about 6.8 being desirable. As apparent from FIG. 18, such a pH level at ambient temperatures will shift the ammonia-ammonium equilibrium to ammonium. In fact, nearly all of the equilibrium will be shifted to the ammonium compound, that is in excess of approximately 97 and at times even 100%. Of course, if a higher pH is utilized, smaller amounts of ammonium will be present. Generally any reduction in pH is desirable in that it reduces the amount of ammonia. Thus pH of 8 and less at ambient temperature may be suitable. The significance of the reduction of ammonia is that ammonium chloride or other ammonium compounds or complexes often exert virtually no oxidative demands when exposed to bacterial metabolism in the presence of oxygen below a pH of 7.0. Hence, in the tretment of waste and sewage effluent, the nitrogen oxidative demand which is exerted will be virtually reduced to 0. In contrast, ammonia exhibits a substantial oxidative demand amounting to approximately 4 ½ times the ammonia nitrogen concentration. Thus, in conventional waste treatment systems wherein concentration of the ammonia in the effluent discharged from the secondary clarifier which is in the range of 30 parts per million will require approximately 135 or 145 parts per million of oxygen demand. Not only does such a demand exert toxic effects upon a stream or body of water, if and when it is exerted, it also directly affects the dissolved oxygen concentration of the stream.

Concerning the toxicity effects upon a stream, it is well known that ammonia in water can be toxic to fish at 4 to 5 parts per million concentration. On the other hand, ammonium compounds are not toxic and as previously noted, frequently, exert no oxidative demand. Additionally, ammonium compounds act as inhibitors of the exertion of nitrogenous metabolism by bacterial forms present. Thus, in addition to the synergistic reduction of bacterial in disinfection, the shift in equilibrium in the distribution of ammonia-ammonium to ammonium compounds produces highly practical results. This is especially so in view of the regulatory agencies requiring reduction of nitrogenous biochemical oxygen demand, and minimum practical chlorine concentrations in effluent consistent with disinfection and recent awareness of the role of chlorine in carcinogen formation.

In a conventional or typical sewage treatment plant handling primarily residential waste, an amount of primary oxidizing agent of approximately 85 parts per million has been found adequate to produce a pH range of about 6.6 to 6.7 and to effectively promote sedimentation in the final clarifier. A minimum amount of at least 50 parts per million has been found to be desirable. Additionally, the amount of suspended solids in such a sedimentation stage is generally very low. Such suspended solids are precipitated in the secondary clarifier and thereby removed from the treated effluent stream.

It has been established that in the above described two-stage oxidative disinfection system wherein relatively high amounts of primary oxidizing agents have been utilized, that very low amounts of secondary oxidizing agents are required. For example, where ozone is utilized, the concentration may be as low as 0.7 parts per million whereas for chlorine, the concentration may be as low as 4 to 5 parts per million to accomplish the aforementioned disinfecting objectives, that is, a fecal coliform count of two or less per 100 ml. As a practical matter, with conventional mixing, the ozone feed concentration will generally be higher than the minimum amount due to the fact of inefficient mixing in the secondary clarifier of the oxidizing salt such as aluminum chloride or ferric chloride. Generally a maximum of 10 parts per million will be sufficient to disinfect. Maximum efficiency mixing can be derived from the use of high turbulence causing devices in a flow channel such as the utilization of flat plate orifices as above described and utilizing specific arrangements as set forth in FIGS. 6, 13 and 15, of the present application as well as those taught in U.S. Pat. Nos. 3,730,881 and 3,805,481.

Considering now an actual operating system according to the present application, a first stage of an oxidative disinfection or treatment with ferric chloride or aluminum chloride was accomplished by adding 85 parts per million feed. The fecal coliform count leaving the first stage was quantitatively established at $10^9/100$ milliliters and thus, the first stage by itself, does not, disinfect. The fecal coliform count leaving the second stage of the oxidative disinfection system with a chlorine feed rate of 4 parts per million was established to be 0. Moreover, the degree of terminal sterilization effected is confirmed by Agar Cultures at 37° C which indicate no growth.

Further, in the utilization of a two-stage disinfection system as described above, it was found that a fair size chloride ferric dose added to the first stage to promote sedimentation followed by a dose of 6.6 parts per million of ozone in oxygen in a second stage can, in as little as 8 seconds, raise the dissolved oxygen concentration to 37 parts per million. Such a sample was immediately sealed after oxidative disinfection and remeasured five days later. A dissolved oxygen concentration of 31 parts per million was found. The difference of 6 relates to the fact that the metabolic activity of the surviving forms of bacteria present had been virtually completely inhibited. This was accomplished by direct disinfection and by oxidative near kill which effected the viability of the organisms and their ability to propagate. Thus, the maintenance of the dissolved oxygen concentration of from 37 ppm to 31 ppm after five days implies a close approach terminal disinfection.

OPTIMUM SYSTEM

System optimization in waste treatment is usually discussed in terms of a fictitious constant load. Optimization as conventionally used does not usually refer to meeting effluent quality standards at a minimum combined capital and operating cost.

CHARACTERISTIC LOAD

The characteristic waste load on a plant is a combined hydraulic and organic load. It is not constant during the day. It is likely to be repetitive day to day, excepting holidays and weekends. Rain and seasonal effects impose long period changes in load.

Weekday loads may be approximated reasonably well with a geometric series of few terms. It is not unusual to find that the range in load may be as great as ± 75% of the average load. Somewhat in contrast with this fluctuating load, effluent criteria on quality typically require that a prescribed maximum never be exceeded. Practically, this means that plant regulation is aimed at achieving better quality with 0.95 or 0.99 probability despite variations in influent loud. How much better the quality goal should be is a critical economic consideration.

Obviously, with a fixed output specification and a highly variable input, no fixed settings in process regulation will aproach compliance and economy. An obvious approach is to accumulate mixed waste for extended times and then to treat a continuous sample at the average daily rate. This would require large holding tanks and problems of settling, septicity, odor and cost arise.

Despite these problems, great advantage accrues from the constant hydraulic and organic loading obtainable by optimum system utilization. The basic advantage is in simplicity of controlled regulation of the plant process. The plant is essentially a servo system. To get a fixed output at a prescribed level, it would obviously be easier to find the fixed process settings to meet this level where the input is also fixed. With the actual input, the best process design and control is then a sophisticated problem. Although, this problem is a basic one economically, it has not yet received the attention it deserves.

In the equipment and process implementation of this concept, a dual attack on the design and control problem is proposed. Basic to the attack is provision of adequate flexibility in process control to enable a close approach to uniform hourly hydraulic and organic loading over a typical operating day. This minimizes the magnitude and effect of imposed fluctuations in hydraulic and organic load. The second basic element of approach is to provide process control to operate on the suppressed load variations to achieve the desired level of effluent quality continuously. This yields the optimum system in terms of minimized total cost to derive continuously the acceptable quality of effluent. Calculated performance, process conditions and basic factors in total cost have been determined and are set forth in more detail hereinafter.

With respect to the system optimization the ideal solution requires excessive sedimentation tank capacities, both in the primary and the secondary tanks. The practical answer is to compromise the flow.

Figure 11:
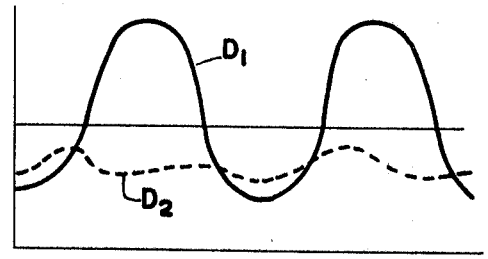
FIG. 11 is a graphic illustration of Case D also defined in the specification.

The example A, shows that for an arbitrarily variant inflow rate and organic load concentration, it is possible to achieve a process influent having a constant inflow rate and a constant organic load concentration. The demonstrated condition pertains to the sedimentation tank influent in each example. Thereafter in the process, the hydraulic load varies with time, but the organic load concentration is held constant. The compromise condition allows a variation in hydraulic and in organic load to the sedimentation tank. Lower total influent rates to primary sedimentation result. The design condition is imposed next in the process. This means that the interval a-b over which integrals are considered is short or that point values are used. In addition, a simplified on-off control to approximate the exact solution is shown. This substitutes a rectangular region for integration in place of the region beneath a trigonometric curve, or an actual plot of station load, hydraulic and organic. Case D shows that where $Q_1 = 3.0$ for the 24 hour day rate, a total flow of 3.8 provides an optimum system flow. The flow condition yields a close approximation to constant organic load concentration to the trickling filter, as shown in the graph of FIG. 11. In an activated sludge process, the concentration could be held constant by return-sludge rate controls. Hydraulic loads would vary in either illustration of the solid graph D1, or dotted graph D2 of Case D.

Figure 8:
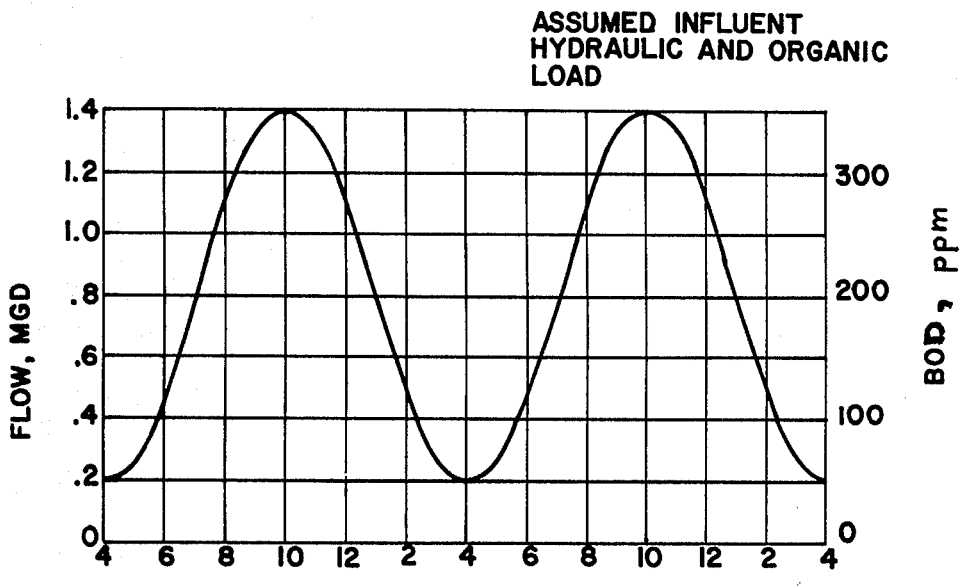
FIG. 8 is a graphic illustration of the assumed influent hydraulic and organic load.
Figure 9:
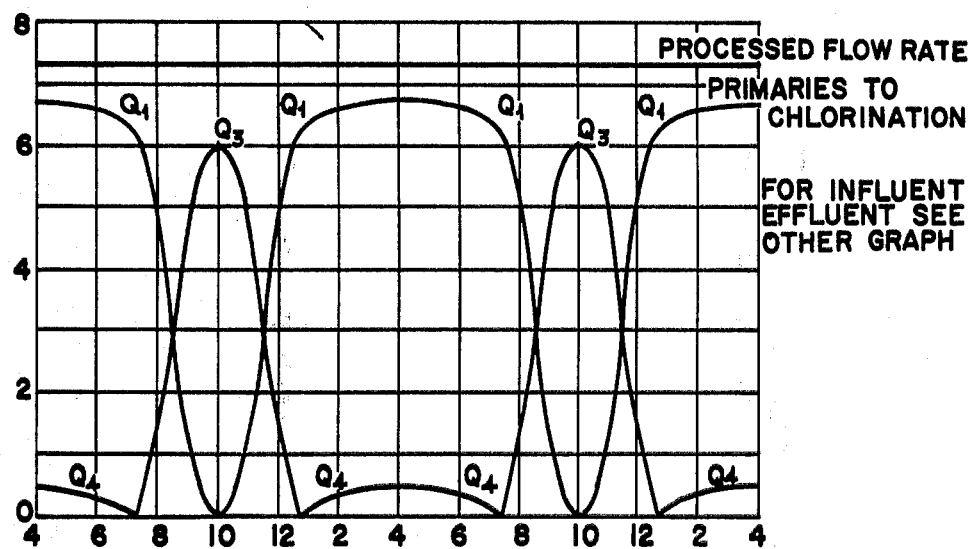
FIG. 9 is a graphic illustration of the optimum system process flow rates for Case A and a variable influent for Case B with constant process flow with a fixed effluent quality and fixed hydraulic/organic load.
Figure 10:
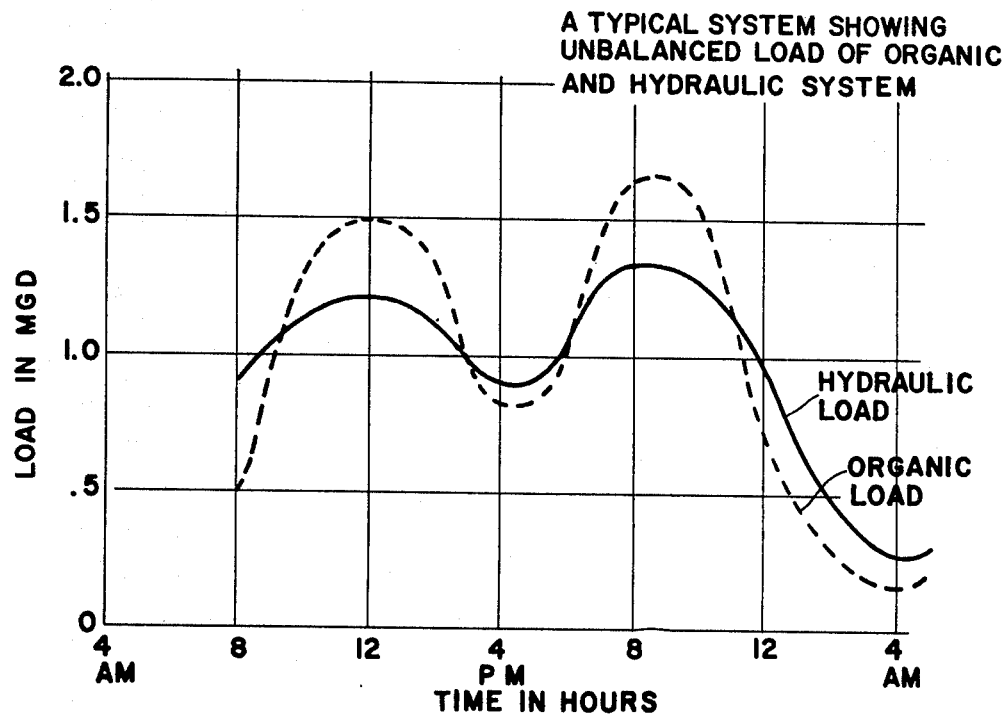
FIG. 10 is a graphic illustration of the flow load system optimization in Cases A, B and C defined in the specification.

Case A — Schematic flow sheet shown in FIG. 10 illustrates conditions for uniform hydraulic and organic load with an arbitrary variable incident load. The figures shown between sections in FIG. 8 are the BOD of the treated waste in ppm. Case A, also shown by the graphs of FIGS. 8 and 9, uses process control of flow in $Q_1$, $Q_3$, $Q_4$ and $Q_5$. $Q_2$ may be held at zero.

Maximum Load — $Q = 1.4$ MGD . $B = 350$ ppm.

Secondary recirculation for 10:00 AM/PM load.

$$(BOD) \; 83 \cdot [\, Q + Q_3 \,] = 1.4 \times 350 + Q_3 \cdot 20 \qquad \text{I.}$$

$$Q_3 = \frac{1.4 [\, 35 \mp 83 \,]}{83 - 20} = \frac{1.4 \cdot 267}{63} = 5.93$$

Recirculation ratio; $R = \dfrac{5.93 - 1.4}{1.4} = 3.24$

Flow to primary: 5.93 MGD rate

Secondary recirculation for 8:00 and 12:00 AM/PM load.

$83 \times 5.93 = 1.1 \times 275 + 20\ Q_3 = 58\ [483 - Q_3]\ Q_3$
$= 107.5/38 = 2.83\ Q_1 = 4.83 - Q_3 - 2.0$ Secondary recirculation, other flows, 7:00 and 1:00 AM/PM. This is the average load condition.

$83 . 5.93 = 0.8 \times 200 + 20\ Q_3 + 58\ [5.13 - Q_3]$ and, if $Q_3$ is zero:

$5.93 \times 83 = 0.8 \times 200 + 20\ Q_3 + 58\ [5.13 - Q_3]\ 492$
$+ 34 = 20\ Q_3 - 58\ Q_3\ Q_3 = -34/38 =$ approximately $-1.0$

II. Case for 8:00 and 12:00 AM/PM $83 \times 7.33 = 1.1 \times 275 + 20\ Q_3 = 58\ [6.23 - Q_3]\ 610$
$= 20\ Q_3 - 58\ Q_3 = -38\ Q_3\ Q_3 = 54/38 = 1.42\ Q_1$
$= 6.23 - 1.42 = 4.81$

III. Case for 7:00 and 1:00 AM/PM Average load $83 \times 7.33 = 0.8 \times 200 + 20\ Q_3 + 58\ [6.53 - Q_3]\ 610$
$- 160 - 379 = 71 = -38\ Q_3$, but for $Q_3 = 0\ 71 =$
$58\ Q_1, Q_1 - 71/58 = 1.23$ flow check $6.53\ B + 0.8$
$\times 200 = 83 \times 7.33\ 6.53\ B = 450\ B = 450/6.53 = 69$ flow must shift to $Q_1 + Q_4$ continued percent solids primary 3% and percent solids secondary 6% Primary sludge 3% at 7.33 MGD = 0.22 MGD BOD = 83 − 58 approximately Average supplied = approximately 2500.

IV. $83 . 7.33 = 0.8 \times 200 + 600\ Q_4 + 58\ [6.53 - Q_4]$
$+ 71 = 600\ Q_4\ 58\ Q_4$ $Q_4 = 71/542 = 0.131$ MGD
then
$Q_1 = 6.40$ MGD

V. Conditions at 6:00 and 2:00 AM/PM $83 . 7.33 = 0.5 + 125 + 600\ Q_4 + 58\ [6.83 - Q_4]$ $151 = 600\ Q_4 - 58\ Q_4$
$Q_4 = .279$ MGD
$Q_1 = 6.55$ MGD

VI. Conditions at 5:00 and 3:00 AM/PM.

$83 . 7.33 = 28.70 + 600\ Q_4 + 58\ [7.05 - Q_4]\ 181 = 600\ Q_4 - 58\ Q_4$ $Q_4 = .33$ MGD
$Q_1 = 6.72$ MGD

VII. Conditions at 4:30 and 3:30 AM/PM $83 . 7.33 = 0.22 \times 55 + 2500 . Q_5 + 58\ [7.11 - Q_5]$ $Q_5 = 0.089$ MGD,
or
showing alternative for secondary sludge method of digestes supernatant $83 . 7.33 - 0.22 \times 55 + 600\ Q_4 + 58\ [7.11 - Q_4]\ 186$
$- Q_4\ [600 - 58\ ]$ $Q_4 - 0.343$ MGD
$Q_1 - 6.77$ MGD
Conditions at 9:00 and 11:00 AM/PM $83 . 7.33 = 1.32 \times 327 + 20\ Q_3 + 58\ [6.0 - Q_3]$

VIII. Conditions at 8:30 and 11:30 AM/PM $83 . 7.33 - 1.22 \times 305 + 20\ Q_3 + 58\ [6.11 - Q_3]$ $Q_1 = 3.11;\ Q_3 = 3.0$

IX. Condition at 9:00 and 11:00 AM/PM $83 . 7.33 = 1.32 \times 330 + 20\ Q_3 + 58\ [6.0 - Q_3]$
$-174. = -38\ Q_3;$ $Q_3 = 4.58;\ Q_1 = 1.42$

X. Condition at 9:30 and 10:30 AM/PM $83 . 7.33 = 1.38 \times 345 + 20\ Q_3 + 58\ [5.95 - Q_3]$
$-211. = -38\ Q_3;\ Q_3 = 5.55$ $Q_1 = 0.4$ Case A Pump Capacities — Flow around primary sedimentation equals gravity. Flow around trickling filter equals zero. Flow around secondary sedimentation equals $Q_1 - Q_4 = 6.4$. Flow from secondary sludge equals 0.4. Then, 0.400,000./24 60 = 278 GPM. Use 300. GPM 2:150 GPM Secondary 6.4/1440 − 4,450.; Use 4:1200 GPM.

| Equipment sizing Case A | |
|---|---|
| Primaries: 4 | 60' Diameter |
| Secondaries 4 | 60' Diameter |
| Trickling Filter 2 | 75' Diameter |

System Characteristics — Large sedimentation requirements. Moderate Pumping requirements. Conservative bioprocessing requirements. Fixed effluent BOD to chlorination of 20 ppm, with influent BOD's from 50 to 350. BOD reduction is from 94.3 to 43%.

A second case may be examined. It reduces primary and secondary sedimentation requirements, as it appears that a practical variation from the illustrative Case A which has been described above, is based on a compromise at the peak flow condition occurring at 10:00 AM/PM. The compromise is to accept a system condition as at 9:00 or 11:00 AM/PM for the hydraulic load. An organic load in ppm can be held constant. Instead of the ideal situation, holding the hydraulic load constant, 24 hours per day, we hold the system hydraulic load at the 9–11 level. Then, in the interval 9–11 AM/PM, i.e., twice a day, for 2 hours, a hydraulic overload is allowed. This only affects the primary and secondary sedimentation tanks, and not seriously, in comparison with the cost reduction enabled. Except in the interval 9–11, the system hydraulic and organic load may be held constant.

Of course, other compromise expedients may be selected. For example, the interval might be 8–12. For the three cases, A, 9–10, 8–12, the relative flows are 1.4, 1.32 and 1.1. Most state laws require that sedimentation tanks be proportioned to accommodate specified overflow rates expressed as MGD per unit of surface area. Thus, reducing from 1.4 to 1.1 means that the required area reduction is 3/1.4 which is roughly proportional to the cost reduction.

The all or none flows are typical of practical manual control. Valve settings may be made and left for an appreciable time. This type of control is also amenable to automatic regulation of the plant. Simple time controls can accomplish this type of regulation.

The previous discussion involved more sophisticated controls typical of usual servo control system. The foregoing conditions are a convenience in calculation. The calculations set forth above and the graphs of FIGS. 8 through 11 are based on controls of definite integrals. The integrals concerned are of the form:

$Q = \int_a^b q \, c \, dt$, where:
Q is an organic load
a, b are time limits for the load increment considered
q is a flow rate
C is a loading concentration, and
dt is differential time.

In effect, control is based on manipulation of definite integrals to approximate organic load concentrations at indicated points in the overall process. A particular case is shown at the influent to the sedimentation tank where the organic load and the hydraulic load are held at constant values. The effect on increased overflow rates at the sedimentation tank has been noted above.

To relax the overflow rates at primary sedimentation, it is feasible to impose the condition for constant hydraulic and organic load at bioprocessing. For a trickling filter or an activated sludge unit operation, it is desirable to hold the hydraulic and also the organic load constant. This is particularly so of activated sludge unit operations. To illustrate this condition, a limited number of calculations as set forth above are indicated to show a typical solution.

DISINFECTION SYSTEM

Figure 5:
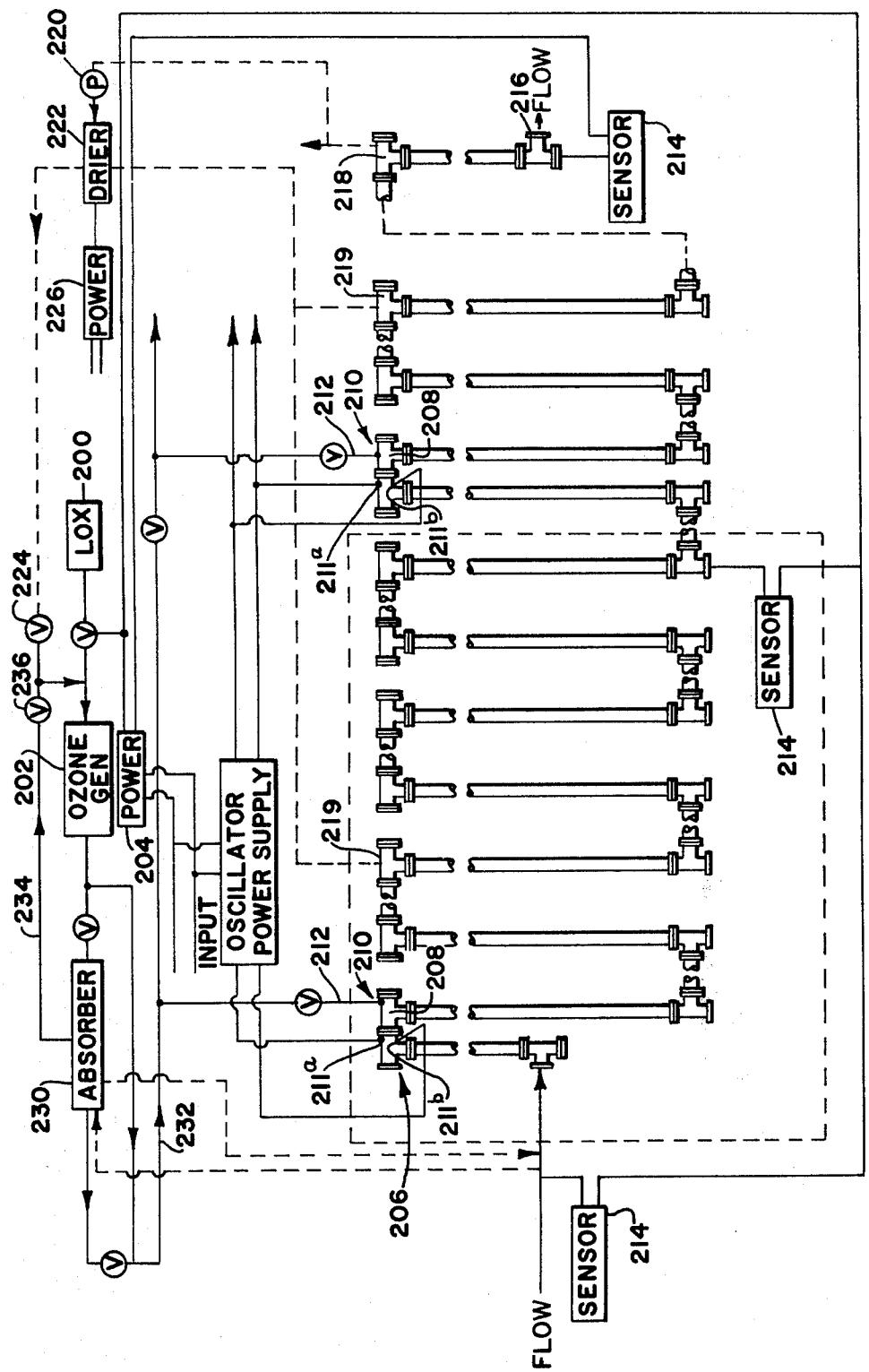
FIG. 5 is a schematic flow diagram of the disinfectant unit indicating the operation under a hydraulic gradient with sensors and gas input control.
Figure 7:
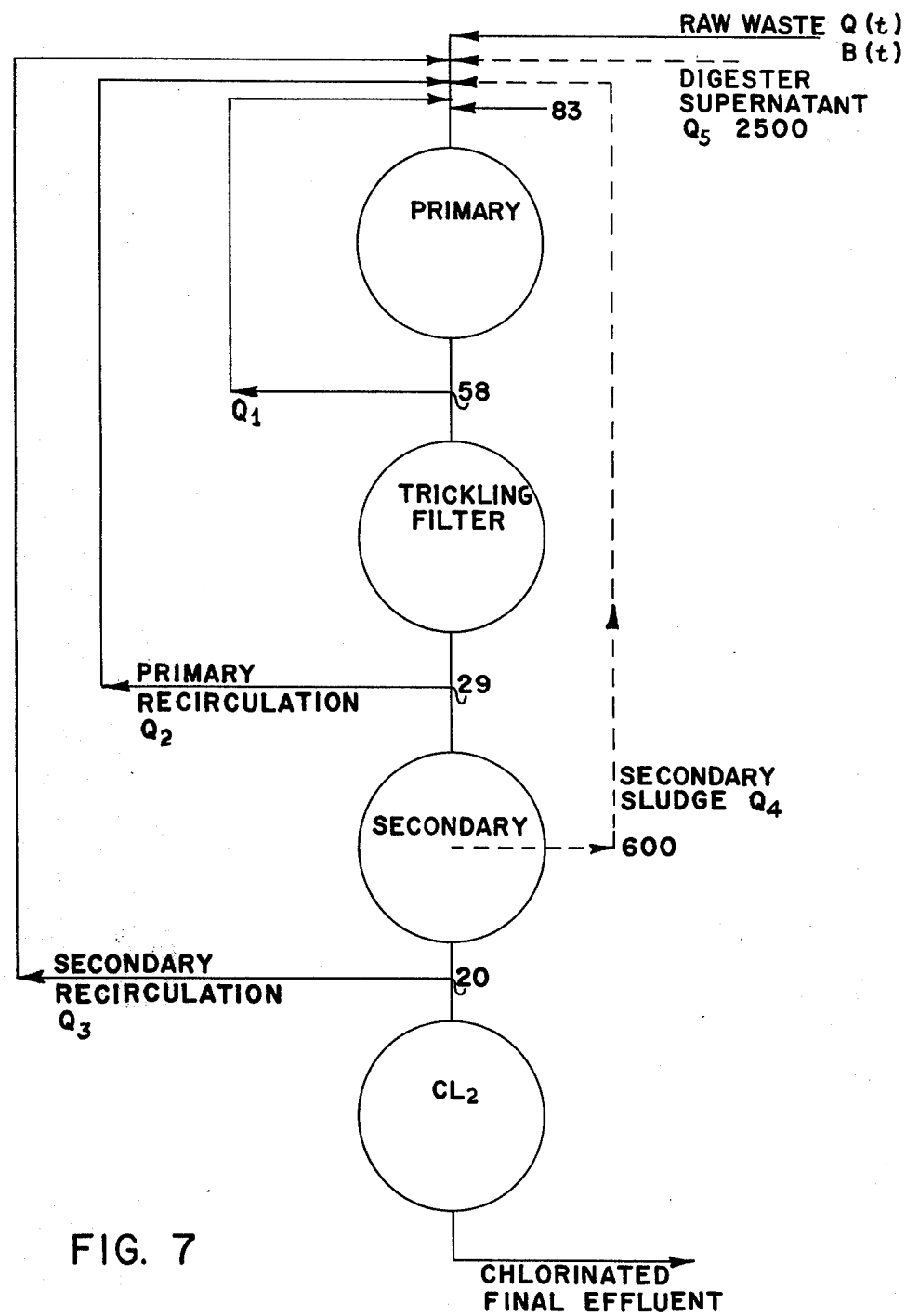
FIG. 7 is a flow diagram of a modified basic system illustrating system optimization and flow control.

The disinfection system indicated in FIG. 5 of the drawings in a gas-liquid mixing system operating under a hydraulic pressure gradient. It is comprised of a liquid oxygen supply 200, an ozone source or generator 202, an oscillator power supply 204, and a process flow line indicated generally by numeral 206. The line 206 operates in the regime of turbulent flow, at or above a Reynolds number of 3,000. High momentum exchange mixing elements are carried in at least certain of the T-shaped flanges 208. These mixing elements are normally flat plate orifices 208a which induce intense mixing sufficient to minimize radial concentration gradients in the processed liquid effluent entering the flow line 206 at 209. The mixing elements 208a may be followed by sting-type cantilevers 210 driven by a tunable source 211 excited at or near their natural frequency. These may be positioned in relation to the gas injecting means to further enhance the momentum exchange in primary regard to minimizing concentration gradients occurring in the angular direction in addition to the radial gradient suppression induced by the basic mixing element, the flat plate orifice. In addition, the primary objective is to have the stings 210 provide mechanical disruptive forces on flocs, plaques, or agglomerates which may be present in the processed liquid effluent. The objective of imposing disruptive forces is to reduce the size and to extend the available surface for disinfection on such flocs, plaques or agglomerates.

The orifices 208a in the T's 208 are provided at the flange joints as a matter of convenience. The orifice diameter ration to the pipe diameter is typically equal to or greater than 0.7. In the T's 208 securing the orifices 208a, two other elements are mounted. One is an $O_3-O_2$ injector 212. The injector 212 is introduced in a fitting ideally centrally allowing axial positioning which extends through the orifice preferably to or slightly past the vena contracta formed by the flow through the orifice. Optimal injection is found to be with minimum concentration gradient in the flow direction. This is most conveniently obtained by making the fluid flow rate steady over short or longer intervals of time and by similar proportional control of gas flow. The sting 210 is the second element introduced with similar provision for axial position and scaling as the injector 212.

The $O_3 - O_2$ injection occurs at approximately 5% or less concentration by weight of ozone in oxygen. For generalized disinfection, it is introduced in amounts greater than 0.5 milligrams of ozone per liter of fluid. The injected concentration will attenuate in the flow line. Two factors cause the attenuation. One is the decomposition rate for $O_3$ in water leading to $O_2$. The second attenuating factor is the oxidation load of the material contained in the processed liquid. In the typical waste, this is comprised of organic materials incompletely oxidized to stable forms. These materials in conjunction with oxidizable inorganic constituents comprise the BOD load of waste.

Recognizing that $O_3$ attenuation which will occur, it may be necessary to utilize sequential injection. This aspect is shown in FIG. 5. FIG. 5 also indicates a series of test points in the flow line between injection points for the $O_3$ which include sensors 214 that act to control a power supply 204 to the generator 202. These sensors 214 are useful to assess quantitatively the $O_3$ concentration. For a given Reynolds number, these data provide information on time and position. This information is essential for design of the flow system and for determining the optimum $O_3$ injection flow rate. For generalized disinfection, it is important to the invention that the injection rate and interval be such that the attenuated $O_3$ concentration exceeds 0.5 milligrams of ozone per liter of effluent at all points in the system in which generalized disinfection is to occur. In contrast, specialized disinfection as of obligate anaerobic forms of bacteria may be sustained with air or oxygen containing only trace quantities of ozone as usually found in concentrations of 0.01 ppm or less. This process and implementation is detailed in my above identified copending application.

From the above, the purpose for sequential injection is clear. The number of points, or the distance or time in the flow line will depend upon the impressed oxidation load and particulate size of this load. It is anticipated that in normally operating systems, the time for processing will not exceed 8 minutes. It should be understood that the piping system indicated in FIG. 5 will normally extend in a vertical direction wherein the entrance at 209 and discharge at 216 are at comparable horizontal locations so that in essence a hydraulic gradient is present when considering the system as a whole. The relative vertical location of these points is immaterial to the effectiveness of the disinfection system.

The actual construction of a T 208 showing the flat plate orifice 208a, the centrally positioned $O_2 - O_3$ injector 212, and the oscillating sting 210 in greater detail is shown in FIG. 6 of the drawings.

The invention also contemplates that excess oxygen can be picked off the piping system at point 218 by a suitable pump 220 and sent into a drier 222 for transfer therefrom through a control valve 224 into the supply line from the liquid oxygen source 200 to the ozone generator 202. A suitable power supply 226 activates the drier 222.

An absorber indicated by block 230 might be included to receive the output from generator 202 before passing the ozone concentrated fluid into a supply line 232 so as to remove all excess oxygen with the excess oxygen fed back over line 234 and through valve 236 to the supply to generator 202. The absorber 230 is optional as the $O_3 - O_2$ concentration can pass directly through line 238.

In some instances, it might also be desirable to have processed liquid effluent entering at point 209 into the piping system 206 pass through some type of deaerator or absorber to degas or desorb $O_2$ out of the effluent since you can't get new $O_3$ into the fluid in an $O_2$ carrier gas if the fluid is saturated with $O_2$. A dotted line 240 illustrates this optional arrangement.

It should be understood that the system described hereinabove calls for the preferred implementation utilizing a liquid oxygen feed. An oxygen enriched air feed to ozonation may be used with or without recycling and oxygen make up to be described hereinafter. Either of these may be refined incorporating recycled, dried, and recovered oxygen. However, continuous recirculation may not be feasible, and in this case it is apparent that there exists a desirable bleed-feed rate for the oxygen supply. The rate should satisfy the DO requirements on effluent and the argon dilution problem whereby ozonation efficiency may degrade with increasing concentrations of contaminant gases. Also. The installed capacity of the bleedfeed $O_2$ supply should be at the average anticipated $O_3 - O_2$ demand. This will minimize the capital investment required.

With reference to the passage of the effluent through deaerator or absorber 230, it has been found that 7 to 40 ppm $O_2$ may be recovered from the effluent before discharge for use in the oxygen-enriched process in the waste treatment system. Techniques other than deaeration or desorbing that might be utilized would either be heating or cavitation, where the cavitation might involve ultrasonic excitation as set forth in my above identified co-pending application.

It should also be noted that the entire disinfection process set forth preferably used oxygen enriched air, not air, thus minimizing the impact of high nitrogen concentration on ozonator efficiency. In using oxygen enriched air or oxygen as described, a number of significant improvements naturally follow. For straight oxygen it is a known physical fact that the potential solubility of oxygen in water is five to six times as great if introduced in equilibrium from oxygen enabling a higher concentration of ozone to be injected while less oxygen is required. The elimination of oxides of nitrogen contributes to safety and air pollution control. Further, the availability of oxygen for recycling and for process enhancement reduces the oxygen expense by an order of magnitude or more while the process enhancement is increased as pointed out above.

Also, recovered oxygen may be utilized in the trickling filter or activated sludge operation by oxygen-effluent injection, or by enrichment with this oxygen of a basic air-waste injection means. In this way a trickling filter bed should maintain aerobic metabolic rates at maximum quantitative levels throughout its entire depth. A similar effect on the activated sludge operation is possible. The effect on increased BOD reduction is apparent.

FORCE MAIN INJECTION

The aeration for force main injection has been practiced in the range of 4 parts of air in from 10,000 to 100,000 parts of fluid by weight. The volume concentration need not exceed 50% of air in liquid. For force main injection, useful results may be realized to much lower levels, perhaps as low as 1–5% by volume. Wet well aeration may be effective at appreciably lower feed rates. The limitation for this case depends on degassing at the impeller eye, leading to eventual loss of pump prime. This problem is also more fully covered in my above-identified co-pending application.

The saturation levels for aeration of water at atmospheric pressure are near 20–30 parts per million by weight of this, one-third is oxygen, two-thirds nitrogen. For waste, slightly lower saturation limits may be expected in view of the presence of additional contaminating gases and dissolved materials, i.e. for aeration. In the oxygenation case, water saturation levels are in the range 40 to 50 ppm, of oxygen, by weight. For ozonation, with oxygen as the carrier, at 6% ozone in oxygen, by weight, the saturation range corresponds to ozone in liquid concentrations of about 2.5 ppm. by weight. The foregoing ranges may be useful as depicting preferred ranges of gas concentration.

As is known, force mains operate intermittently according to the influent rate to the wet well and the level settings used to control the pumps. When the pumps shut down, a pressure wave travels through the system, is reflected, returns, and oscillates periodically, ultimately damping out. The pressure fluctuations occur below and above the static pressure level in the line. The pressure differences may compare with the dynamic-static pressure difference or they may exceed this difference. Such pressure waves are referred to as water hammer. Air present in force main incident to aeration to control septicity affects these pressure waves. The presence of air reduces the pressure differences, it reduces the velocity of the pressure waves in the force main, from one end to the other and the air damps out the pressure oscillation rapidly in a reduced number of cycles, all in comparison to the force main response to pump shut down without air injection to the force main. All these results are beneficial and are a bonus accruing from the practice of air injection to force mains. Thus, it is apparent that force main used for waste, water, or liquid generally, such as oil, may benefit from aeration, or inert gas injection as with engine or boiler exhaust gas, nitrogen or carbon dioxide. Preferred gases are those which are not unduly reactive and which exhibit low saturation levels in the liquid transported. This reduces the gas compressor capacity required to inject an excess of gas beyond the saturation concentration. The beneficial results on pressure reduction occur predominantly from undissolved gas.

SURGE SUPPRESSION

Pipe hammer or surge suppression can be abated or greatly reduced by injecting an amount of gas in excess of the saturation level of a gas in a liquid. Desirably, a large excess is preferred such as from about 5 to 10 times the saturation level. Generally, an excess of twice the saturated level is necessary to produce suitable results. Preferably, to ensure that the saturation level is reached, the gas is injected at a highly turbulent region of flow in a liquid piping system such as a main or transmission line as exemplified by a pipe. Generally, any type of device for causing high turbulence may be utilized. A specific example of such a device is illustrated by FIG. 6, previously described. Although FIG. 6 shows a Tee with one portion blocked off, the same apparatus may exist in an elbow or the like or desirably in a straight flow pipe. According to the present invention, gas injector means 212 injects a gas into the central portion of the flow pipe of a force main or transmission line within or slightly past the high turbulence regime of a high turbulence causing device such as a check valve or in the vena contracta formed by flow through orifice 208a. In such an area, any longitudinal and axial concentration gradients are minimized. A second mixing orifice downstream at a transition length or more tends to suppress radial concentration gradients.

Yet another type of a high turbulence causing device or member containing a gas injecting member is shown in FIG. 13 which is described below in detail with respect to the injection of a polyelectrolyte resin solution. Short tube 145 within a flow pipe or tube 147 causes a region of high turbulence mixing. The entry into the short tube section 145 is a flat or blunt 90° annular flange 151. The location of the injection member or tube 153 is preferably at the vena contracta of the flow. Preferably, the tip of injection tube 153 is located in the center of short tube 145.

Figure 15C:
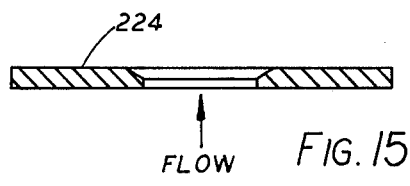
FIG. 15c is a cross-sectional view of a flat plate orifice.
Figure 15B:
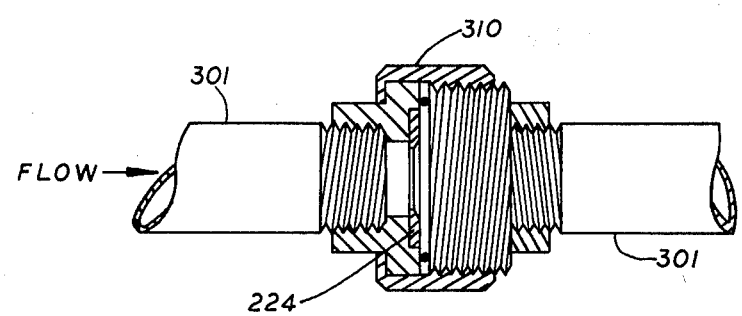
FIG. 15b is a cross-sectional view of a union containing an orifice.
Figure 15A:
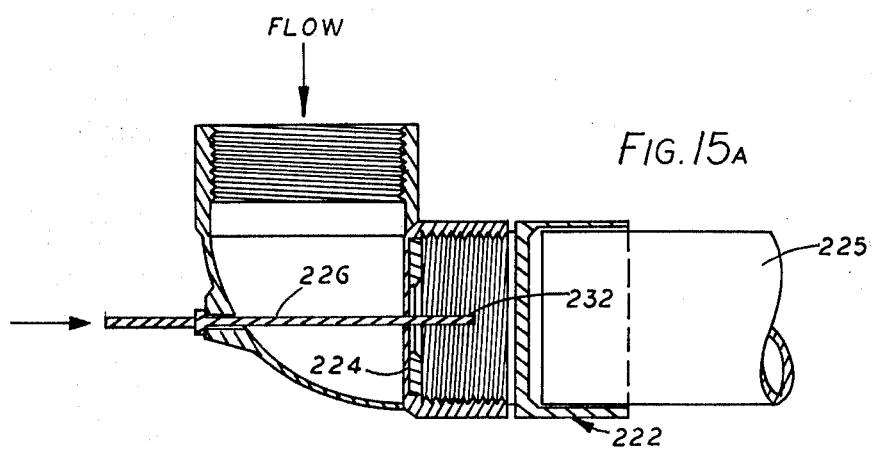
FIG. 15a is a cross-sectional view of an injection mixing elbow.

Another example of a high turbulence causing device in this case containing a gas injector member is shown in FIG. 15. In FIG. 15a, an injection mixing elbow generally indicated by the numeral 222 having an orifice 224 is located with the elbow at the commencement of the radius. A pipe 225 is attached to the elbow in any conventional maner. A small diameter pipe or tube 226 is inserted through the elbow and through the orifice 224 so that the tip 232 is located within the high turbulence and desirably at or near the vena contracta portion downstream of which full mixing occurs within the flow line or pipe generally indicated by the numeral 225.

The location of the tip 232 of small injection pipe 226 is important with respect to thorough mixing and suppression of concentration gradients. Generally, tip 232 may be located from about 0.25 to about 0.5 pipe diameters downstream or at a highly preferred distance of from about 0.36 to about 0.39 diameters with about 0.375 diameters being the optimum location.

A flat plate orifice which may be utilized in the elbow is shown in FIG. 15c. Generally the orifice diameter is from about 0.7 to about 0.9 of the conduit diameter and may have a taper (at about 6.0°) leading from the orifice opening. In FIG. 15B, orifice 224 is located within a coupling or union, generally indicated by the numeral 310, and connects pipes or conduits 301.

FIG. 15b shows the flat plate orifice in a coupling. Of course, the orifice can be utilized at numerous locations such as tees, elbows and the like or simply in a straight portion of a conduit.

As should be apparent to one skilled in the art, numerous types of turbulence causing devices containing gas injectors such as small pipes may be utilized. However, in situations wherein the monetary expense of gas injection into a pipe or the like is low, high mixing efficiency as exemplified by optimal, i.e. flat plate orifices with coaxial injection may not be required. Rather, it is sufficient to inject an amount of gas into a liquid such that the total amount of gas is in excess of that required to reach saturation within the flow pipe. Thus, the gas may be injected as through a normal straight portion of a pipe line or in many other locations such as at a check valve following a pump, in tees, elbows, valves or wherever turns or fittings cause turbulence.

Preferably, turbulence causing devices such as orifices or turbulence causing fittings or turns are located downstream throughout the liquid flow system preferably separated by at least one transition length e.g. from 25 to 40 pipe diameters for turbulenet flow and preferably more than 40 diameters to maintain the saturation level of the liquid or to cause the saturation level to be reached where it is not reached through the addition of the gas through a non-high turbulent area as through an elbow. The amount and number of such devices will depend largely upon the system utilized as should be apparent to one skilled in the art.

The net effect of the addition of an excess amount of gas above the saturation level of the liquid is to provide a distributed air chamber comprised of dispensed fine bubbles with the fluid along the entire length of the flow pipe and system which acts as a distributed surge suppression air chamber rather than a discrete air chamber. As above noted, preferred gases are those which are not unduly reactive and which exhibit low saturation levels in the particular liquid transported. Of course, numerus gases may be utilized. Specific preferred gases generally include: oxygen; ozone preferably in a carrier gas, e.g. air, oxygen-enriched air, or oxygen, etc; nitrogen; carbon dioxide; air, natural gas, exhaust gas, e.g. from a diesel engine driven pump, distillate gases such as propane, butane, pentane, etc. and the like.

Although the above described surge suppression system may be utilized in generally any liquid flow system, it has been found to be particularly suitable in suppressing surge pressures in any liquid transmission system such as in the flow system of a waste treatment facility such as set forth above where it may be added in the force mains.

AERATION OF MUNICIPAL COLLECTION SYSTEM

A dispersed municipal collection system was equipped with aeration equipment according to the principles set forth. Before aeration, waste received at the processing plant was septic, exhibited zero or trace dissolved oxygen and exerted no demand on oxygen saturated in the waste after it entered the plant.

In contrast, after all force mains and wet wells were aerated, the dissolved oxygen of received raw waste reached 3 to 4 ppm. The waste was treatable as indicated by its oxygen demand of more than 10.0 ppm per hour. The dissolved oxygen content sufficed to sustain aerobic conditions throughout primary sedimentation. The effluent from this first stage of processing still exhibited a dissolved oxygen concentration exceeding 1.0 ppm. These results dramatically attest to the efficacy of these teachings of aeration. The desired suppression of odor from septic decomposition was a noticeable further result.

CLORINATION

It should be understood that the invention further contemplates that chlorine mixing utilizing the flat plate orifices and injection at numerous points under high momentum exchange mixing conditions is clearly possible. The use of chlorine in a gaseous state for gaseous mixing injection or as a liquid solution is contemplated by this invention. FIG. 1 illustrates more typical points of injection for a chlorine and water solution through line 40 into line 36 to the effluent from the secondary sedimentation tank 24. Further, the invention quite definitely contemplates the injection of chlorine in the disinfection portion 38 of FIG. 1.

SEDIMENTATION

The invention contemplates the injection of aluminum chloride or some other suitable sedimenting agent into the effluent at some point in the process preceding the final disinfection contact element to assist in clearing the water when it is finally discharged into a receiving stream, river, or the like. With the use of aluminum chloride, the invention contemplates the injection of about 25 to 100 parts per million, with this being followed by a polymer injection after a delay of two to three minutes. The aluminum chloride injection might take place for example in a somewhat rectangularly shaped trough 135 mounted in the bottom of the trickling filter tank 120 of FIG. 4. This trough 135 would collect all the water which trickled down through the filter media and then be passed through the output line 138. In order to inject the aluminum chloride into the effluent at this point, a plurality of transversely extending pipes 137 are mounted to extend across the trough 135, again as best seen in FIG. 14, with the aluminum chloride injection being through a pipe 139 which individually communicates with each of the four pipes 137 illustrated in FIG. 4.

Further mixing of the aluminum chloride is then followed in its passage of pipe 138 by entry into a multiple short tube section indicated by numeral 141 which is primarily designed for mixing. In addition, because of the slow flow rate through the trough 135, the injection of a polyelectrolyte resin may be made with coaxial injection into the vena contracta, at the end of the multiple short tube section 141 to achieve the effect of a flocculating agent as is well known in the art. The short tube whether singular or multiple effects a highly effective mixing arrangement. A single short tube is illustrated schematically in FIG. 13, and is illustrated generally by the numeral 143. The tube in effect comprises as a feeding device, a reduced diameter short tube section 145 which is coaxially mounted within the outer normal diameter tube section 147. The entry into the short tube section 145 is with a flat blunt 90° angular flange 151 so that considerable and extreme turbulence characteristic of entrance conditions is present within the short tube section 145. The injection of the polyelectrolyte resin, or any other suitable resin might be through a small injection tube 153 which is positioned so as to be approximately 0.75 diameters of the small tube 145 from the entrance with the flow being in the direction of arrow 155.

Thus, with the short tube, it should be understood that the entrance from the tube creates a mixing, and that such short tubes may normally occur in existing conduits or extensions of existing conduits. For example, in the section 141, it is contemplated that perhaps three short tubes would be arranged in side by side bundle relationship with flow being in one end of one down through and reversing its direction a third time to pass out through a third short tube with flow being in parallel or in series. This particular short tube arrangement might actually have a total length in the three short tubes of twenty diameters of single conventional conduit, and preferably should not have less than a ten diameter length.

It is, however, desirable that the mixing be accomplished under a low shear condition, particularly for the polyelectrolyte resin which should be injected at between 0.2 to 0.6 ppm and between 1½ to 3½ minutes following the injection of the aluminum chloride. It should be fed in a carrier fluid, preferably water, at an actual concentration of 0.1% or less. The entrance section forms a contraction in the influent flow. This serves as an equivalent orifice. Where entrance effects are absent, actual orifices inserted should be of diameter greater than 0.5 and preferably between about 0.75 to about 0.9 of the inside diameter of the conduit. Thus, these figures represent the ratio of the orifice diameter to the actual diameter of the large flowing pipe or pipe 147 in FIG. 13. Downstream of the orifice, the length of the tube should be as close to a commplete transition length as possible, i.e., 25 to 40 diameters.

In actuality the stream within the short tube of FIG. 13 if flowing under high pressure is probably contracted somewhat more for a given depth of water or given pressure head. We have found that the best length for the tube 145 should probably be about 2.5 diameters. Under these conditions, the head loss is 0.328H where H is the hydraulic head upstream of the tube. If the tube 145 is vented, it may allow full flow through the tube rather than the contracted flow defined above. However, we have found that no venting of such tubes needs to take place. Actually, for most efficient mixing, a non-laminar flow through the tube 145 is highly desirable.

The use of the short tube also is achieving mixing under a hydraulic gradient, rather than a gravitational gradient, and in this manner, high efficiency as well as saturation above that existing at reduced pressure levels in gravitational systems is definitely achieved.

NITRIFICATION

Standard processes involve carbonaceous BOD reduction. However, new state and federal requirements are being imposed for nitrogenous oxygen demand or NOD reduction. The process defined above, particularly that as associated with FIG. 1 of the drawings as being the optimum system uses either all ammoniation teaching, or all break point chlorination, or a split somewhere between these two. Preferably, the system should be based on a two stage trickling filtration with return of stabilized digester supernatant sludge bed drainage, filtrate or concentrate as shown in FIG. 1. This makes the trickling filters convert all the ammonia nitrogen to ammonia or $NH_3$. $NH_3$ is then separately oxidized to nitrate, or $NO_3$ or, is stabilized by break point chlorination to form monochloramine.

The oxidation of the $NH_3$ to $NO_3$ requires oxygen equivalent to four to five to six times the ammonia-nitrogen concentration currently found in present systems. Specifically, this amounts in the system designed above to 140 ppm of oxygen. Thus, for properly aerated waste with oxygen, a closed extended out fall line would allow the oxygen use to achieve the breakdown of the $NH_3$ to $NO_3$. This would preferably here to be done before disinfection. It seems more practical to utilize a supplemental aerobic process such as an aerobic nitrification unit as described in this specification.

This would produce nitrates. Then, disinfection would occur after nitrification.

In this nitrification effluent may also be under a pressure in its flow path, so that it could be under several atmospheres' pressure, for example. Under this processing condition, much greater concentrations of gas or fluid can be saturated thereinto. The effluent could be maintained under pressure until processing was fully completed. Aeration is believed to be more efficient and easier under such a pressure system.

The various embodiments of the present invention can be utilized to achieve an optimum process for the conversion of ammonia to ammonium nitrates, particularly in waste or sewage treatment plants. In general, the secondary treatment effluent from a waste or sewage treatment plant can be fed to a nitrification tower and treated in a manner and method as set forth in Water and Sewage Works, August, 1974, Pages 92 – 94 which is hereby fully incorporated by reference with respect to the manner, processes, equipment and techniques utilized to produce low ammonia effluent including the utilization of a plastic media trickling filter such as Surfpac supplied by the Dow Chemical Company. Utilization of applicant's various apparatus processes and techniques will result in an improved process with the production of even lower ammonia effluent concentrations throughout the year.

According to the concepts of the present invention, the secondary treatment effluent may be fed to the nitrification tower through a distributor arm hereinbelow described in detail. The primary advantages of utilization of this distributor arm is to distribute an even amount of effluent to each unit area or square foot of the nitrification tower, regardless of whether it is located near the center of the tower, at a mid portion of the tower or at a radially outward point. This results in an improved efficiency of distribution and hence better utilization of available contact area for nitrification.

The secondary treatment effluent can be aerated for feeding to the nitrification tower. Aeration or the introduction of dissolved oxygen into the effluent can take place in a manner set forth hereinabove and as described in the applicants' previously issued patents cross referenced herein. A preferred technique is to utilize an air injection nozzle into the conduit within the vena contracta portion of a turbulence causing device such as a flat plate orifice as taught hereinabove. A preferred amount of oxygen to be added is from 2 to 5 parts per million parts of secondary treatment effluent. The provision of the oxygen, of course, promotes nitrification or conversion of the ammonia to nitrate.

Another aspect to improve the conversion of ammonia to nitrate involves the utilization of packed media within the nitrification tower as hereinafter described such as Berl saddles, pall rings, and the like or the specialized media described above wherein the hydraulic radius of the external flow channels is substantially equal to the hydraulic radius of the internal flow channels. This provision ensures efficient aeration of biological plaques and hence a greater conversion. Although the plastic media trickling filter (Surfpac) or rotating media (BIOSURF) may be utilized, the packing media having equal internal and external hydraulic radii are preferred.

Generally, due to temperature difference, it is harder to produce a satisfactorily low level of ammonia effluent during the winter period than it is in the summer. Hence, another expedient incudes the provision of insulating the nitrification tower to sustain warm effluent temperatures and this is facilitated by minimizing the ambient air flow through the packed bed which would otherwise suppress reaction rates owing to the cooling which would be induced. This air flow is unnecessary with an aerated inflow into the nitrification process.

SYSTEM INTEGRATION

The arrangement of the overall units of FIG. 1 can function in waste treatment. One mode of operation is to allow all elements to float on line as the influent hydraulic and organic load changes. Typical changes in these two loads are high. In terms of an average daily load, the range may be as great as ±75% of the average load. Regulatory authorities usually stipulate that at no time shall prescribed limits for effluent quality be exceeded. With a highly variable input load, this means either that the process must be controlled to overtreat waste most of the time, or that relatively sophisticated control is necessary to achieve the necessary degree of treatment at any time. Both capital and operating expenses maybe lower in the latter case. However, the usual engineering approach tends toward the forward technique. With this approach, simplified controls and regulation may achieve a degree of treatment satisfactory for a only fixed design condition. For any other input loading, effluent quality will vary.

Tests have shown that using the system with the sedimentation tank defined herein the DO level to the tank is about 2 to 3 ppm, and out of the tank about 1 to 1½ ppm to definitely maintain the aerobic condition. This aerobic condition remains between 20 to 40 minutes after the effluent leaves the sedimentation tank.

SCRUBBER

According to the concepts of the present invention, a scrubber including an air washer type may be provided for purification as in the deozonation of an ozonated gas. That is, the residual or unreacted ozone from the sewage waste treatment facilities as above set forth may be treated to effectively remove the ozone from the gas medium. Whenever a scrubber is utilized, it is to be understood that a washer may also be utilized.

Figure 16:
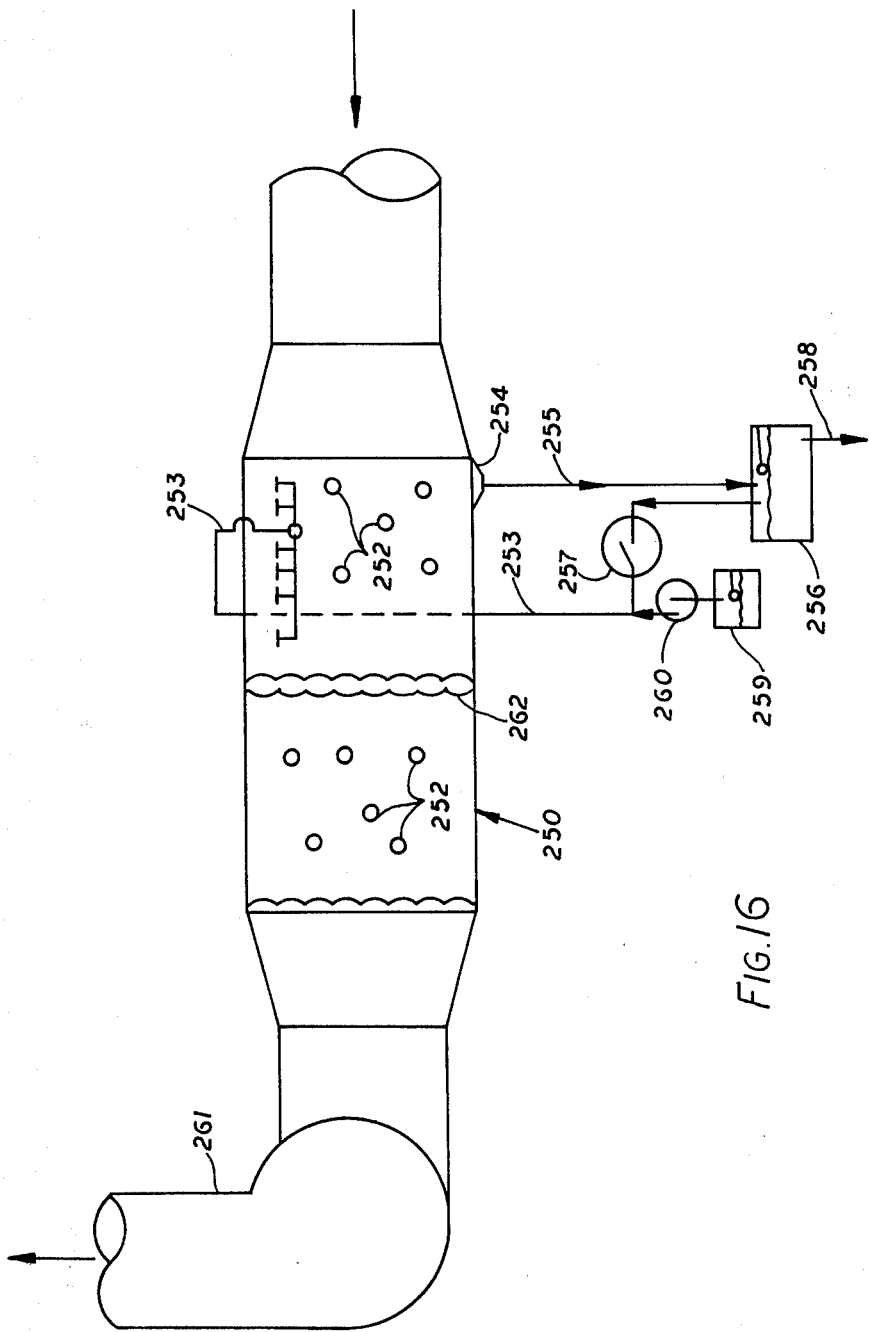
FIG. 16 is a schematic view of a two stage scrubber.

A two stage scrubber, generally indicated by the numeral 250, is shown in FIG. 16. Scrubber 250 may generally be any conventional scrubber and therefore contain a packed media 252 such as Raschig rings, Pall rings, Berl saddles, single spiral media and the like. The treating medium may be inserted at the top of the first stage of the scrubber, through reagent feed line 253. The treating medium will, of course, trickle down through the first stage and collect in drain 254 from which it flows through drainline 255 to a make up tank 256. The treating medium may then be recycled by recirculating pump 257 or a portion may be discarded as through waste line 258. Make-up may be supplied to tank 258. A reagent supply tank 259 having a pump 260 may be located to discharge to an injection-mixing system on the pressure side of the recirculation pump 257. Reagent make-up to the metering pump sump may be by controlled by float or other sensing means. Sensing may detect a reagent or treating medium parameter.

The fluid to be treated in the scrubber is admitted to one end of the scrubber as indicated in FIG. 16 and has previously been thoroughly mixed and the contaminant is to be removed as through the use of high solubility fluids, decomposing fluids or fluids catalyzed to promote decomposition, or oxidizing agents, or reducing agents. The gas to be removed or decomposed with respect to the above-noted disclosure may be ozone. From this stage, an ozone-free fluid is then admitted to the second stage.

Although not shown in detail, the second stage may be identical to the first stage in that it contains packed media and contains necessary tanks, lines and pumps for supplying aeration, reagents, reagent makeup or medium makeup to the second stage. Once again, the treatment medium may either be high-solubility fluids, oxidizing agents or reducing agents. After the two stage treatment in the scrubber, the fluid is greatly purified and then is discharged through a blower 261. The first stage is separated from the second stage in any conventional manner and may contain eliminator plates 262 which remove liquid droplets and mist and thus prevent the liquid or treating medium in the first stage from entering the second stage.

A conventional washer type scrubber may be utilized in lieu of a scrubber. More specifically, it consists of three elements. Spray nozzles, scrubber plates and eliminator plates. The nozzles are placed in a bank across the path of the air and the water is forced through them by a pump and is discharged in a fine spray or mist preferably in the direction of the air flow. Counter-flow or cross-flow sprays may also be used. In some cases two or three banks of nozzles are used. The air is drawn through the washer by the fan and is thus brought into intimate contact with the water and some of the dirt and soluble gases and particulate material are removed. The real cleansing, however, is done by the scrubber plates which are designed to change the direction of flow so that the dirt will be thrown out of the air by its momentum and by the rubbing of the air over the wet surface. The plates are kept flooded either by the spray nozzles or by a separate row of nozzles placed above them. Following the scrubber plates is a series of eliminator plates whose function is to remove the entrained water from the air. The lower part of the washer constitutes a tank into which the water falls and from which it is taken by the circulating pump. A float valve admits fresh water as required to replace that evaporated. Provision may be made also to waste a portion of the sump tank volume through a waste line to effect discharge from the system.

Proper provision must be made in an air washer to prevent trouble from the large quantities of dirt which are washed from the air and deposited in the tank. This is one function of the waste line. A screen of ample area is also necessary on the suction line to the pump to prevent the dirt from being carried into the circulating system and in some cases special devices may be necessary to enable the spray nozzles to be cleaned periodically by flushing. The accumulated dirt must be removed from the tank at frequent intervals. In a ventilating system where the outside temperature falls below the freezing point, it is necessary to protect the air washer from freezing either by incorporating a tempering heater ahead of it in the air stream or by utilizing an anti-freeze solution in the sprays themselves. The air washer is fairly effective in cleansing the air of dust but has two other very important functions. It can be used as a humidifier or as a dehumidifier and cooler and as such is valuable in air conditioning. In the case of dehumidification it is apparent that a refrigeration element is required and in this event the spray liquid may very well be an anti-freeze solution having preferential solubility for the contaminant gases which are of primary concern.

Whether a cross flow scrubber or a washer type scrubber is utilized, an alternative embodiment is to use packing such as that set forth above, or the specialized packing described which include pall rings, Berl saddles, etc. wherein the hydraulic radii of the external and internal flow channels are substantially the same. Such a provision is more clearly set forth in my existing U.S. Pat. No. 3,730,881, issued May 1, 1974, which is hereby fully incorporated with respect to the hydraulic radius of the internal and external diameters.

When the fluid to be purified is contaminated with ozone as from a waste or sewage treatment plant, the ozone concentration must be reduced so that less than 1/10 parts per million parts of gas obtained from the scrubber is ozone since more than this concentration of ozone tends to be toxic. The above described scrubber containing the packed bed having the characteristic hydraulic radii described has been found very effective in purifying, either by solubility or through a chemical reaction to or below the critical limit, 0.1 ppm $O_3$ in fluid.

The scrubber fluid is generally different in each stage of the scrubber to effect maximum purification. Although the scrubber may be utilized to remove or purify ozone as described, in general it can apply to the purification of any gas which is to be treated by a liquid in a fluid phase type operation. Hence, examples of other types of gases include ammonia, chlorine, hydrogen sulfide, sulfur dioxide, and the like. Depending upon the nature of the gas to be removed, it may first be treated with a soluble fluid, an oxidizing agent, or a reducing agent. Specific examples of soluble fluids or absorbing agents which may be generally used include liquid acids having 1 to 6 carbon atoms such as acetic acid, propionic acid, aliphatic alcohols having from 1 to 8 carbon atoms such as isopropyl, butyl, amyl and the like, glycol mixtures having from 2 to 10 carbon atoms such as propylene glycol, anhydrides having from 4 to 12 carbon atoms such as acetic anhydride and propionic anhydride, carbon tetrachloride and Freons which are liquid at the operating temperature of the scrubber.

The oxidizing agents generally can include any oxidizing agent such as sulfuric acid, ethylene oxide, potassium permanganate, solutions of chlorine or chlorine dioxide, ozone and air or ozone and oxygen, nitric acid, various metal dichromates, potassium perchlorate, hydrogen peroxide, hydrogen peroxide in water, sodium nitrite, and the like. Of course, oxidizing agents with respect to the component of the gas to be treated are well known to those skilled in the art. Ethylene oxide is desirable for sterilization as well as with inert diluent gases (e.g. carbon dioxide, and nitrogen) to suppress explosion hazards.

Considering now the reducing agents, again a wide range of reducing compounds may be utilized in the general purification of a gas or more particularly a component of a gas phase. Specific reducing agents include sulfur dioxide, a metal metabisulphite such as sodium metabisulphite, cesium compounds, and the ike. Once again, numerous compounds which act as reducing agents with respect to the desired component of the gas to be treated are well known to those skilled in the art. Preferred reducing compounds for the purification of ozone include sulfur dioxide and sodium metabisulphite.

Concerning the removal of ozone, preferably the first stage of the scrubber contains an absorbing agent and since ozone tends to be an oxidizing agent, the second stage of the scrubber is preferably a reducing agent. Usually ozone would be eliminated in the first stage. Then the second stage could utilize chlorinated effluent or a very dilute chlorine solution which is itself deodorizing. However, the initial stage may contain a reducing agent as a treating fluid followed by the second stage containing a soluble fluid compound as a treating fluid. Of course, many variations can exist. Preferred fluids for ozone include acetic acid, acetic anhydride, propionic acid, propionic anhydride, carbon tetrachloride, and hydrogen peroxide in water.

It should be apparent that in the use and purification of any toxic gases such as ozone in air, chlorine in air or the like, safety interlocks are to be provided throughout the entire system to prevent dangers or harmful effects upon human beings from ozone or chlorine exposure in the purifications and operation areas. Moreover, the location of the initial injection of the toxic gas into the treatment process is preferably remotely located from the scrubber operation for safety purposes as well as being necessary for efficient injection mixing and for adequate contact.

FLUID-FLUID TREATMENT

According to the concepts of the present invention, a fluid but desirably a gas can also be treated or purified by treatment with fluid under conditions of high turbulence, that is, a Reynolds number of at least 3,000, to ensure adequate mixing or momentum transfer. In general, a high turbulence purification treatment may pertain to generally any type of gas although it is particularly suited in the purification of ozone as utilized in the treatment of waste treatment facilities as well as sulfur dioxide.

Figure 17A:
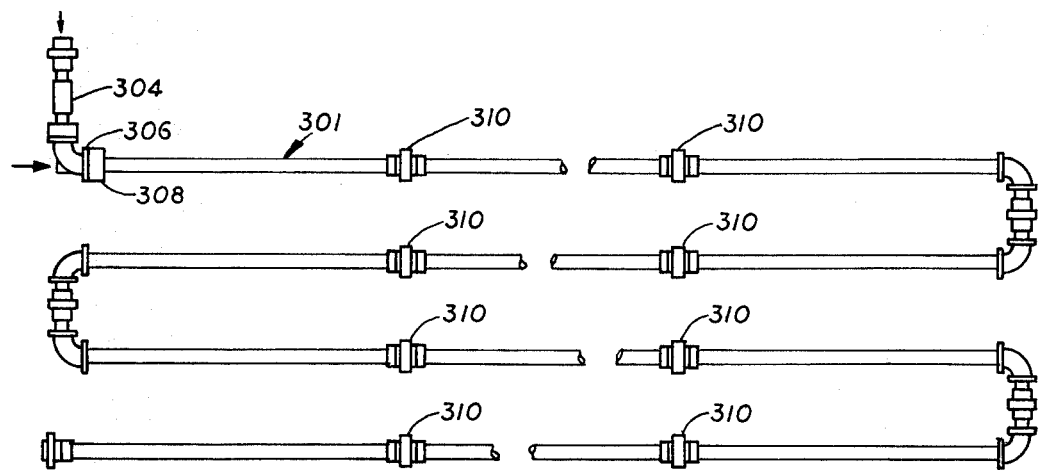
FIG. 17A is a cross-sectional view of a highly efficient fluid-fluid treatment system utilizing high turbulence-causing devices.
Figure 17B:
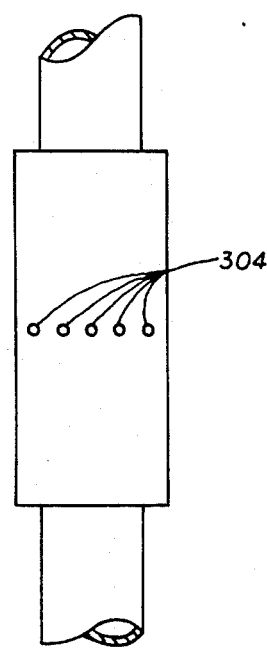
FIG. 17B is a schematic view showing a grid located in a portion of the fluid-fluid treatment system.

Referring to FIG. 17, purification or treatment of a gas may be carried out in a flow conduit, preferably circular, as in a pipe line, generally indicated by the numeral 301. The gas is admitted to the flow channel as indicated by the arrow and is conveyed through the channel as indicated by the arrow and is conveyed through the channel and exhausted. It is highly desirable that the Reynolds number be in excess of 3,000 to ensure turbulent condition throughout. Preferably, to ensure that a reproducible velocity profile is maintained when beginning the treatment, the grid 304 exists to produce, suppress and reduce any velocity gradients within the incoming gas. Typically, the grid may be made of wire, plastic or the like and may be a coarse screen. For example, it may merely be a screen grid with members on approximately one-inch centers of coarse wires having a diameter of approximately 1/16 of an inch. Of course, the size of the rid and wires may vary. The important factor is that a grid may be utilized which ensures the reduction of any velocity gradients. These gradients are likely to be found in discharge sections of fans, blowers, and fittings such as elbows.

Located downstream of grid 304 is a high turbulence causing device such as a flat plate orifice indicated by the numeral 306 and described herein. Generally, the turbulence causing device can be located at an elbow, union, tee or the like as previously noted. Preferably, the treating fluid is injected into the vicinity of the orifice so that rapid and thorough mixing quickly takes place. Desirably, this can be accomplished through a nozzle 308 which extends axially into the central portion of the flat plate orifice or turbulence causing device and slightly downstream as in the vena contracta caused by the orifice. Generally, the orifice diameter ranges from about 0.7 to about 0.9 of the conduit diameter. A minimum ratio of 0.5 may be used if high pressure drops can be accommodated. The location of the vena contracta is usually about 0.25 to 0.5 conduit diameters downstream from the orifice plate, preferably at 0.37 to 0.39 and it is at this region where the nozzle is preferably located. To further ensure thorough and complete mixing, at least one or a second turbulence causing device may be located downstream such as a flat plate orifice indicated by the numeral 310. The second turbulence causing device may be identical to the first device and preferably is located downstream at least a distance of 25 to 40 conduit diameters or greater and preferably at least 40 diameters. This is to ensure that a proper length exists for adequate or thorough mixing. The second turbulence causing device further ensures thorough mixing and hence derives the maximum contact probability for efficient purification of the gas. The treated or purified gas may then be handled in any conventional manner such as by extended contact possibly followed by exhausting to the atmosphere, by recirculation, or by the addition to a process or the like.

Figure 19:
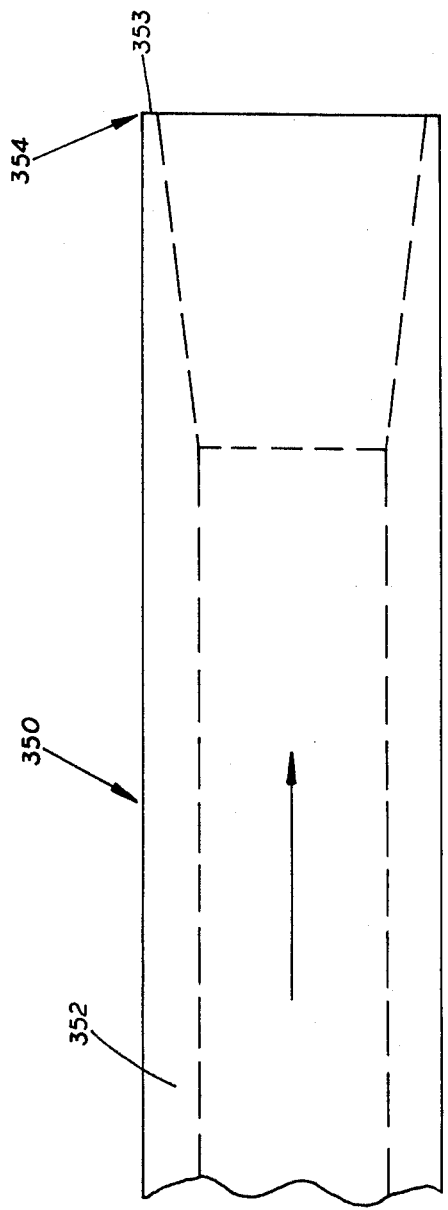
FIG. 19 is a cross-sectional view of a nozzle.

Although the nozzle may generally be a thin pipe or tube, a preferred nozzle is shown in FIG. 19 generally indicated by the numeral 350. Nozzle or distributor 350 generally has a first portion having an average thickness indicated by the numeral 352. The diameter of the nozzle in a second portion proportionally increases until a very thin annulus 353 exists at the tip generally indicated by the arrow 354 of the distributor. The slope of the tapered portion of the distributor is generally less than 7° and preferably about 2° to about 3° on either side. A desirable thickness of the annulus at the tip of the distributor is about 0.01 inches. The diameter, as indicated, generally increases at a proportional rate to accommodate pressure drop of a fluid such gas and moreover to ensure good strength and rigidity of the distributor portion. Such a diffuser tipped distributor also tends to reduce the flow velocity of the gas. Due to the provision of a very thin annulus at the top of the nozzle, the injected fluid such as a gas is in very close vicinity to the conduit fluid and thereby tends to reduce any eddies as normally encountered with thick walled nozzles. Moreover, additional shearing action is encountered due to the lack of eddies and this promotes efficient and thorough mixing of the injected fluid as in the vena contracta region of a turbulence causing device such as a flat plate orifice.

In general, the high turbulence purification or treatment system may be applied to any type of fluid to be treated with a sufficient amount of a second fluid to effect purification. Purification or treatment may be obtained by absorption or high solubility fluids, chemical reaction, or the like and involve detoxification, deodorization, and the like. Additionally, the fluids may either be liquid-liquid, liquid-gas, gas-liquid, or gas-gas.

The high turbulence purification or treatment system is of particular significance with respect to waste or sewage treatment facilities wherein noxious or toxic gases are encountered such as ozone, chlorine, hydrogen sulfide, various organic odors, ammonia and the like. Thus, after sterilization or deodorization, should the fluid to be treated comprise ozone in oxygen or ozone in air, the treating fluid may be an oxidizing agent, a reducing agent, or an absorbing or high solubility fluid agent, as set forth above with respect to their utilization in a cross flow scrubber or washer. Thus, an absorbant compound such as propionic acid could be added through nozzle 308 and emitted in the vena contracta portion downstream from a first flat plate orifice device with further turbulence or mixing occurring at least 25 or more flow conduit diameters downstream as caused by a second flat plate orifice 310. Similarly, as will be apparent to one skilled in the art, other compounds may be added to treat the ozone through nozzle 308. In a similar manner, sulfur dioxide may also be purified.

The invention will be better understood by reference to the following tables which set forth the minimum flow rate required for turbulent flow conditions or thorough mixing. Table I, for a fluid-fluid system werein the larger length according to either 40 seconds contact time or a transition length of 40 diameters is utilized and similarly in Table II for a gas-liquid system wherein turbulence causing devices such as flat plate orifice are utilized.

TABLE I

MINIMUM FLOW DESIGN PARAMETERS FOR TURBULENT FLUID-FLUID, INJECTION - MIXING SYSTEMS

| Diameter IN. | 8 | 16 | 24 | 36 | 50 | 60 |
|---|---|---|---|---|---|---|
| Q, cfs | 2.8 | 5.6 | 8.4 | 12.5 | 17.5 | 21. |
| Q, cfm[1] | 167. | 335. | 502. | 750. | 1050. | 1256. |
| Length, ft.[2] | 320. | 160. | 106. | 70.7 | 51. | 43. |
| Length, ft., mix[3] | 27. | 53. | 80. | 120. | 167. | 200. |
| Velocity, ft. min. | 480. | 240. | 160. | 106. | 77. | 64. |
| Pressure Drop, in. $H_2O$/100 ft. | .06 | .0057 | .0015 | .00038 | .000135 | .000078 |
| Pressure Drop, in. $H_2O$/Inj. Mix | .35 | .11 | .06 | .03 | .01 | .005 |
| Pressure Drop, in. $H_2O$/Contact | | | | | | |
| Req'd, gm/hr.[4] | | | | | 12.8 | |
| Oxygen Req'd cfm[5] | | | | | .11 | |

[1]Based on DV = 64. minimum flow to ensure turbulence, D. inches, V. ft per sec.
[2]Based on 40 seconds contact time.
[3]Based on 40 D.
[4]Based on 5% ozone in oxygen from ozonator.
[5]Based on 6 ppm ozone from oxygen in air.

TABLE II

CHARACTERISTIC DESIGN PARAMETERS FOR OXYGEN OR AIR, GAS-LIQUID, INJECTION-MIXING SYSTEMS
Note That Data Are For Minimum Capacity To Ensure Turbulent Flow

| Diameter In. | 1 | 2 | 4 | 6 | 12 | 18 |
|---|---|---|---|---|---|---|
| Q min., cfs[1] | .027 | .054 | .108 | .162 | .324 | .486 |
| Q gpm, minimum | 12.2 | 24.4 | 48.8 | 73.2 | 146.5 | 219.7 |
| Length, ft.[2] | 200. | 100. | 50. | 33.3 | 16.7 | 11.1 |
| Length, ft., injection-[3] mixing stage | 12.5 | 25. | 50. | 75. | 150. | 225. |
| Velocity Min., ft.sec.-[1] | 5. | 2.5 | 1.25 | 0.83 | .416 | .28 |
| Air Req'd., $N_2$ sat'n., cfm[4] ($O_3$ at 0.56 ppm) | .030 | .060 | .12 | .18 | .36 | .54 |
| Ozone Feed, lb./day | .082 | .16 | .33 | .49 | .98 | 1.5 |
| Oxygen Req'd., $O_2$ sat'n cfm[5] ($O_3$ at 1.25 ppm) | .049 | .098 | .196 | .30 | .60 | 1.20 |
| Ozone Feed, lb./day | .183 | .37 | .73 | 1.1 | 2.2 | 3.3 |
| Pressure Drop, ft., injection-mixing stage | 1.43 | .68 | .15 | .07 | .03 | .005 |
| Pressure Drop, ft., contact stage | 16. | 1.12 | 0 | 0 | 0 | 0 |
| Pressure Drop, ft., total | 17.5 | 1.8 | .15 | .07 | .03 | .005 |

[1]Based on Reynolds Number limitation for turbulent flow, DV = 5.
[2]Based on 40-seconds contact time.
[3]Based on 150 diameters.
[4]Based on 2.5% $O_3$ in air and a dose corresponding to nitrogen saturation which yields an $O_3$ in liquid concentration of 0.56 ppm.
[5]Based on 5% $O_3$ in $O_2$, 40 ppm saturation of oxygen.

Table No. III sets forth data showing the excellent mixing obtained when a turbulence causing device is utilized in a conduit of a fluid-fluid system. In order to determine the extent of mixing, five samples were taken at 30 conduit diameters downstream of the location in the fluid-fluid system where water vapor (gas) was injected into air (gas) in the vena contracta portion of a flat plate orifice. The first location being at a radius wherein the area of the succeeding circle or annulus was equal to one quarter of the total area. The orifice ratio with respect to the conduit diameter was 0.75. The following data was obtained.

TABLE III

| Location, R Test/R Total | 0 | .354 | .61 | .788 | .932 |
|---|---|---|---|---|---|
| DBT, ° C | 18.2 | 18.2 | 18.2 | 18.2 | 18.2 |
| WBT, ° C | 15.8 | 15.8 | 15.9 | 15.9 | 15.9 |
| Grains 1 lb. | 72. | 72. | 71.1 | 71.1 | 71.1 |

TABLE III-continued

| Comp, ppm. | 10,286. | 10,286. | 10,157. | 10,157. | 10,157. |
|---|---|---|---|---|---|

As readily apparent from the above data, very, very small differences in concentration were obtained at various locations along a radius. Additionally, the concentration variation was generally 1% less than the concentration average. This table thus conclusively establishes that excellent mixing is obtained even after a transition length of 30 diameters. This is in comparison with applicant's preferred minimum transition length of 40 diameters which necessarily would give better mixing. Of course, applicant's invention also relates to the incorporation of additional downstream turbulence causing devices to ensure thorough mixing throughout the system. Moreover, the data establish that a flat plate orifice having an orifice ratio of 0.75 bases upon the conduit diameter establishes good mixing conditions.

GAS-LIQUID CONTACTING SYSTEMS FOR CHEMICAL REACTIONS

As should be apparent to one skilled in the art, many different types of fluids such as gases may be treated. Moreover, a singular advantage of the in line reactor or flow conduit for generating chemical reactions involving gas-liquid systems is the amenability to variation in pressure and/or temperature in the pipe line reactor in comparison with that which is available in reaction kettles, packed beds or the like.

The basic form of the pipe-line reactor for gas-liquid chemical reactions appears in issued patents cross referenced herein. In this application, illustrative arrangements and details appear in FIGS. 15A, 15B, 15C, and 17A and 19. Illustrative of industrial processes which are of importance and which involve gas liquid reactions are the various examples set forth in "Examples of Processes of Industrial Importance where Gas Absorption is Accompanied by Chemical Reaction", Gas-Liquid Reactions, P. V. Danckwerts, F. R. S., McGraw-Hill Series in Chemical Engineering, 1970, which is hereby fully incorporated by reference with respect to the various reactions as well as to the references cited therein. An abstract of this article which sets forth illustrative examples is as follows:

1. $CO_2$, COS, $H_2S$, $Cl_2$
   i. Absorption of $CO_2$ and $Cl_2$ in aqueous solutions of barium sulphide for the manufacture of $BaCO_3$ and $BaCl_2$, respectively; see Gupta, R. K. and M. M. Sharma: Ind. Chem. Engr. 9 (1967) Trans. 98.
   ii. Absorption of $CO_2$ in aqueous suspensions of lime for the manufacture of precipitated $CaCO_3$; see Morris, R. H. and E. T. Woodburn: South African Chem. Processing (June –July 1967) CP 88.
   iii. Absorption of $CO_2$ in aqueous suspensions of MgO for the manufacture of basic $MgCO_3$; see
      a. Shreve, R. N.: Chemical Process Industries, 3rd Ed., McGraw-Hill, 1967.
      b. Faith, W. L., D. B. Keyes, and R. L. Clark: Industrial Chemicals, 1965, 3rd ed., John Wiley and Sons, Inc., New York.
   iv. Absorption of $CO_2$ in aqueous suspensions of CaS; see Chem. Engng. 75 (1968) 94.
   v. Absorption of $CO_2$ in aqueous solutions of sodium silicate; see Dalmatskya, E. J.: J. Appl. Chem. USSR 40 (1967) 464 (Engl. Trans.).
   vi. Absorption of $CO_2$ in aqueous solutions of $Na_2S$.
   vii. Absorption of $CO_2$ in aqueous solutions of potassium carbonate or amines, for removal of $CO_2$ from synthesis gas; see Danckwerts, P. V. and M. M. Sharma: Chem. Engr. (October 1966) CE 244 (see 10-1).
2. $CS_2$
   Absorption in aqueous amine solutions for the manufacture of dithiocarbamates; see Kothari, P. J. and M. M. Sharma: Chem. Engng. Sci. 21 (1966) 391.
3. $O_2$
   i. Absorption of $O_2$ in aqueous solutions of CuCl for conversion to $CuCl_2$ and copper oxychloride; see Jhaveri, A. S. and M. M. Sharma: Chem. Engng. Sci. 22 (1967) 1 (see 10-3).
   ii. Oxidation of $Na_2SO_3$ by air or oxygen; used for establishing the characteristics of absorption equipment (see 10-3).
   iii. Air oxidation of acetaldehyde, butyraldehyde, etc., for the production of corresponding acids and acid anhydrides; see
      a. Marshall Sittig: Organic Chemical Process Encyclopedia, Noyes Develop. Corp., U.S.A., 1967.
      b. Vrbaski, T., and I. Brihta: Arhiv. Kem. 24 (1952) 111; C. A. 49 (1952) 163.
      c. Kostyck, N. G., Loov, S. V., Falkovski, V. B., Starkov, A. V., and N. M. Levina: Zh. Prikl. Khim. 35 (1962) 2021, J. Appl. Chem. USSR 35 (1962) 1939 (Engl. Trans.).
   iv. Oxidation of cyclohexane to adipic acid; see Steeman, J. W. M., S. Kaasemaker, and P. J. Hoftijzer; 3rd European Symp. Chem. Engng. Chem. Reaction Engng. Oxford, Pergamon Press, 1961, pp. 72–80.
   v. Air oxidation of cumene to cumene hydroperoxide (precursor for phenol); see
      a. Low, D. I. R.: Canad. J. Chem. Engng. 45 (1967) 166.
      b. Maminov, O. V. et al.; Khimiya i Tkh. Topliv., Masel (1967) (12), a (Brit. Chem. Eng. Abstract 1968 May, p. 712).
   vi. Air oxidation of toluene to benzoic acid; see Faith, E. L., D. E. Keyes, and R. L. Clark: Industrial Chemicals, 3rd Ed., 1965, John Wiley and Sons Inc, New York.
4. $Cl_2$
   A. Addition Chlorination
      i. Reaction between $Cl_2$ and $C_2H_5$ in $C_2H_4Cl_2$ medium; see Balasubramanian, S. N., D. N. Rihani, and L. K. Doraiswamy; Ind. Engng. Chem. (Fundamentals) 4 (1965) 184.
      ii. Reaction between $Cl_2$ and $C_3H_6$ in $C_3H_6Cl_2$ medium; see Goldstein, R. F.; Petroleum Chemicals Industries, 2nd Ed., 1958, London, E. & F. N. Spon Limited.
      iii. Reaction between $Cl_2$ and $C_2H_2$ to tetrachloroethane; see Marshall Sittig; Organic Chemical Process Encyclopedia, Noyes Develop. Corp., U.S.A., 1967.
      iv. Reaction between $Cl_2$ and trichloroethylene to give pentachloroethane (precursor of perchloroethylene); see Goldstein, R. F.; Petroleum Chemicals Industries, 2nd Ed., 1958, London, E. & F. N. Spon Limited.

B. Substitution Chlorination
  i. Chlorination of a variety of organic compounds such as benzene, toluene (side chain as well as nuclear), phenols, etc. See, e.g. Hawkins, P. A.: Trans. Instn. Chem. Engrs. 43 (1965) T.287.

C. Miscellaneous
  i. Reaction of $Cl_2$ with sulfur or sulfur monochloride to give sulfur monochloride and sulfur dichloride.
  ii. Reaction of $Cl_2$ with $SO_2$ to give sulfuryl chloride; see Kirk and Othmer: Encyclopedia of Chemical Technology, Vol. 13, 2nd Ed., 1967, New York, Interscience Publishers, pp. 319, 403.
  iii. Reaction of $Cl_2$ with $PCl_3$ to give $PCl_5$; see Idem., Vol. 10 (p. 477).
  iv. Reaction of $Cl_2$ with $FeCl_2$ to give $FeCl_3$; see Gilliland, E. R., R. F. Baddour, and P. L. T. Brian: A. K. Chem. E. J. 4 (1958) 223 (see 10-2).

5. $SO_3$
Absorption of $SO_3$ in $H_2SO_4$ for the manufacture of Oleum; see Duecker, W. W. and J. R. West: The manufacture of sulfuric acid, Reinhold Publishing Corp., New York, 1959.

6. $NO_2$
Absorption in water for the production of $HNO_3$; see (a) Andrew, S. P. S. and D. Hanson: Chem. Engng. Sci. 14 (1961) 105; (b) Kramers, H., M. P. P. Blind, and E. Snoeck; Chem. Engng. Sci. 14 (1961) 115.

7. $COCl_2$
Absorption of $COCl_2$ in alkaline solutions; see Monague, W. H. and R. L. Pigford: A. I. Chem. E. J. 6 (1960) 494.

8. $H_2$
Hydrogenation of a variety of unsaturated organic compounds in the presence of catalysts; see
  a. Satterfield, C. N. and T. K. Sherwood: The Role of Diffusion in Catalysis, Addison Wesley, 1963.
  b. DeBoer, J. H. et. al.: The Mechanism of Heterogeneous Catalysis, Amsterdam, Elsevier Publishing Co., 1960.

9. Deuterium
Ammonia-hydrogen process for deuterium separation; see
  a. Bourke, P. J. and J. C. Lee: Trans. Instn. Chem. Engrs. 39 (1961) 280.
  b. Bourke, P. J. and D. Pepper: Trans. Instn. Chem. Engrs. 41 (1963) 40.

10. Olefins
  i. Absorption of isobutylene in aqueous solutions of $H_2SO_4$ for the manufacture of tertiary butanol and for polymerization to di-iso and tri-isobutylene; see Gehlwat, J. K. and M. M. Sharma; Chem. Engng. Sci. 23 (1968) 738.
  ii. Absorption of isobutylene in phenols and substituted phenols in the presence of $H_2SO_4$ as a catalyst for the manufacture of the corresponding alkylated products;
    a. DeJong, J. I.: Rec. Trav. Chem. 83 (1964) 469.
    b. Whitney, W.: Ind. Eng. Chem. 35 (1943) 264.
    c. Jelinek, J.: Chem. Prumysl 9 (1959) 398; C. A. 54 (1960) 8696.
  iii. Absorption of butadiene in cuprous ammonium complexes; see Morrell et al., Trans. A. I. Chem. E. 42 (1946) 473.
  iv. Absorption of butenes in sulfuric acid for conversion to secondary butanol; see Rustanov, K. R. and N. M. Chirkov: Zhur. Fiz. Khim. 30 (1956) 261; C. A. 50 (1956) 11081.
  v. Absorption of acetylene in aqueous CuCl solutions to convert it to vinyl acetylene; see Marshall Sittig: Organic Chemical Process Encyclopedia, Noyes Develop. Corp., U.S.A., 1967.
  vi. Absorption of ethylene in benzene to produce ethyl benzene using $AlCl_3$ catalyst; see Marshall Sittig: Organic Chemical Process Encyclopedia, Noyes Develop. Corp. U.S.A. 1967.
  vii. Absorption of acetylene in arsenic trichloride dissolved in $C_2H_2Cl_4$ for the manufacture of chlorovinyldichloroarsine; see Whitt, F. R.: Brit. Chem. Eng. 12 (1967) 554.
  viii. Absorption of ethylene in sulfor mono- or dichloride dissolved in benzylchloride for the manufacture of dichlorodiethysulfide; see Whitt, F. R.: Brit. Chem. Eng. 12 (1967) 554. (Some other examples are also given in this paper).

11. $SO_2$
  i. Absorption of $SO_2$ in aqueous solutions of $NaHSO_3$ and $Na_2SO_3$ in the presence of zinc dust to manufacture dithionite; see Suzuki, E., E. O. Shima, and S. Yagi: Kogyo Kagaku Zasshi 69 (1966) 1841.
  ii. Reduction of $SO_2$ in $SO_3 = /HSO_3$ - buffer by NaHg amalgam.
  iii. Absorption of $SO_2$ in aqueous solutions of $NaNO_2$ and zinc dust for the manufacture of hydroxylamine.

12. HCl and HBr
  i. Absorption of HCl and HBr in higher alcohols for the manufacture of the corresponding alkyl halide (e.g., lauryl alcohol to lauryl chloride or bromide); see Kingsley, H. E. and H. Bliss, Ind. Eng. Chem. 44 (1952) 2479.
  ii. Addition of HBr to alpha-olefins for the manufacture of alkyl bromide (with terminal bromine atom), e.g. methyl undecylenate reacting with HBr.
  iii. Addition of HCl to vinyl acetylene for the manufacture of chloroprene.

In lieu of a conduit having multiple turbulence causing devices therein, additional embodiments include abruptly changing the diameter of a pipe or flow conduit as well as the provision of a manifold takeoff. Either of these will help to reduce the total system length otherwise required for thorough mixing and hence greatly reduce the physical space required. Considering the abrupt diameter change, a turbulence causing device such as a flat plate orifice is preferably located in of a constant diameter pipe which is connected to a constant diameter pipe or flow channel of a larger diameter. For example, a 4 foot pipe with a flat plate orifice at the end thereof of diameter ratio sufficient to remove the boundary layer fully may be connected to a 7 or 8 foot diameter pipe. Such an orifice at an abrupt change in diameter ensures thorough mixing and hence suppression of any radial concentration gradients. In such a situation, any subsequent downstream turbulence causing device preferably being at a distance of at least 40 pipe or conduit diameters.

Considering the manifold arrangement, it consists of a pipe or flow conduit which is abruptly converted into several pipes of smaller diameter with a larger overall total conduit flow area if it is desired to maintain the same pressure drop per foot as for the large conduit. For example, a single 4 foot diameter pipe may be abruptly transitioned by manifolding into 24 one foot diameter pipes. The first turbulence causing device such as a flat plate orifice is preferably located in each manifold relatively near the conversion from a single pipe into the multiple pipes. According to such an embodiment, the transition length may be reduced from 40 diameters, i.e. 40 × 4 feet to 40 × 1 foot, a reduction of 120 feet. Of course, other turbulence causing devices may be located downstream as before.

Regardless of type of alternate embodiment in point, the admission of a treating fluid may be carried out in accordance with the above set forth disclosure.

In the conveying of fluid from one area of the system such as a treating portion to another area, the diameter of the flow channels may be changed, as desired. For gradual transitions to decelerate subsonic flow, the diffuser transition should not exceed a taper of approximately 7° to ensure that boundary layer separation is suppressed. This slope is not critical for transition nozzles which accelerate subsonic flow.

Preferably, following a fluid phase treatment station, including downstream mixing as through second or third turbulence causing devices, a contact chamber may be provided. The purpose of such a chamber is to extend the detention time of the treated fluid after ideal mixing has been developed.

OZONE PRODUCTION

According to the concepts of the present invention, an improved process for the production of ozone may be utilized. In general, an ozonator requires a feed of oxygen containing gas, a voltage potential and a minimum amount of pressure. Upon application of the voltage, oxygen in the feed gas which is under pressure is partially converted to ozone. It is known that the production of ozone can be maximized at high gas feed rates. These yield relatively low ozone in gas concentrations. It is also known that ozone can be produced by varying the feed rate of oxygen and the voltage. It has been found that this can be done in such a way so as to maximize the ozone concentration which may be dissolved in a treated fluid. To do this requires a departure from standard teaching. A sacrifice is required in the electrical energy consumption in kilowatt hours per pound of ozone produced. Specifically, the feed rate or amount of oxygen containing gas fed into the ozonator is reduced to the minimum required amount and the voltage is increased to the maximum amount possible with the particular unit. The effect is to obtain less than maximum or rated ozone production.

However, this sacrifice in ozone production is more than offset by a gain in efficiency of gas liquid injection and mixing derivable in the following step. This mode of operation of an ozonator enhances ozonation by allowing higher ozone concentrations in a treated fluid within the limit of the saturation quantity of any component of the carrier gas in the treated fluid. For example, on air feed, an ozone air concentration of 2.5% is possible. From air, the nitrogen solubility in water is 18 ppm at atmospheric pressure. The air feed is proportioned to provide this quantity of nitrogen. The quantity would be 22.5 ppm of air, of which 2.5% would be ozone. The $O_2$ and $O_3$ fed would stabilize at 4.5 ppm oxygen unless oxidation reactions deplete the ozone. The corresponding ozone concentration in the treated fluid would be 0.56 ppm. Ozone-fluid solutions are bactericidal and viricidal at ozone concentrations of 0.50 ppm or greater. Thus, this technique achieves disinfection without entailing an inherent loss of ozone in gas blown (e.g. nitrogen) through the fluid system owing to gas-fluid saturation in the treated fluid. It should be recognized that gas feeds at rates above these corresponding to saturation of any gas component in the fluid will and must be followed by gas blow through. In blow through, ozone and non-saturated components of gas will be lost. It follows that the operating principle is to feed gas or gas mixtures at the lowest possible rate, preferably at component gas saturation limits or less. Potential loss of ozone from inefficient gas-fluid mixing is many times greater than the loss in ozone productive capacity induced by ozonator operation at maximum practical ozone in oxygen containing gas concentrations. Recognizing this, it follows that ozonator improvements focused on sustaining kwh/pound of ozone produced at maximum possible ozone concentrations in oxygen containing gas are most desirable. The ozone, of course, can be used in any subsequent process such as in sewage or waste treatment plants hereinabove described as well as for any other conventional uses. The important factor is that the process only requires the smallest possible amount of oxygen as feed so that upon the application of the voltage, a maximum concentration and amount of ozone is produced.

OZONATOR CHARACTERISTICS

Production Rate

The production rate of an ozonator depends primarily upon the applied energy. Operating controls usually provide for a broad range of input gas flow. The gas must contain oxygen. An increase in oxygen concentration to twice that for air approximately doubles the ozonator production rate. For a 100% oxygen feed, little increase in production rate is observed above that for oxygen-enriched air at 40% oxygen concentration.

As the gas feed rate to an ozonator increases, the ozone concentration in the ozonated output flow decreases. The decrease is almost exactly inversely proportional to the input gas feed rate. Thus, for a gas feed rate $W_g$ in pounds per minute and an ozone concentration, C, in parts per million, in the output gas, the ozonator production rate, $W_o$ in pounds per minute is almost a constant. This is shown in the FIG. 30. Note there that the volumetric feed rate is used instead of the weight feed rate. However, the relationship on log-log coordinates is almost linear. The relationship, $$W_g \cdot C = W_o$$

as defined before, would plot as a straight line. The dotted line illustrates this relationship.

The illustration also shows how a reduction in energy supplied to the ozonator can reduce the production rate of ozone. Practicably, this is the only control on ozone output except for a change in oxygen enrichment of the ozonator feed gas.

Figure 36:
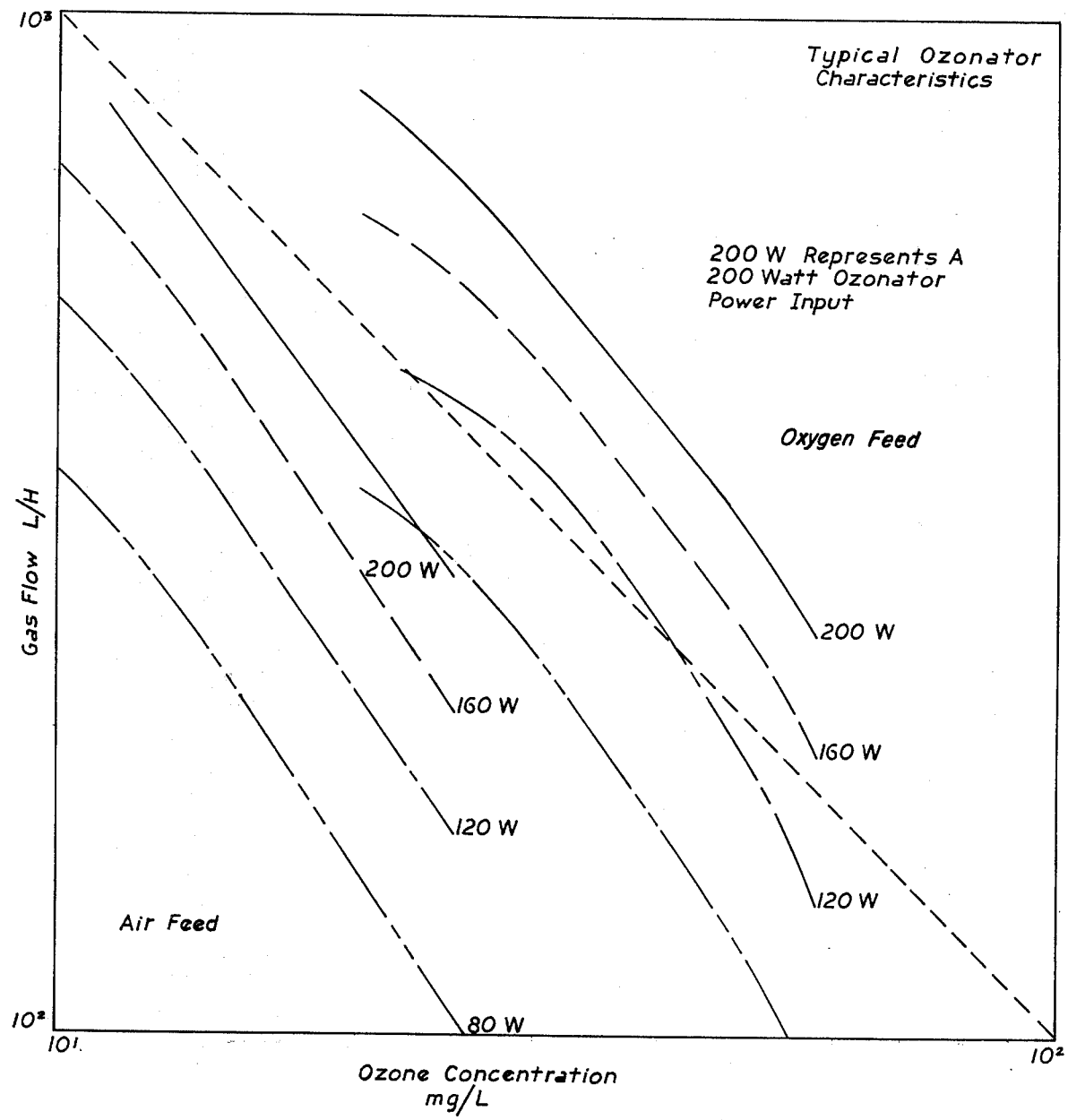
FIG. 36 is a graph showing energy requirements for ozonation only.

FIG. 36 also shows energy requirements for ozonation only. Additional energy is required to dry and compress the ozonator feed gas. From preceding discussion, it is apparent that maximum ozone production occurs near the mid-range of any plot. However, ozone production at the lowest range of any plot is not materially less than that for the maximum condition. This lowest range of gas feed rate corresponds to the maximum ozone concentration. Elsewhere in this specification, it has been indicated that gas-liquid mixing efficiency is potentially greatest at the highest ozonator output ozone concentration achievable. Thus, overall ozone-applied efficiency is derivable by ozonator operation at minimum gas flow feed rates. These compromise ozone production slightly. The compromise is more than compensated for by the improved injection-mixing efficiency.

Further, under this recommended mode of operation, the total energy required per pound of ozone generated and applied within the overall system is reduced. This is so owing to the marked reduction in feed gas drying and compressing energy which is necessary at minimized ozonator gas feed rates. One factor which contributes to this fortuitous circumstance is the moderate effect of nitrogen in ozonator feed gas on production rate. To about 60% nitrogen in oxygen of the feed gas, nitrogen does not materially degrade the ozone production rate.

Considering the total electrical energy input into the overall system, instantaneous current of any alternating current is given by the formula $i = I_m \sin 2ft$. Of course, Ohm's law states that voltage is equal to the resistance times the instantaneous current. Thus, voltage is given by the following formula, $e = RI_m \sin 2ft$, where $i$ is the instantaneous current in amperes at any time, $I_m$ is the maximum current amplitude, $f$ is the frequency in cycles per second, $t$ is the time in seconds and R is the circuit resistance in ohms. Since power is the voltage times the current or the current squared times the resistance, the power in watts can be readily calculated. Similarly, energy is power times the time, usually expressed in watt hours. Of course, in calculating the power over a period of time, rather than using an instantaneous current value, of course, as is well known to one skilled in the art, the root mean square value is used. From the above formulas, it is clear that either energy or power in a circuit may be regulated by voltage or frequency variation. It is also further quite clear that the preferred ozone production can be readily increased as the electrical frequency is increased. However, it has been found that regulation of ozone production based on voltage alone is severely limited by non-linearity and is therefore restricted in range of applicability. A preferred technique is to use a variable frequency power supply as from a motor generator or a solid state variable frequency power supply and to rely upon superimposed voltage control for only secondary regulation.

According to any standard conventional text, such as "Ozone in Water and Waste Water Treatment" by Evans, Ann Arbor Science Publishers, In., page 103, the yield of ozone per unit area, Y/A, is given by the following formula: $Y/A$ $fep^2g^2/d$ where $f$ is the frequency of the applied voltage, e is the dielectric constant, $p$ is the gas pressure in a gap, $g$ is the gap width and $d$ is the thickness of the dielectric. The voltage (maximum) $E_m$ is proportional to the product of pressure and gap width. Thus, these equations indicate that ozone production per unit is proportional to voltage squared and is linearly proportional to the frequency. Thus, ozone production in the present system can be maximized by increasing the voltage, frequency or the gas pressure.

A correlation is thus found in FIG. 36 wherein increased ozone production is obtained at higher wattages (power). Since wattage is proportional to the product of voltage times amps, it is dependent upon shift of frequency and resistance as set forth in the above formulae.

It is useful to consider the comparative performance of an ozonator on oxygen enriched air feed at the recommended low gas feed rate with that for the normal flow rate. The comparative ozone concentrations are 55. mg/l and 25. mg/l. These correspond to ozone concentrations in the ozonated gas output of 4.6% and 2.1% respectively.

This comparison appears in the table which follows. There, the production rate column shows the ozone output is slightly greater at the relatively low concentration of 2.1%, 25. mg/l. This occurs at the highest feed gas rate. The specific energy column reveals that this high gas rate corresponds to high energy penalties for drying and compressing the ozonator feed gas.

Compare these conditions for those for production at 55. mg/l, or 4.6% ozone concentration in the ozonator output. There, the lowest ozonator feed gas rates prevail. At 200 watts, the ozone production rate is 14.6 g/h at low gas rates. It is 17.3 at the high gas feed rates. This is a reduction of about 16%. However, the specific energy for the low gas rate is 8.5 kwh/lb. The high gas rate exhibits a specific energy of 11.3 kwh/lb. The reduction in specific energy is 25%. It is logical therefore to sacrifice 16% in rated production for a 25% saving in energy.

In addition to this economic advantage, the high ozone concentration enables markedly increased ozone input to the treated fluid. Thus, the overall system efficiency is increased greatly while the energy requirement is reduced 25%. Finally, the oxygen-enriched air feed gas contributes further advantages.

| TYPICAL OZONATOR AND FEED Gas DRYER-COMPRESSOR CHARACTERISTICS | | | | | | | |
|---|---|---|---|---|---|---|---|
| | | | Ozone | | Specific Energy, kwh/lb | | |
| Feed Gas | Gas Rate, l/h | Ozonator Setting Watts | Concentration, Co, mg/l | Production Rate, $W_o$ g/h | Ozonator | Gas Dry-Compress | Total |
| Oxygen Enriched Air, 40% Oz | 265. | 200. | 55. | 14.6 | 6.2 | 2.3[(1)] | 8.5 |
| | 207. | 160. | 55. | 10.4 | 7.0 | 1.8 | 8.8 |
| | 152. | 120. | 55. | 8.4 | 6.5 | 1.3 | 7.8 |
| | 98. | 80. | 55. | 5.4 | 6.7 | .8 | 7.5 |
| " | 480. | 200. | 35. | 16.8 | 5.4 | 4.1 | 9.5 |
| " | 382. | 160. | 35. | 13.4 | 5.4 | 3.3 | 8.7 |
| " | 307. | 120. | 35. | 10.7 | 5.1 | 2.6 | 7.7 |
| " | 194. | 80. | 35. | 6.8 | 5.3 | 1.7 | 6.0 |
| " | 694. | 200. | 25. | 17.3 | 5.3 | 6.0 | 11.3 |
| " | 550. | 160. | 25. | 13.7 | 5.3 | 4.7 | 10.0 |
| " | 419. | 120. | 25. | 10.5 | 5.2 | 3.6 | 8.8 |
| " | 292. | 80. | 25. | 7.3 | 5.0 | 2.5 | 7.5 |
| 282. | 200. | 25. | 7.0 | 13. | 2.4 | 15.4 | |
| " | 208. | 160. | 25. | 5.2 | 14. | 1.8 | 15.8 |
| " | 158. | 120. | 25. | 3.9 | 14. | 1.4 | 15.4 |
| " | 104. | 80. | 25. | 2.6 | 14. | 0.9 | 14.9 |

Oxygen enrichment at 40% oxygen, 60% nitrogen almost doubles ozonator production compared to production on air.

Less oxygen enrichment is proportionately beneficial. One particular enrichment is of interest. In this specification, it has been noted that air-saturated water exhibits a dissolved gas distribution of one part oxygen to two parts nitrogen 9 ppm and 18 ppm at atmospheric. This has shifted from the input gas distribution, in air, of one part oxygen to four parts nitrogen at atmospheric pressure.

It might be expected that oxygen enrichment of air to 33% oxygen, 66% nitrogen would be in equilibrium with the one to two ratio noted above. This is not so. As the oxygen concentration in the fluid saturating gas increases so does the oxygen concentration in the dissolved gas. For this reason, the preferred range of oxygen-enriched air feed for ozonation is from one-third to two-fifths oxygen.

Under these conditions, recycling of the desorbed ozonated carrier gas is possible at minimum oxygen feeds to sustain desired enrichment of feed gas. This mode of ozonator operation, i.e. low feed gas flow, recycling, high ozone concentration and possible oxygen enrichment of air feed comprises the optimum overall system for generating and dissolving ozone in treated fluids. These system operating conditions are optimum in terms of overall cost of ozonation per unit weight of ozone dissolved in the treating fluid.

In the foregoing system particularly with self enrichment of oxygen, small quantities of oxygen makeup may be required. This may be supplied from on-site oxygen generators, from LOX storage or from gas-phase storage. Since the equilibrium concentrations of dissolved gas in air-saturated water are 33% oxygen, 66% nitrogen an alternative source of makeup feed gas is possible. Pressurized water is saturated with air. The saturated water is decompressed. Desorbed gases are recovered. These gases will be comprised of 33% oxygen and 66% nitrogen. They represent a near ideal ozonator feed gas. This feed gas could be enriched with oxygen, if desired.

SELF ENRICHMENT OF OXYGEN

Figure 37:
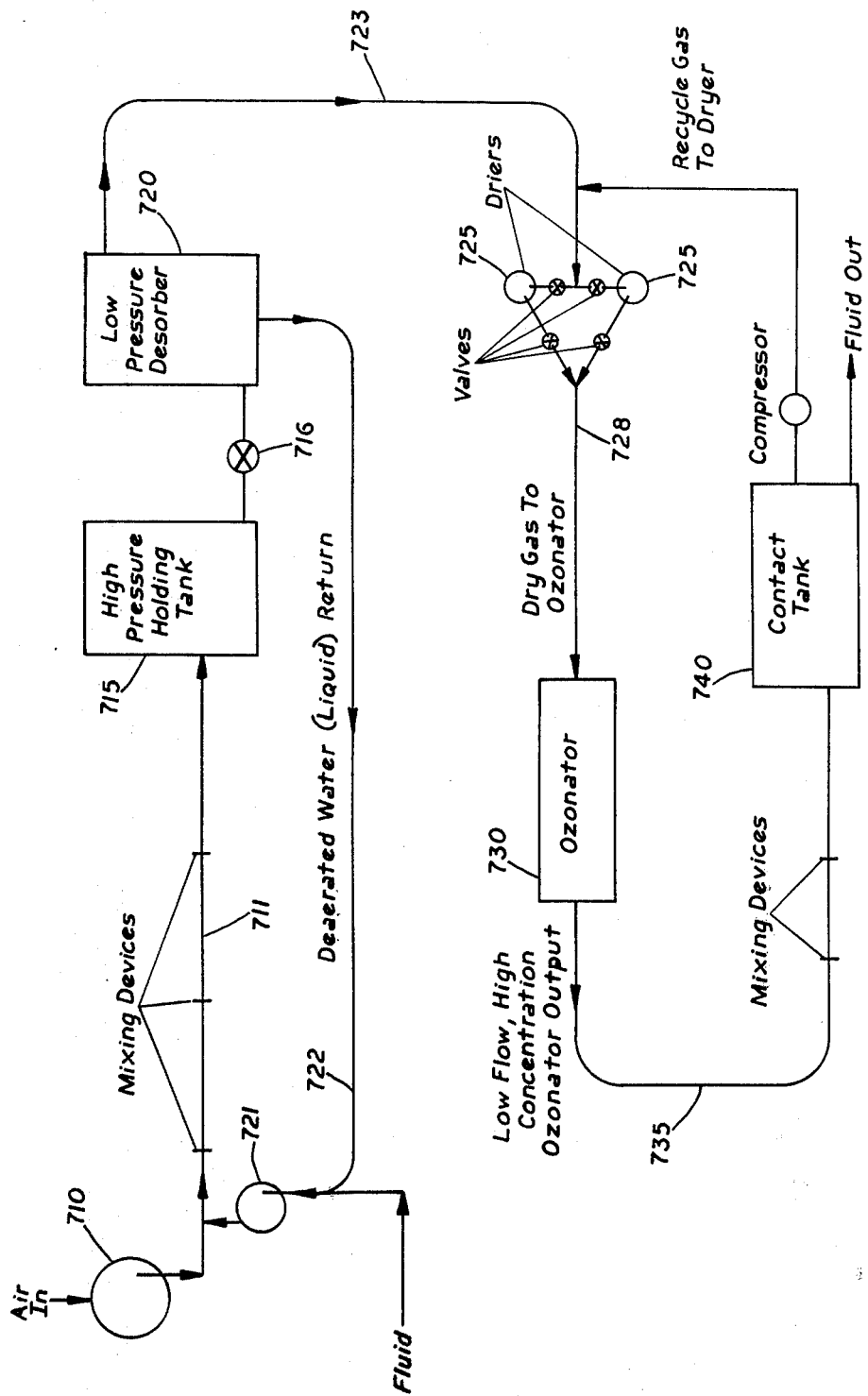
FIG. 37 shows a typical system for the production of ozone.

A typical system for the production of ozone is shown in FIG. 37. Numeral 710 is a compressor which feeds the fluid, preferably air through a length of piping containing turbulence producing devices to ensure complete mixing such as flat plate orifices as set forth hereinabove separated by at least 40 pipe diameters. The fluid is then held in a high pressure tank 715 which contains an atmosphere rich in nitrogen. The fluid is then fed through an expansion valve 716 which may be a hydraulic turbine generator to recover energy in the form of electrical or mechanical energy to a low pressure desorber 720 which contains an atmosphere rich in oxygen. Each tank contains gas-saturated water. Part of the water from the second or low pressure desorber is recycled or wasted through a pump 721 and pipe 722. The desorbed gas, oxygen-enriched air is then fed via line 723 to dryer 725 which may be silica beds wherein the oxygen-enriched air is alternatively fed to one tank and not the other. This procedure is generally preferred to drying by refrigeration to lower the dew point. With respect to the liquid in tank 715 and 720, water may be utilized as noted but generally any liquid having higher solubility for oxygen than nitrogen may also be utilized. The oxygen-enriched air, after drying, is then fed to an ozonator 730 as hereinabove described via pipeline 728. The fluid containing a high concentration of ozone is then fed to a contact tank 720 via a pipeline 735 wherein mixing devices are contained such as flat plate orifices. After the contact tank, part of the gas or fluid is recycled to the dryer whereas the liquid in the contact tank such as water may be pumped out at will.

ROTARY DISTRIBUTOR ARM AND NOZZLE FOR TRICKLING FILTER

In a trickling filter, the bed beneath the distributor arm should be dosed with liquid at a uniform flow over its area, expressed in gallons per square foot per day. A usual maximum rate is 1,000 gallons per square foot per day. It is necessary for efficiency and economy of operation that the dose rate be uniform with radius at any impressed total flow on the system. The reason for this is that any impressed flow rate, the flow from the distributor must dose the trickling filter media with equal quantities of flow per square foot of surface. Since the surface of the filter goes up as the square of the radius it is understandable that the flow is going to have to go up quite a bit at the outside edge. Unless some provision is made for channeling the flow, the tendency in an actual operating filter is to make the flow distribution speed dependent. This will tend to unwater the central section of the arms and to shift major flow towards the outer radii of the distributor arm. It is particularly a problem to ensure uniform flow at high flow rates.

Figure 20:
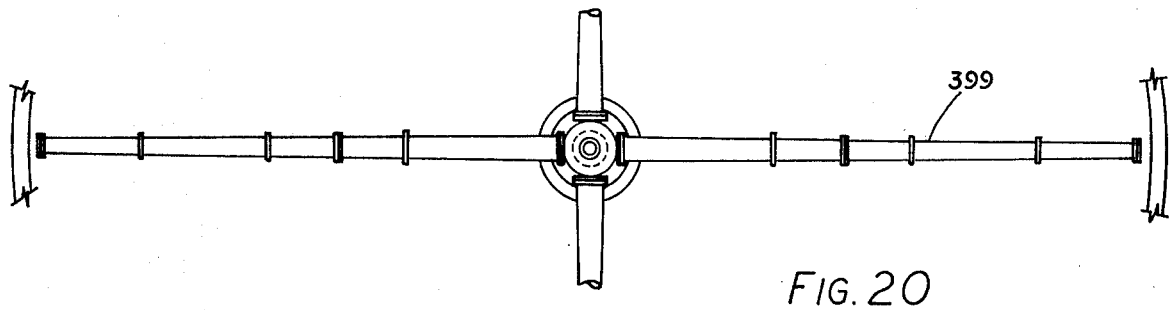
FIG. 20 is a plan view of a large diameter distribution arm and its rotating support post.
Figure 21:
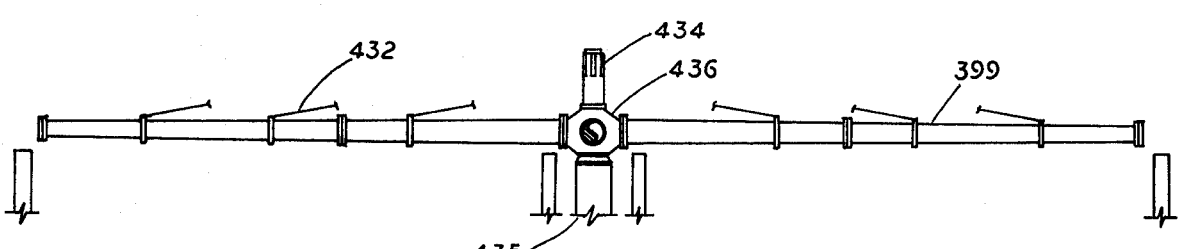
FIG. 21 is a front elevational view of the distribution arm of FIG. 20.
Figure 22:
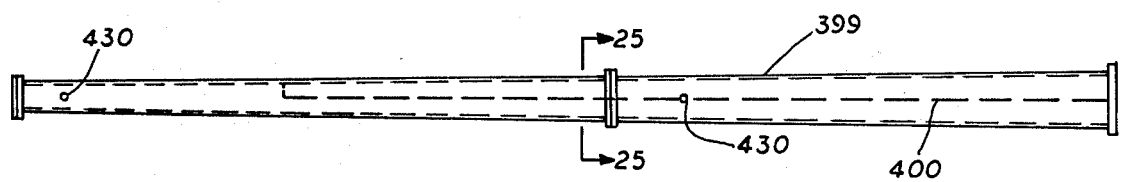
FIG. 22 is a plan view of the arm alone indicating some of the internal structure in dotted lines.
Figure 25:
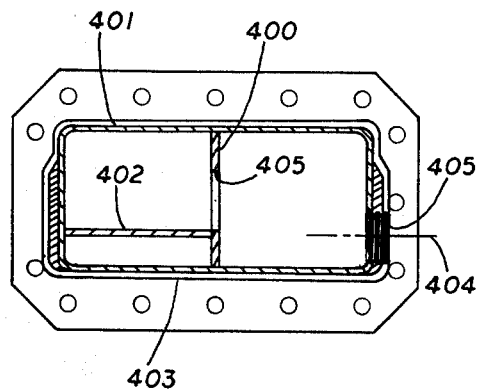
FIG. 25 is an enlarged cross-sectional view taken on line 25—25 of FIG. 22.

Now referring particularly to FIGS. 20 – 23 of the drawings, the distributor arm is indicated by number 399. A dotted line 400, as seen in FIG. 22 runs down the centerline of arm 399, and this represents a closure which isolates a channel allowing only half the total channel to be available for flow in the filter distribution arm for a lower portion of the section. FIG. 25 better shows the cross-sectional configuration, and clearly indicates the divider section 400, as well as a horizontal divider section 402 which will be discussed in further detail hereinafter. Note in FIG. 25 that the upper surface of divider 402 is at substantially the same level as the centerline 404 of the orifice opening 405 (orifice 410 not shown in FIG. 25). The orifice locations are present in the maximum number for which space is available and they allow effluent to be removed from the distributor arm.

Now with reference to FIG. 25, the construction is provided to isolate the flow of effluent until the level builds up to the top surface of divider 402. First in considering this buildup of level, it must be assumed that flow occurs at a variable rate as it is distributed by the distributor arm. This flow rate depends on the rotative speed of the distributor arm. A usual maximum rate is 1,000 gallons per square foot per day. However, by doubling the width of the channel above the divider 402, what has been achieved is in effect allowing a further increase in flow to occur with a reduced change in level on the discharge orifice. This reduces the range in one variable. Other means that may be used to vary the distribution rate are to vary independently the diffusing nozzle to improve control of thrust, speed of rotation and diffuser flow such that the dose rate is uniform with the radius at any impressed total flow. Hence, unless some provision is made for channeling the flow, the tendency in an actual operating filter is to make the flow distribution speed dependent. Therefore, I have found that by blocking off the lower part of the section by divider 402, the flow at low rate is ensured and it reduces the effect on speed of increased flow at high rates by accommodating it with a smaller change in head on the diffuser nozzles in either set.

Figure 23:
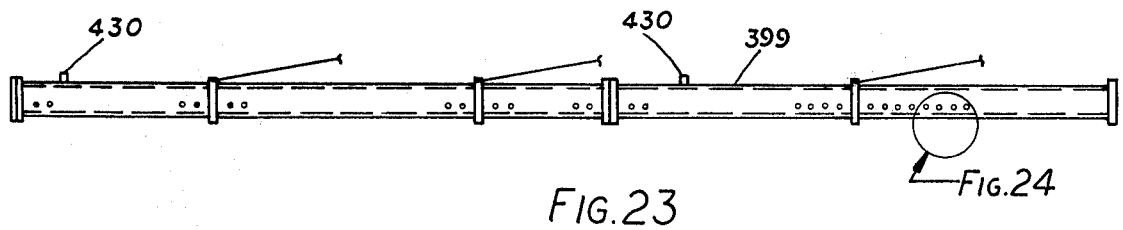
FIG. 23 is an elevational view of the arm of FIG. 22.
Figure 24:
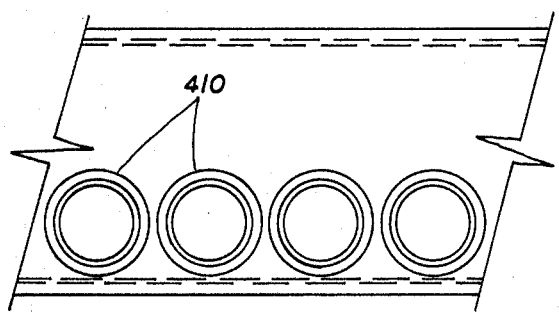
FIG. 24 is a broken away enlarged view of the nozzle arrangement taken from the circled area of FIG. 23.
Figure 28:
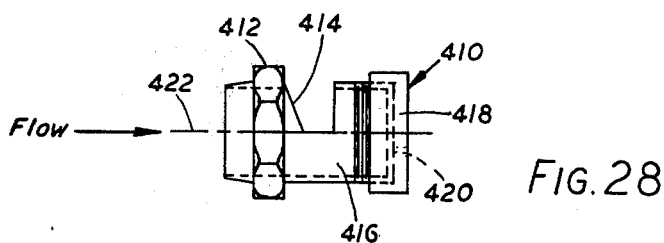
FIG. 28 is an enlarged elevational view of the diffusing nozzle utilized in the distributor arm of FIGS. 20 – 23.

An additional feature of the distributor arm 399 which is interesting is that its diffusing orifices indicated generally by numerals 410 and shown in FIG. 24 are positioned at various locations along the length of the distribution arm in FIGS. 22 and 23, are variable in elevation that is, the flow passage elevation can be modified by rotating the orifice. In this way, depending on orifice configuration, rotation may be used to vary the head and flow or momentum change. The momentum change develops thrust. This effects distributor speed. Speed affects the head along the distributor radius. Thus, it is important to be able to change head, flow and momentum changes in an orifice independently, and the orifices 210 as seen in FIG. 28 incorporate a hex nut 212 to allow the orifices to be mechanically rotated to vary the direction of their thrust.

Figure 29:
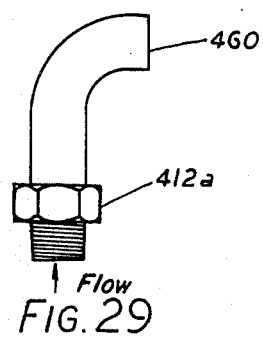
FIG. 29 is a side elevational view of an alternative sweep elbow that might replace the diffusing nozzle of FIG. 28.
Figure 30:
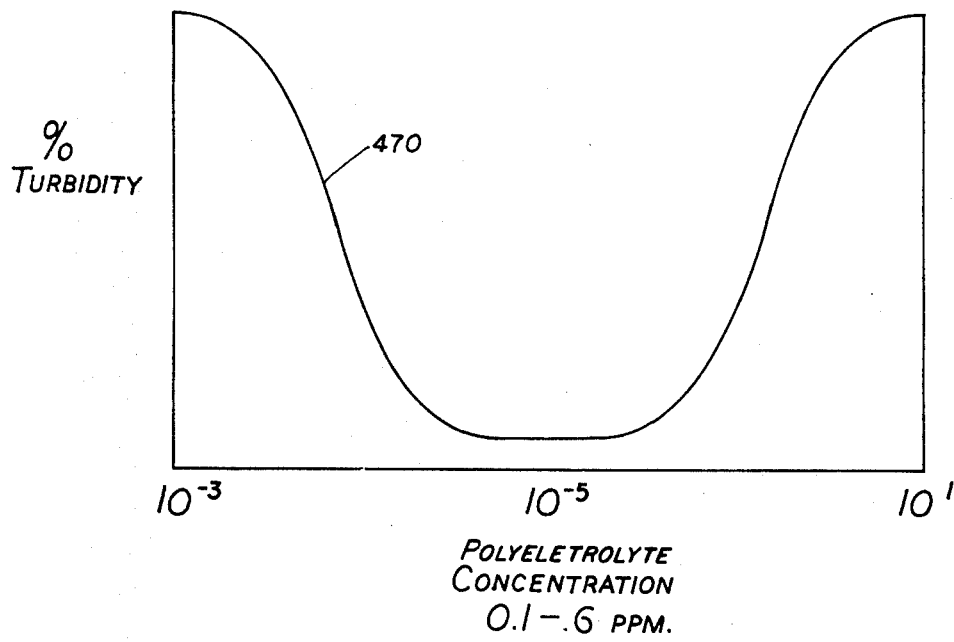
FIG. 30 is a graph illustrating optimum concentrations of polyelectrolyte feed for maximum removal of suspended matter.

FIGS. 29 and 30 represent a modified orifice comprising a 90° elbow. This may again be rotated by means of the hex nut 212a either using a wrench or hand pressure. It may be rotated to discharge vertically upward or downward. The head and flow would thereby be varied greatly. The change in momentum would be a function of the velocity of the liquid, as well as the angular position of the orifice.

Again referring to FIG. 28, each nozzle 210 incorporates a slot 214 milled into a circular pipe section 216 comprising the nozzle. Further, a rotatable end cap 218 has a slot 220 cut therein so that in effect two separate slots for control purposes are available. Preferably the slot 220 is elongated and circular on the ends but as it can be seen it is eccentrically offset from the centerline 222. Thus by rotating the slot 214 upwardly, the flow is reduced because the head is reduced. In this instance as shown in FIG. 28 there may be more flow coming out the slot 220, but none coming out of the slot 214. Now again looking at the slot 214, if this is rotated down, then the slot 220 in the end of the cap will be rotated up so that there is no flow directly out the end of the cap, but all or substantially all of the flow drops down onto the filter bed from the slot 214 in the short nipple section of the nozzle. Considering the desire to change independently the relative flow and the propulsive effort at the same time, this is possible by mutual changes in the angular settings of the two rotatable elements, namely cap 218 and nut 212 and pipe section 216 which comprise the nozzle 210.

The rotation of the nozzle elements can be done manually, but most conveniently it can be done using an appropriate wrench. Primarily the idea of adjusting the angular position of the slots for flow control is to accommodate changes in flow which occur progressively on a plant, usually towards an increasing flow, which would occur over a long period of time, rather than daily incremental changes without affecting the radial uniformity of dose to the filter bed.

It must also be understood that the speed of the distributor arm is important in that the distributor rotates by reason of propulsion effort. As the speed changes, an effect on the pressure distribution in the distributor arm occurs. This is apparent from the fact that the liquid surface in a rotating vessel in paraboloidal. Thus, the virtual head approaching the distal tip of the distributor is higher than that at the center by the difference in magnitude of the paraboloidal ordinates. The general effect of the increased head towards the distal tip of the arms would be to increase the flow disproportionately in that region. This is one reason why measures were taken with respect to the nozzle slots to control the rotative speed of the distributor, and also the measures to control the flow channel as seen in FIG. 25, which was discussed above. Therefore, this distributor in the embodiment shown in these drawings will accommodate with independent means and provide the adjustment necessary to achieve the basic objectives of making uniform over the flow range and distributor radius the proper flow distribution per unit area of receiving media below the arm.

As a further result the rotatable cap 418 facilitates cleaning of material which may become entrained in the orifices or slots 414 and 420. It should be noted with respect to FIG. 24 that the nozzles 410 are actually placed in the closest possible spacing such that the number of slots or orifices which are inserted into an arm may be maximized.

A further point that should be noted with respect to FIGS. 20 – 23 is that the nozzles appear on the upstream face of the distributor arm as well as on the downstream face, and this is seen in FIGS. 22 and 23. The purpose of the upstream orifices or nozzles is to enable further control over the propulsive effort and the speed which is developed in the distributor without compromising the uniformity of flow dosage per unit area of receiving media beneath the filter.

Another possibility with the type of distributor arm defined above is to insert instead of spray head nozzles such as shown in FIG. 28, some type of closure plug which in this way adjusts the flow independently of the orifices. That is, by removing nozzles and placing in a substitute blanking nozzle, which is a standard pipe plug, in this case, the flow can be controlled.

A further detail in the construction of the distributor is a vent to prevent the formation of a vacuum. Such vents 430 are shown in FIGS. 22 and 23.

A further feature of the structural requirements of the arm is to have tie rods indicated generally by the numeral 432 and best seen in FIGS. 20 and 21 extending from various points along the length of the arms back to the central support post 434 to support the arms in cantilevered fashion from the central distributing head 436. Such tie rods 432 compensate for horizontal forces which occur by reason of an acceleration or deceleration, and the structure of the arms themselves is that they function as a variable section-modulus, continuous beam from zero radius to the radius of the distal tip so that they are supported at independent points by the rods 432 which are adjustable so that the distributor may be trimmed when it is installed to operate in a horizontal plane with much lower stress than would occur with a cantilevered arm.

The multiplicity of tie rods and the stress analysis of such a distributor is based on approximations concerning indeterminate structures involving a continuous beam supported on three intermediate supports. It can be utilized analytically at least as a first approximation, as a constant section beam. Subsequently the analysis needs to be refined for checking. It should be strongly pointed out and is clear from the drawings that the section-modulus varies continuously along the length of these arms from a larger cross-sectional configuration near to the hub 436 to a much smaller cross-sectional configuration at the distal tip, and hence the section-modulus and the stress analysis needs to be made more sophisticated to accommodate the variation in section-modulus as a function of radius of the distributor. In other words it is a feature of the invention that the arms are tapered or decrease in cross-sectional area all the way along the whole length uniformly. The tapered configuration to the arms makes them less sensitive to changes in rotative speed of the distributor and to short term changes in distributor flow, and by constriction of the channel, suppresses the effect of getting a greater volume flow out the nozzles the further they are away from the center of the hub owing to speed effects.

Now again referring to the cross-sectional configuration of the arm which is substantially rectangular in section as seen in FIG. 25, the divider web 400 furthermore serves as a reinforcement between the upper and lower flanges 401 and 403 of the distributor arm which functions as a stiffening beam shear web. Note that the web 400 is interrupted periodically with holes through it such as at 405. These holes 405 allow fluid to enter into the upper channel of the blocked off section as well as in the normal channel.

Figure 26:
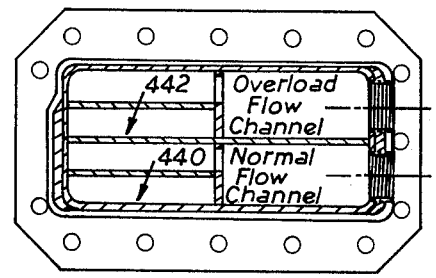
FIG. 26 is a modified double flow channel similar to that shown in cross-sectional configuration of FIG. 25.

Now referring particularly to FIG. 26, this represents the same cross-sectional configuration of FIG. 25 except substantially doubled in heighth with the blocked off regions 440 and 442 blocked in both the upper and lower channels. The upper channel (overload flow channel) is separated from the lower channel (normal flow channel) by a horizontal divider 443. The intention here is to have the upper section function under high conditions of plant flow and ensure the proper distribution of flow along the radius of the distributor regardless of the level of flow. High flow rates would normally make a trickling filter distributor rotate excessively fast. High speeds would throw the liquid out to the outside radii of the distributor making the flow distribution through the media not a constant per unit of surface area exposed. With the embodiments shown in FIG. 26, however, this distributor section would maintain approximately the same width or heighth ratio in the cross-section as in FIG. 25 for the normal distributor. In other words, the heighth and width ratio would be the same in the double channel distributor arm as in the single channel.

Figure 27:
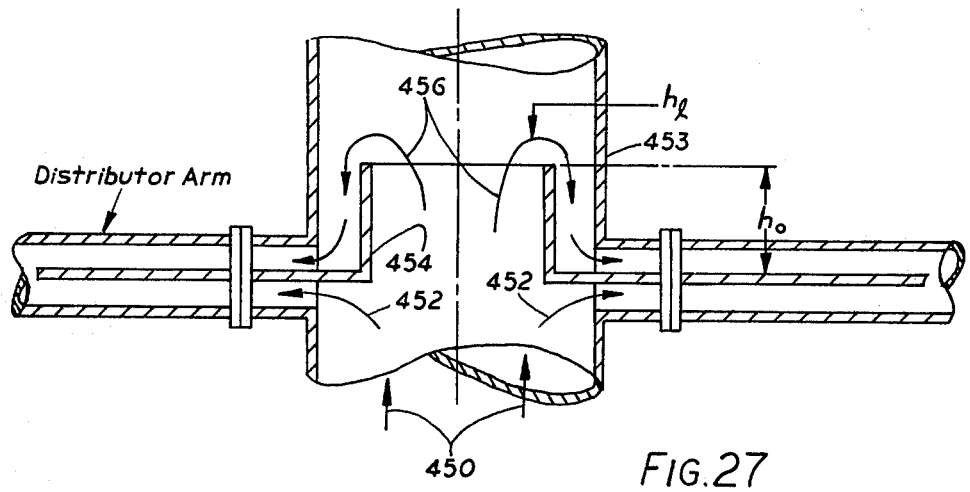
FIG. 27 is an enlarged cross-sectional view to show the flow path in the distribution head to define the double flow channel of FIG. 26.

In order to understand how the double channel or overload flow configuration of FIG. 26 would work, reference should be made to FIG. 27 where the numeral 453 represents the central column of the trickling filter with flow coming in as indicated by the arrow 450. The normal flow for the effluent will be directly into the normal flow channel of the distributor arm or as indicated by arrow 452. However, when the flow builds up over the weir type pipe section 454 overflow will occur in the direction of the arrow 456, and thence down into the overload flow channel of the distributor arm as clearly shown in FIG. 27. The weir equation that is pertinent is $Q_{cfs} \times 3.33 \times c_{ft.} \times H3/2$ ft. The sketch of the diagram of FIG. 27 indicates $h_0$ which is the weir head elevation of the weir with no flow over it. Basically the above equation gives the weir flow which would be accommodated in the upper channel when the flow overflows the overflow weir. The flow then in the lower channel or the normal flow channel would then increase less at any level of flow beyond that cutoff for the particular head $h_0$. After the head $h_0$ is reached, the overflow of the weir would pass into the upper or overflow channel in quantities or at flow rates as given by the equation. The head on the weir would be the actual head of water level of the edge of the weir which is marked on FIG. 27 as $h_1$ meaning the head of the liquid, in feet.

Hence, in summary, for a given influent head, the flow in the rotating distributor arm is governed by general things. These are the nozzles that are present such as the nozzle position, the number of active nozzles, the number of retro nozzles, and the rotative speed of the distributor.

Figure 29A:
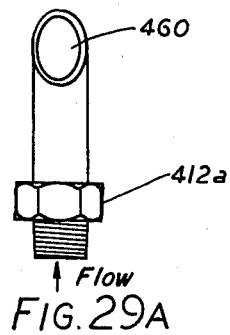
FIG. 29A is an end elevation of the sweep elbow of FIG. 29 indicating a flattened end outboard.

Referring again to the alternate sweep elbow of FIGS. 29 and 29A, the distance $e$ in FIG. 29 represents the displacement of the end of the nozzle from the centerline of input to indicate that rotation of the nozzle will change the head. It should also be seen as shown in FIG. 29A that the end of the nozzle at 460 is flattened to spread the flow of fluid upon discharge from the nozzle to accomplish an overlap in the falling streams of adjacent nozzles.

The graph of FIG. 30 illustrates a curve 470 with the ordinate representing the percent of turbidity and the abscissa representing concentration levels of polyelectrolyte feed. This curve therefore shows the optimum concentration of polyelectrolyte feed for maximum removal of suspended matter. This is important with respect to the further operative embodiments of my system which utilizes polyelectrolyte feed for removal of suspended matter.

INJECTION MIXING SYSTEM WITH CONTACT TANK

Figure 31:
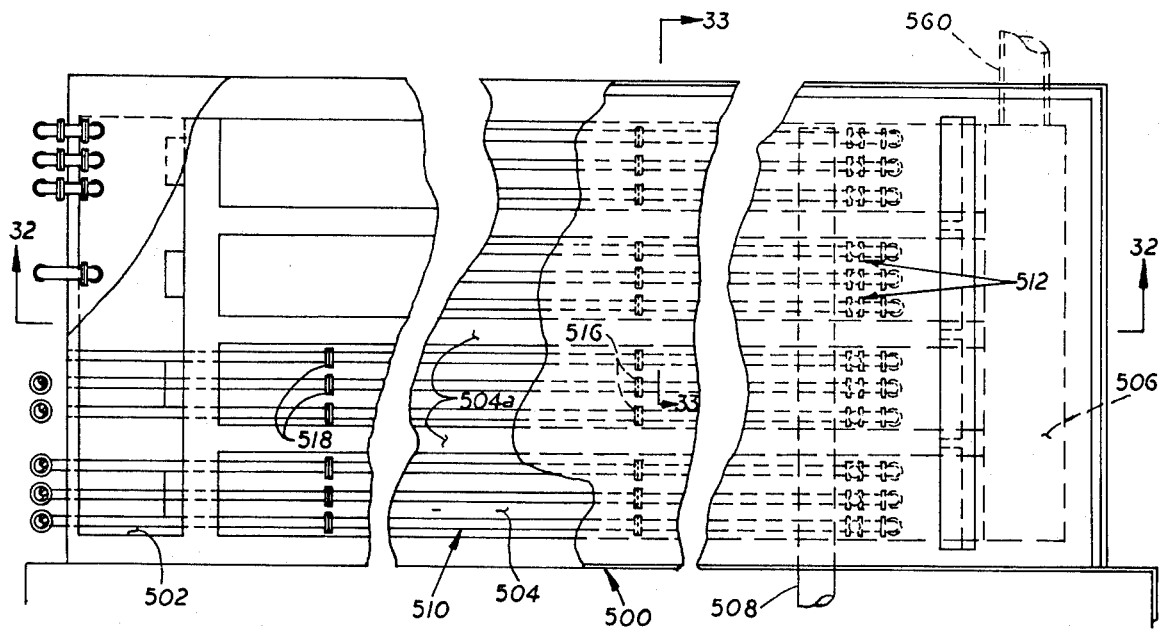
FIG. 31 is a plan view of a contact tank incorporating the preferred injection mixing system of the invention.
Figure 32:
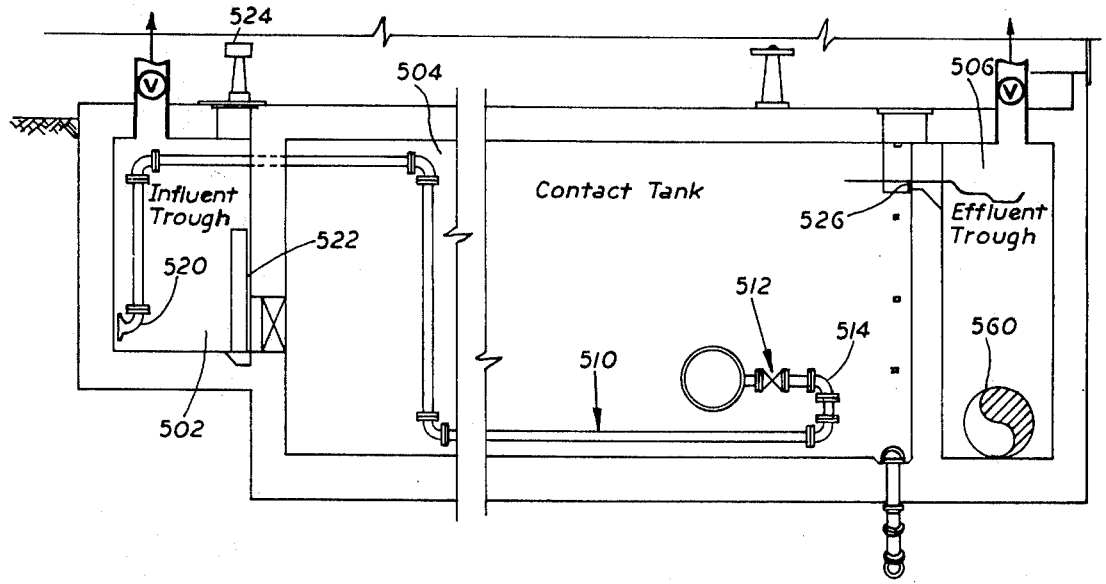
FIG. 32 is a cross-sectional view of the tank of FIG. 31 shortened in length, taken on line 32—32 of FIG. 31.
Figure 33:
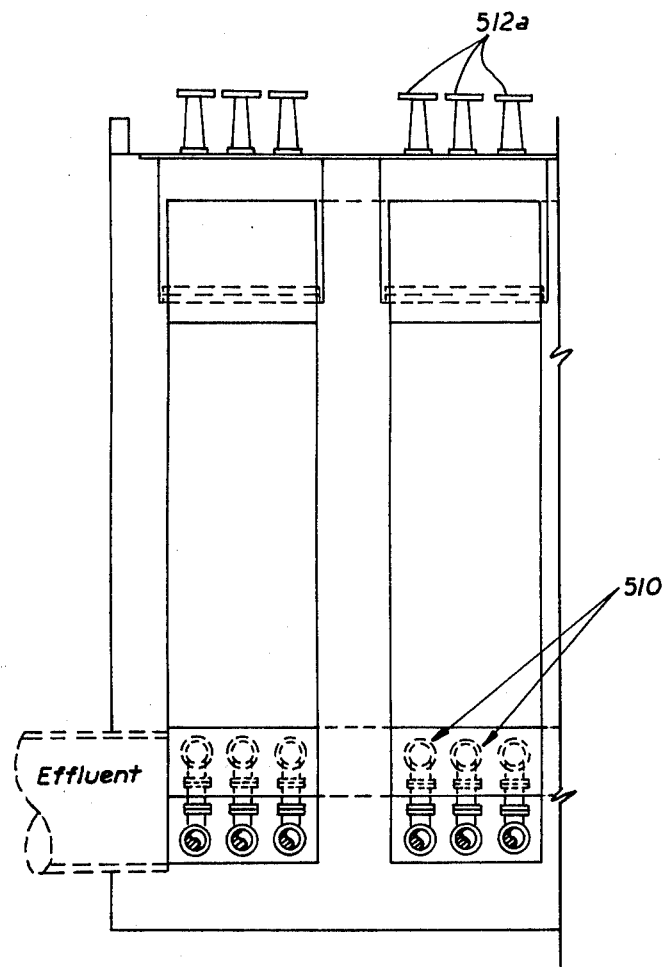
FIG. 33 is a partial cross-sectional view of the contact tank taken on line 33—33 of FIG. 31.
Figure 34:
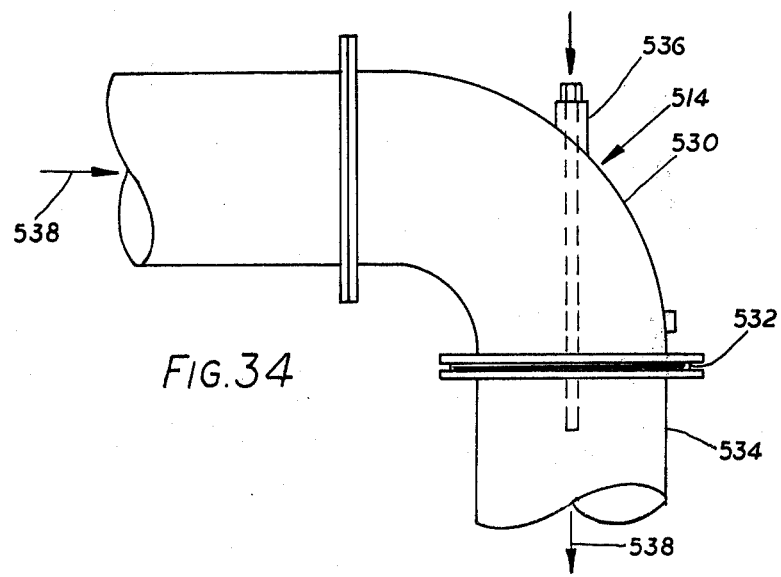
FIG. 34 is an enlarged broken away view of the injection mixing elbow utilized in the tank of FIG. 31.

The injection mixing system with a contact tank is seen in FIGS. 31 – 34 of the drawings. With reference to these figures, the numeral 500 indicates generally a large contact tank of substantially rectangular section which incorporates an influent trough 502 as best seen in FIG. 32, a contact tank or trough 504 and an effluent trough 506. An influent pipe 508 directs influent into a bundle of pipes indicated generally by numeral 510 through an appropriately valved arrangement indicated generally by numeral 512. The pipe bundle 510 receives the influent from the pipe 508 and first of all passes the influent through a respective injection mixing elbow 514, as best seen in FIG. 34, and described more fully hereinafter, and thence through downstream flat plate mixing orifices 516 and 518, and thence to the influent trough 502 for discharge thereinto through a modified hyperboloidal diffuser 520. The flow from the influent trough 502 into the contact chamber 504 is controlled by appropriate sluice gates 522, as controlled by an operator station 524 as understood by those skilled in the art. The flow from the contact tank 504 into the effluent trough 506 is over an overflow weir 526.

The details of the injection mixing elbow 514, as seen in FIG. 34 comprise a 90° pipe elbow 530 with a flat plate orifice 532 connected at the downstream end of the pipe positioned between the flanges between the elbow 530 and the next downstream pipe section 534. In order to achieve efficient mixing of ozone for example as a typical disinfection medium, injection is achieved through an injection tube 536 positioned on the axis of flow of pipe 534 but extending from the elbow 530 as illustrated in FIG. 34, this type of injection mixing being described in my above-identified earlier patents. The flow is indicated by arrows 538.

Because of the system parameters for which the particular injection mixing system shown in FIGS. 31 – 34 was designed, the influent pipe 508 was a 48 inch diameter duct and it was manifolded into twelve independent lines indicated by the pipe bundle 510. It is to be noted that the manifold is approximately 4feet 6 inches off the floor of the contact tank 504, and the pipe bundle 510 is comprised of 12-inch diameter pipe proposed to be made of polyvinyl chloride. Their centerline is located 12 inches above the floor of the tank.

In addition to the injection mixing orifice in the injection mixing elbow 514 as described above, there are 50 feet and 100 feet downstream which is 50 diameters of the pipe (anything in excess of 40 diameters being preferred) two subsequent flat plate mixing orifices 516 and provided. These are followed by a 50-foot transition length.

The influent then after having a full injection mixing through elbow 512 and flat plate orifices 516 and 518 has a uniform concentration of ozone or any other injected medium, and thence the flow proceeds to the normal influent trough location 502 at the end of the contact tank. The influent mixing lines move vertically up through the contact chamber 504 and traverse the wall between the influent trough and the contact tank. At the bottom edge of the injection mixing piping, the flow out into the influent trough 502 is through the hyperboloidal diffuser 520, which directs flow outward from the pipeline onto the wall, and which generates a hyperbolic sheet on the wall with mixing of the material presently in the influent trough 502. The resultant mixed product then traverses the sluice gates 522 into each of the four independent channels as divided by the divider walls 504*a*, and best seen in FIG. 31, in the contact tank 504.

The effluent trough 506 discharges to a 6' diameter effluent pipe 560 as seen in FIGS. 31 and 32. It should also be understood that sampling connections may be made on the pipe bundle 510 for the sampling of dissolved oxygen and pressure. Normally, the effluent channel itself would be sampled for dissolved oxygen and/or for biological testing to confirm the absence of fecal coliforms in excess of specification requirements. A typical specification requirement might be 200 fecal coliforms per 100 ml. This is a very high level and it is possible to achieve less than 2 fecal coliforms per 100 ml utilizing a one ppm concentration ozone injection at elbows 512.

Referring again to the hyperbolic diffuser 520, it should be understood that this section is a transformed hyperbolic section which decelerates the flow. The flow impinges on the influent trough wall where it mixes with the trough contents before the mixture passes through the sluice gates of the influent trough and into the contact tank proper. The diffuser 520 actually increases in area along the flow path and the elbow section in such a way as to decelerate the flow. The deceleration is intentional and is intended to produce a hyperbolic sheet on the impinging wall. The diffuser should not diverge more than 7° in the channel, otherwise boundary layer separation will occur. However, for practical economic reasons it is more convenient to use a conventional elbow diffuser instead of fabricating a special piece of equipment for this purpose. It should be understood that most of the necessary injection mixing and contact has occurred in preceeding sections of the 12 inch diameter lines i.e. the pipe bundle 510, which are the actual elements utilized for injection mixing, and contact of whatever disinfectant which is used, which may be either the ozone systems described previously, or chlorine solutions in water.

In the configuration described above with reference to FIGS. 31 – 34, the number of elements passing through the contact tank in an actual system design was proportioned on the basis of an available head of 12½ pounds per square inch, which corresponds to approximately 26 feet of water. Of the available 26 feet of water head, 16 feet of water was utilized in the actual pressure drop in the 12 foot pipes, of which there are 12, in the condition where the flow is maximum for the plant. The maximum design flow for this configuration is one hundred million gallons per day. Thus, the pressure drop is a relatively conservative figure under the circumstances and the pressure excess is available because this is a physical treatment plant. Where the pressure drop might be more conservative, the pressure could be controlled and a reduction in the number of pipes would be possible, that is in the 12 elements of pipe, by changing the diameter from, for example, 12 foot, up to perhaps 16 inches or larger. But, consideration must be given to the necessity of having preferably at least 40 diameters between mixing orifices so that the overall system length is of the order of 120 to 150 diameters.

A further limitation and consideration that must be incorporated into all plant designs is a possible requirement for de-oxygenation of the final effluent. This can be done in a number of ways. One way would be to inject sulfur dioxide, which would reduce the ozone or chlorine in the final effluent, and would thus also remove the oxygen excess present. A second possibility is to use thiosulfate, a chemical reagent which reacts with ozone and/or chlorine and will similarly reduce the oxygen or chlorine concentrations.

Either of these chemical reactions between gas and liquid may be conveniently accomplished using the process and means set forth in the GAS-LIQUID CONTACTING SYSTEMS for CHEMICAL REACTIONS section of this application. A third possibility would be to use a mechanical type de-aerator, such as a Cochrane Feed-Water Heater De-Aerator, used conventionally on boiler feedwater systems. The dissolved oxygen specification maximum disinfection system design is presently at a nominal value of 20 milligrams per liter. This would either restrict the ozone capacity available for feed, require de-oxygenation by the means set forth above, or would require oxygen-enriched air feed obviating need for deoxidation.

ACTIVATED SLUDGE AERATION SYSTEM

Figure 35:
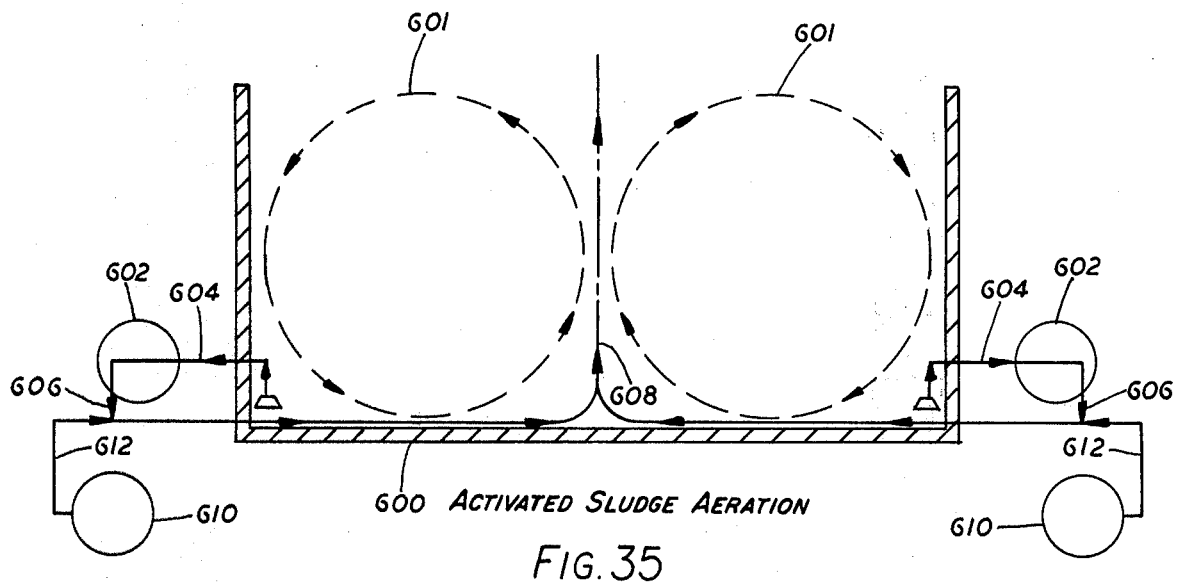
FIG. 35 is a schematic illustration of an activated sludge air injection system for an activated sludge system.

FIG. 35 illustrates an activated sludge aeration system in schematic form. It should be understood that for normal aeration in an activated sludge system approximately 15,000 cubic feet per pound is utilized, which means 100 pounds of air per pound of BOD or 20 pounds of oxygen per pound BOD. In effect represents 5% efficiency. With the system described hereinbelow, 75 to 150 cubic feet of air per pound is utilized which means 5 to 10 pounds of air per pound of BOD or 1 to 2 pounds of oxygen per pound of BOD are required. This equates to a 50% to 100% efficiency range for air injection and mixing.

Referring to FIG. 35, the numeral 600 represents an activated sludge tank. Suction is taken from one or more places on the tank near to the bottom outside edge by one or more appropriate low head, centrifugal pumps indicated by numeral 602 through suction lines 604. Pump 602 then discharges through flow lines 606 back into a substantially central and upwardly directed outlet or discharge line 608 near the bottom center of tank 600. This creates a vortex flow in the elliptical paths shown by arrows 601 and ensures that all liquid in the tank will tend to flow or move around the path. There should not be any stagnant areas.

In order to inject air then into this configuration, appropriate air compressors 610 are connected by line 612 to direct air into the discharge line 606 through approximately the same type of injection-mixing system shown in the injection elbow 514 of FIG. 34. This achieves maximum diffusion of the air within the effluent from the pumps 602, suppresses all concentration gradients, and gives an extremely efficient way of aerating the activated sludge. Normally, the pump 602 will be a low head, high volume pump which is conventionally available.

What is claimed is:

1. A two stage oxidative process for disinfection of material containing a distribution of ammonia-ammonium compounds, comprising,
    adding a primary oxidizing agent to the material to disinfect and to reduce the pH level of said material,
    said primary oxidizing agent selected from the class consisting of ferric chloride and aluminum chloride,
    adding a secondary oxidizing agent to the material to obtain a very low bacteria count and a substantial amount of ammonium compounds,
    said secondary oxidizing agent selected from the class consisting of chlorine, chlorine dioxide, ozone and sodium hypochloride,
    the amount of said primary oxidizing agent added is sufficient to cause said pH of said material to be 7.0 or less,
    said amount of primary oxidizing agent being at least 50 parts per million,
    the amount of said secondary oxidizing agent being at least 0.7 parts per million for ozone and at least 4.0 parts per million for said chlorine, chlorine dioxide and sodium hypochloride,
    said material being selected from the class consisting of sewage effluent, potable water and process water,
    the amount of said ammonium compounds to said ammonia compounds produced being at least 97 percent,
    said primary oxidizing agent being added to a first stage and, said secondary oxidizing agent being added to a second stage,
    said second stage having a conduit located therein, said conduit containing a turbulence-causing device,
    said turbulence-causing device being a flat plate orifice, an injection tube having a tip extending through said flat plate orifice,
    said tip of said injection tube being located in the vena contracta portion of said flat plate orifice, and said secondary oxidizing agent being injected into said conduit through said injection tube.

2. A two stage oxidative process for disinfection according to claim 1, wherein the maximum amount of said secondary oxidizing agent is about 10 parts per million and wherein said injection tube tip is located from about 0.25 to about 0.50 conduit diameters downstream from said flat plate orifice.

3. A two stage oxidative process for disinfection according to claim 2, wherein a conduit is located in said first stage, a flat plate orifice being located in said conduit, said first plate orifice having a diameter of from about 0.7 to about 0.9 of the conduit diameter, an injection tube having a tip extending through said flat plate orifice, said injection tube tip being located in the vena contracta of said flat plate orifice, and said primary oxidizing agent being added through said injection tube.

4. A two stage oxidative process for disinfection according to claim 3, wherein said injection tube tip is located from 0.25 to about 0.5 conduit diameters down stream from said flat plate orifice.

5. A two stage oxidative process for disinfection according to claim 4, including a final clarifier influent and effluent of a waste treatment plant, said conduit and injection tube injecting said primary oxidizing agent located in a clarifier stream selected from the class consisting of a final clarifier influent and a final clarifier effluent of said waste treatment process and said conduit and a disinfection or contact tank influent of a waste treatment plant, said injection tube injecting said secondary oxidizing agent located in said disinfection contact tank influent.

6. A two stage oxidative process for disinfection according to claim 5, wherein said pH ranges from about 6.7 to about 6.8.

7. A two stage oxidative process for disinfection according to claim 6 wherein said secondary oxidizing agent is selected from the class consisting of ozone and chlorine.

8. A two stage oxidative process for disinfection according to claim 7, wherein the amount of said primary oxidizing agent is approximately 85 parts per million.

9. A two stage oxidative process for disinfection according to claim 8, wherein said injection tube tip in said primary oxidizing conduit and said injection tube tip in said secondary oxidizing conduit is located from about 0.36 to about 0.39 conduit diameters downstream from each respective said flat plate orifice.

* * * * *

UNITED STATES PATENT OFFICE
CERTIFICATE OF CORRECTION

Patent No. 3,998,714           Dated December 21, 1976

Inventor(s)  Edward T. Armstrong

It is certified that error appears in the above-identified patent and that said Letters Patent are hereby corrected as shown below:

Column 3, line 35, change "decompostion" to --decomposition--.
Column 7, line 49, correct the spelling of the word "mathanosareina" to --mathanosarcina--.
Column 16, line 21, change the word "high" to --higher--.
Column 17, line 3, after the word "oxygen" delete the words "recovered may be".
Column 17, line 4, after the word "oxygen" insert the words --recovered may be --.
Column 19, line 9, between the words "using" and "a", delete the word "to".
Column 19, line 22, delete the word "or" after the word "enriched" and before the word "air".
Column 19, line 63, correct the spelling of the word "tretment" to --treatment--.
Column 25, line 63, change the word "ration" to --ratio--.
Column 27, line 44, correct the word "used" to --uses--.
Column 32, line 19, correct the spelling of the word "commplete" to --complete--.
Column 32, line 61, change the word "designed" to --designated--.
Column 32, line 61, correct the word "use" to --used--.
Column 32, line 65, change the word "here" to --have--.
Column 34, line 61, correct the words "pump sump" to read --sump pump--.
Column 36, line 65, correct the word "ike" to --like--.
Column 37, line 22, correct the word "purifications" to --purification--.
Column 37, line 48, correct the word "condition" to --conditions--.
Column 37, line 57, correct the word "rid" to read --grid--.

UNITED STATES PATENT OFFICE
CERTIFICATE OF CORRECTION

Patent No. 3,998,714      Dated December 21, 1976

Inventor(s) Edward T. Armstrong

It is certified that error appears in the above-identified patent and that said Letters Patent are hereby corrected as shown below:

Column 38, line 44, correct the words "such gas" to read --such as a gas--.
Column 38, line 45, insert a hyphen between the words "diffuser tipped".
Column 38, line 53, correct the word "this" to --thus--.
In TABLE I, before "Reg'd, gm/hr.$^{(4)}$" insert the word --Ozone--.
Column 41, line 20, change the word "bases" to --based--.
Column 44, line 52, delete the word "of" before the words "a constant diameter pipe".
Column 46, line 43, change "C" to --D--.

In the table appearing at the bottom of lines 47 and 48, the fourth from the bottom line all the way across should be moved over one column and the word --Air-- should be inserted replacing the number "282", this number now appearing in Column 2 of the table.

Column 50, line 3, correct "720" to read --740--.
Column 53, line 26, correct the spelling of the word "heighth" to --height--; the same correction needed on lines 41 and 43.
Column 54, line 6, insert the word --two--between "by" and "general things".
Column 54, line 12, delete "e" after the word "distance".
Column 55, line 10, "there" should be --these--.
Column 56, lines 10 and 20, "12 foot" should read --12 inches--.

UNITED STATES PATENT OFFICE
CERTIFICATE OF CORRECTION

Patent No. 3,998,714    Dated December 21, 1976

Inventor(s) Edward T. Armstrong

It is certified that error appears in the above-identified patent and that said Letters Patent are hereby corrected as shown below:

Column 56, line 57, "BOD.In" should be -- BOD and in --.

Signed and Sealed this

Sixth Day of September 1977

[SEAL]

Attest:

RUTH C. MASON
Attesting Officer

LUTRELLE F. PARKER
Acting Commissioner of Patents and Trademarks